US011462691B2

(12) United States Patent
Galan et al.

(10) Patent No.: US 11,462,691 B2
(45) Date of Patent: Oct. 4, 2022

(54) ORGANIC ELECTRONIC DEVICE COMPRISING AN ORGANIC SEMICONDUCTOR LAYER

(71) Applicant: Novaled GmbH, Dresden (DE)

(72) Inventors: Elena Galan, Dresden (DE); Francois Cardinali, Dresden (DE); Benjamin Schulze, Dresden (DE)

(73) Assignee: Novaled GmbH, Dresden (DE)

( * ) Notice: Subject to any disclaimer, the term of this patent is extended or adjusted under 35 U.S.C. 154(b) by 358 days.

(21) Appl. No.: 16/755,046

(22) PCT Filed: Oct. 9, 2018

(86) PCT No.: PCT/EP2018/077493
§ 371 (c)(1),
(2) Date: Apr. 9, 2020

(87) PCT Pub. No.: WO2019/072856
PCT Pub. Date: Apr. 18, 2019

(65) Prior Publication Data
US 2021/0083196 A1   Mar. 18, 2021

(30) Foreign Application Priority Data

Oct. 13, 2017 (EP) .................................. 17196446

(51) Int. Cl.
*H01L 51/00* (2006.01)
*C09K 11/06* (2006.01)
*H01L 51/50* (2006.01)

(52) U.S. Cl.
CPC .......... *H01L 51/0067* (2013.01); *C09K 11/06* (2013.01); *H01L 51/0072* (2013.01); *H01L 51/0073* (2013.01); *H01L 51/0074* (2013.01); *H01L 51/0077* (2013.01); *C09K 2211/1018* (2013.01); *H01L 51/5056* (2013.01); *H01L 51/5072* (2013.01); *H01L 51/5092* (2013.01); *H01L 51/5096* (2013.01)

(58) Field of Classification Search
CPC ............ H01L 51/0067; H01L 51/0072; H01L 51/0073; H01L 51/0074
See application file for complete search history.

(56) References Cited

FOREIGN PATENT DOCUMENTS

CN 106167500 A 11/2016
WO 2011/106990 A1 9/2011

OTHER PUBLICATIONS

PCT International Search Report and Written Opinion for PCT Application No. PCT/EP2018/077493 dated Nov. 20, 2018 (11 pages).
Lin et al., "An Elastic Hydrogen-Bonded Cross-Linked Organic Framework for Effective Iodine Capture in Water," J. Am. Chem. Soc., 2017, 139:7172-7175.
(Continued)

*Primary Examiner* — Anthony Ho
(74) *Attorney, Agent, or Firm* — Eversheds Sutherland (US) LLP

(57) ABSTRACT

The present invention relates to compounds comprising a TAE-structure to which a substituted or unsubstituted triazine ring is directly bonded, for use as a layer material for electronic devices, and to an organic electronic device comprising the layer material, and a method of manufacturing the same.

(Continued)

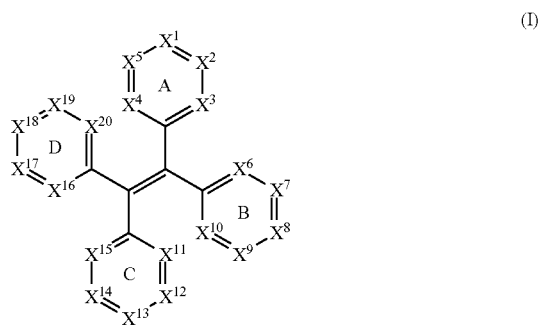

(I)

29 Claims, 3 Drawing Sheets

(56) References Cited

OTHER PUBLICATIONS

Wang et al., "A Flexible Microporous Hydrogen-Bonded Organic Framework for Gas Sorption and Separation," J Am. Chem. Soc., 2015, 137:9963-9970.

Zhao et al., "Electrospun Fibrous Mats with Conjugated Tetraphenylethylene and Mannose for Sensitive Turn-On Fluorescent Sensing of *Escherichia coli*," ACS Appl. Mater. Interfaces, 2015, 7, 9, 5177-5186.

ORGANIC ELECTRONIC DEVICE COMPRISING AN ORGANIC SEMICONDUCTOR LAYER

CROSS REFERENCE TO RELATED APPLICATIONS

This application is a U.S. national phase application of PCT/EP2018/077493, filed Oct. 9, 2018, which claims priority to European Application No, 17196446.3, filed Oct. 13, 2017. The content of these applications is incorporated herein by reference.

TECHNICAL FIELD

The present invention relates to compounds, for use as a layer material for electronic devices, and to an organic electronic device comprising the layer material, and a method of manufacturing the same.

BACKGROUND ART

Organic electronic devices, such as organic light-emitting diodes OLEDs, which are self-emitting devices, have a wide viewing angle, excellent contrast, quick response, high brightness, excellent operating voltage characteristics, and color reproduction. A typical OLED comprises an anode, a hole transport layer HTL, an emission layer EML, an electron transport layer ETL, and a cathode, which are sequentially stacked on a substrate. In this regard, the HTL, the EML, and the ETL are thin films formed from organic compounds.

When a voltage is applied to the anode and the cathode, holes injected from the anode move to the EML, via the HTL, and electrons injected from the cathode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency and/or a long lifetime.

Performance of an organic light emitting diode may be affected by characteristics of the organic semiconductor layer, and among them, may be affected by characteristics of an organic material of the organic semiconductor layer.

Particularly, development for an organic material being capable of increasing electron mobility and simultaneously increasing electrochemical stability is needed so that the organic electronic device, such as an organic light emitting diode, may be applied to a large-size flat panel display.

There remains a need to improve performance of organic semiconductor layers, organic semiconductor materials, as well as organic electronic devices thereof, in particular to achieve higher efficiency through improving the characteristics of the compounds comprised therein.

In particular there is a need for alternative organic semiconductor materials and organic semiconductor layers as well as organic electronic devices having improved efficiency at low operating voltage.

There is a need for alternative compounds having increased efficiency and at the same time keeping the operating voltage and thereby the power consumption low to deliver long battery life for example mobile electronic devices.

DISCLOSURE

An aspect of the present invention provides a compound, for use as a layer material for an organic electronic device, according to formula I:

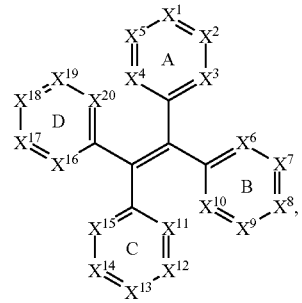

(I)

wherein $X^1$ to $X^{20}$ are independently selected from N, C—H, C—$R^1$, C—Z, and/or at least two of $X^1$ to $X^5$, $X^6$ to $X^{10}$, $X^{11}$ to $X^{15}$, $X^{16}$ to $X^{20}$, which are connected to each other by a chemical bond, are bridged to form an anellated aromatic ring or anellated heteroaromatic ring; and wherein at least one $X^1$ to $X^{20}$ is C—Z; or at least one $X^1$ to $X^{20}$ is C—Z and at least one $X^1$ to $X^{20}$ is C—$R^1$;

$R^1$ is selected from —$NR^2R^3$ or —$BR^2R^3$;

$R^2$ and $R^3$ are independently selected $C_{6-24}$ aryl and $C_{2-20}$ heteroaryl;

Z is a substituent of formula II:

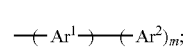

(II)

wherein $Ar^1$ is a substituted or unsubstituted triazine ring,
wherein the substituents of the substituted triazine ring are independently selected from linear $C_{1-20}$ alkyl, branched $C_{3-20}$ alkyl or $C_{3-20}$ cyclic alkyl, linear $C_{1-12}$ fluorinated alkyl, linear $C_{1-12}$ fluorinated alkoxy, branched $C_{3-12}$ fluorinated alkyl, branched $C_{3-12}$ fluorinated alkoxy, $C_{3-12}$ cyclic fluorinated alkyl, $C_{3-12}$ cyclic fluorinated alkoxy, OR, SR, (P=O)$R_2$ or formula I with the exception that $X^1$ to $X^{20}$ are not C—Z;

$Ar^2$ are independently selected from:
formula I, with the exception that $X^1$ to $X^{20}$ are not C—Z,
substituted or unsubstituted $C_{6-60}$ aryl, and substituted or unsubstituted $C_2$-$C_{60}$ heteroaryl;
wherein the substituents of the $C_{6-60}$ aryl and $C_2$-$C_{60}$ heteroaryl are independently selected from $C_1$-$C_{20}$ linear alkyl, $C_3$-$C_{20}$ branched alkyl or $C_3$-$C_{20}$ cyclic alkyl; $C_1$-$C_{20}$ linear alkoxy, $C_3$-$C_{20}$ branched alkoxy; linear fluorinated $C_1$-$C_{12}$ alkyl, or linear fluorinated $C_1$-$C_{12}$ alkoxy; $C_3$-$C_{12}$ branched cyclic fluorinated alkyl, $C_3$-$C_{12}$ cyclic fluorinated alkyl, $C_3$-$C_{12}$ cyclic fluorinated alkoxy; nitrile; OR, SR, (C=O)R, (C=O)$NR_2$, $SiR_3$, (S=O)R, (S=O)$_2$R, (P=O)$R_2$;

R is $C_1$-$C_{20}$ linear alkyl, $C_1$-$C_2$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_2$ heteroaryl;

m is selected from 1, 2 or 3.

According to one embodiment at least one of the aromatic rings A, B, C and D may be connected via a single bond to a triazine ring.

According to one embodiment none of the aromatic rings A, B, C and/or D may be directly bridged with each other, forming an anellated aromatic ring or anellated heteroaromatic ring.

As used herein m=1 means that $Ar^1$ is substituted with one $Ar^2$ substituent.

As used herein m=2 means that $Ar^1$ is substituted with two $Ar^2$ substituents.

As used herein m=3 means that $Ar^1$ is substituted with three $Ar^2$ substituents.

According to another aspect the layer material can be an organic semiconductor layer, which is used for an organic electronic device. For example the organic electronic device can be an OLED or there like.

According to another embodiment Z comprises at least 5 $C_6$ aryl rings, or preferably Z comprises at least 5 $C_6$ aryl rings and at least one 6 member N-hetero aryl ring.

According to another embodiment Z comprises at least 6 $C_6$ aryl rings, or preferably Z comprises at least 6 $C_6$ aryl rings and at least one 6 member N-hetero aryl ring.

According to another embodiment Z comprises at least 7 $C_6$ aryl rings, or preferably Z comprises at least 7 $C_6$ aryl rings and at least one 6 member N-hetero aryl ring.

According to another embodiment Z comprises at least 8 $C_6$ aryl rings, or preferably Z comprises at least 8 $C_6$ aryl rings and at least one 6 member N-hetero aryl ring.

According to another embodiment Z comprises at least 9 $C_6$ aryl rings, or preferably Z comprises at least 9 $C_6$ aryl rings and at least one 6 member N-hetero aryl ring.

According to another embodiment Z comprises at least 10 $C_6$ aryl rings, or preferably Z comprises at least 10 $C_6$ aryl rings and at least one 6 member N-hetero aryl ring.

According to an aspect the layer material can be an organic semiconductor layer, which is used for an organic electronic device. For example the organic electronic device can be an OLED or there like.

According to one embodiment of formula I, wherein the unsubstituted or substituted A, B, C and D arylene rings and/or hetero arylene rings, wherein at least one of the A, B, C and D arylene rings is substituted by C—Z, are bonded each via a single bond to an ethylene group forming the substituted tetraarylethylene compound (TAE) of formula I.

According to one embodiment of formula II, $Ar^1$ and $Ar^2$ are bonded via a single bond.

The compounds represented by formula I have strong electron transport characteristics to increase charge mobility and/or stability and thereby to improve luminance efficiency, voltage characteristics, and/or life-span characteristics.

The compounds represented by formula I have high electron mobility and a low operating voltage.

The organic semiconductor layer may be non-emissive.

In the context of the present specification the term "essentially non-emissive" or "non-emitting" means that the contribution of the compound or layer to the visible emission spectrum from the device is less than 10%, preferably less than 5% relative to the visible emission spectrum. The visible emission spectrum is an emission spectrum with a wavelength of about ≥380 nm to about ≤780 nm.

Preferably, the organic semiconductor layer comprising the compound of formula I is essentially non-emissive or non-emitting.

The term "free of", "does not contain", "does not comprise" does not exclude impurities which may be present in the compounds prior to deposition. Impurities have no technical effect with respect to the object achieved by the present invention.

The operating voltage, also named U, is measured in Volt (V) at 10 milliAmpere per square centimeter (mA/cm2).

The candela per Ampere efficiency, also named cd/A efficiency is measured in candela per ampere at 10 milli-Ampere per square centimeter (mA/cm2).

The external quantum efficiency, also named EQE, is measured in percent (%).

The color space is described by coordinates CIE-x and CIE-y (International Commission on Illumination 1931). For blue emission the CIE-y is of particular importance. A smaller CIE-y denotes a deeper blue color.

The highest occupied molecular orbital, also named HOMO, and lowest unoccupied molecular orbital, also named LUMO, are measured in electron volt (eV).

The term "OLED", "organic light emitting diode", "organic light emitting device", "organic optoelectronic device" and "organic light-emitting diode" are simultaneously used and have the same meaning.

The term "transition metal" means and comprises any element in the d-block of the periodic table, which comprises groups 3 to 12 elements on the periodic table.

The term "group III to VI metal" means and comprises any metal in groups III to VI of the periodic table.

The term "life-span" and "lifetime" are simultaneously used and have the same meaning.

As used herein, "weight percent", "wt.-%", "percent by weight", "% by weight", and variations thereof refer to a composition, component, substance or agent as the weight of that composition, component, substance or agent of the respective electron transport layer divided by the total weight of the composition thereof and multiplied by 100. It is understood that the total weight percent amount of all components, substances or agents of the respective electron transport layer are selected such that it does not exceed 100 wt.-%.

As used herein, "volume percent", "vol.-%", "percent by volume", "% by volume", and variations thereof refer to an elemental metal, a composition, component, substance or agent as the volume of that elemental metal, component, substance or agent of the respective electron transport layer divided by the total volume of the respective electron transport layer thereof and multiplied by 100. It is understood that the total volume percent amount of all elemental metal, components, substances or agents of the respective cathode electrode layer are selected such that it does not exceed 100 vol.-%.

All numeric values are herein assumed to be modified by the term "about", whether or not explicitly indicated. As used herein, the term "about" refers to variation in the numerical quantity that can occur.

Whether or not modified by the term "about", the claims include equivalents to the quantities.

It should be noted that, as used in this specification and the appended claims, the singular forms "a", "an", and "the" include plural referents unless the content clearly dictates otherwise.

The anode electrode and cathode electrode may be described as anode electrode/cathode electrode or anode electrode/cathode electrode or anode electrode layer/cathode electrode layer.

According to another aspect, an organic optoelectronic device comprises an anode layer and a cathode layer facing each other and at least one organic semiconductor layer between the anode layer and the cathode layer, wherein the organic semiconductor layer comprises or consist of the compound of formula I.

According to yet another aspect, a display device comprising the organic electronic device, which can be an organic optoelectronic device, is provided.

In the present specification, when a definition is not otherwise provided, an "alkyl group" may refer to an aliphatic hydrocarbon group. The alkyl group may refer to "a saturated alkyl group" without any double bond or triple bond.

The alkyl group may be a $C_1$ to $C_2$ alkyl group, or preferably a $C_1$ to $C_{12}$ alkyl group.

More specifically, the alkyl group may be a $C_1$ to $C_{20}$ alkyl group, or preferably a $C_1$ to $C_{10}$ alkyl group or a $C_1$ to $C_6$ alkyl group. For example, a $C_1$ to $C_4$ alkyl group comprises 1 to 4 carbons in alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, when a definition is not otherwise provided, R is independently selected from $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl.

Preferably R can be independently selected from $C_1$-$C_{10}$ linear alkyl, $C_1$-$C_{10}$ alkoxy, $C_1$-$C_{10}$ thioalkyl, $C_3$-$C_{10}$ branched alkyl, $C_3$-$C_{10}$ cyclic alkyl, $C_3$-$C_{10}$ branched alkoxy, $C_3$-$C_{10}$ cyclic alkoxy, $C_3$-$C_{10}$ branched thioalkyl, $C_3$-$C_{10}$ cyclic thioalkyl, $C_6$-$C_{18}$ aryl and $C_3$-$C_{18}$ heteroaryl.

Further preferred R can be individually selected from a $C_1$-$C_3$ linear alkyl, $C_6$-$C_{18}$ aryl and $C_3$-$C_{18}$ heteroaryl.

In the present specification "arylene group" may refer to a group comprising at least one hydrocarbon aromatic moiety, and all the elements of the hydrocarbon aromatic moiety may have p-orbitals which form conjugation, for example a phenyl group, a naphtyl group, an anthracenyl group, a phenanthrenyl group, a pyrenyl group, a fluorenyl group and the like.

The arylene group may include a monocyclic, polycyclic or fused ring polycyclic (i.e., rings sharing adjacent pairs of carbon atoms) functional group.

The term "heteroarylene" may refer to aromatic heterocycles with at least one heteroatom, and all the elements of the hydrocarbon heteroaromatic moiety may have p-orbitals which form conjugation. The heteroatom may be selected from N, O, S, B, Si, P, Se, preferably from N, O and S.

A heteroarylene ring may comprise at least 1 to 3 heteroatoms. Preferably a heteroarylene ring may comprise at least 1 to 3 heteroatoms individually selected from N, S and/or O.

Further preferred at least one heteroarylene ring may comprise at least 1 to 3 N-atoms, or at least 1 to 2-N atoms or at least one N-atom.

The term "heteroarylene" as used herewith shall encompass pyridine, quinoline, quinazoline, pyridine, triazine, benzimidazole, benzothiazole, benzo[4,5]thieno[3,2-d]pyrimidine, carbazole, xanthene, phenoxazine, benzoacridine, dibenzoacridine and the like.

In the present specification, the single bond refers to a direct bond.

In the present specification, when a definition is not otherwise provided, $X^1$ to $X^{20}$ are independently selected from N, C—H, C—$R^1$, C—Z, and/or at least two of $X^1$ to $X^5$, $X^6$ to $X^{10}$, $X^{11}$ to $X^{15}$, $X^{16}$ to $X^{20}$, which are connected to each other by a chemical bond, are bridged to form an anellated aromatic ring or anellated heteroaromatic ring, and wherein at least one $X^1$ to $X^{20}$ is selected from C—$R^1$ or C—Z.

Further preferred, $X^1$ to $X^{20}$ can be independently selected from N, C—H, C—$R^1$, C—Z, and/or at least two of $X^1$ to $X^5$, $X^6$ to $X^{10}$, $X^{11}$ to $X^{15}$, $X^{16}$ to $X^{20}$, which are connected to each other by a chemical bond, are bridged to form an anellated aromatic ring or anellated heteroaromatic ring, and one $X^1$ to $X^{20}$ is C—Z.

In addition preferred, $X^1$ to $X^{20}$ can be independently selected from N, C—H, C—Z, and at least one $X^1$ to $X^{20}$ is C—Z.

Also preferred, $X^1$ to $X^{20}$ can be independently selected from C—H, C—Z, and at least one $X^1$ to $X^{20}$ is C—Z.

In the present specification, when a definition is not otherwise provided, $R^1$ is selected from —$NR^2R^3$ or —$BR^2R^3$; and $R^2$ and $R^3$ are independently selected $C_{6-24}$ aryl or $C_{2-20}$ heteroaryl.

Further preferred, $X^1$ to $X^{20}$ in formula I can be free of C—$R^1$.

In the present specification, when a definition is not otherwise provided, is a substituted or unsubstituted triazine ring, wherein the substituents of $C_6$-$C_{60}$ aryl or $C_2$-$C_{60}$ heteroaryl are independently selected from linear $C_{1-20}$ alkyl, branched $C_{3-20}$ alkyl or $C_{3-20}$ cyclic alkyl, linear $C_{1-12}$ fluorinated alkyl, linear $C_{1-12}$ fluorinated alkoxy, branched $C_{3-12}$ fluorinated alkyl, branched $C_{3-12}$ fluorinated alkoxy, $C_{3-12}$ cyclic fluorinated alkyl, $C_{3-12}$ cyclic fluorinated alkoxy, OR, and SR.

Preferably $Ar^1$ is a substituted or unsubstituted triazine ring, wherein the substituents of $C_6$-$C_{18}$ aryl or $C_4$-$C_{17}$ heteroaryl are independently selected from linear $C_{1-10}$ alkyl, branched $C_{3-10}$ alkyl or $C_{3-10}$ cyclic alkyl, linear $C_{1-12}$ fluorinated alkyl, linear $C_{1-12}$ fluorinated alkoxy, branched $C_{3-12}$ fluorinated alkyl, branched $C_{3-12}$ fluorinated alkoxy, $C_{3-12}$ cyclic fluorinated alkyl, $C_{3-12}$ cyclic fluorinated alkoxy, OR, and SR.

Further preferred, $Ar^1$ is a substituted or unsubstituted triazine ring, wherein the substituents of $C_6$-$C_{12}$ aryl or $C_4$-$C_{11}$ heteroaryl are independently selected from linear $C_{1-3}$ alkyl, branched $C_{3-5}$ alkyl, OR, and SR.

Further preferred, $Ar^1$ is a unsubstituted triazine ring.

In the present specification, when a definition is not otherwise provided, $Ar^2$ is independently selected from:
formula I, with the exception that $X^1$ to $X^{20}$ are not C—Z, substituted or unsubstituted $C_{6-60}$ aryl, or substituted or unsubstituted $C_2$-$C_{60}$ heteroaryl; wherein the substituents of the $C_{6-60}$ aryl and $C_2$-$C_{60}$ heteroaryl are independently selected from $C_1$-$C_{20}$ linear alkyl, $C_3$-$C_{20}$ branched alkyl or $C_3$-$C_{20}$ cyclic alkyl; $C_1$-$C_{20}$ linear alkoxy, $C_3$-$C_2$ branched alkoxy; linear fluorinated $C_1$-$C_{12}$ alkyl, or linear fluorinated $C_1$-$C_{12}$ alkoxy; $C_3$-$C_{12}$ branched cyclic fluorinated alkyl, $C_3$-$C_{12}$ cyclic fluorinated alkyl, $C_3$-$C_{12}$ cyclic fluorinated alkoxy, nitrile, OR, SR, (C=O)R, (C=O)$NR_2$, $SiR_3$, (S=O)R, (S=O)$_2$R, and (P=O)$R_2$.

Preferably $Ar^2$ can be independently selected from:
formula I, with the exception that $X^1$ to $X^{20}$ are not C—Z, substituted or unsubstituted $C_{12-60}$ aryl, or substituted or unsubstituted $C_3$-$C_{60}$ heteroaryl; wherein the substituents of the $C_{12-60}$ aryl and $C_3$-$C_{60}$ heteroaryl are independently selected from $C_1$-$C_{10}$ linear alkyl, $C_3$-$C_{10}$ branched alkyl or $C_3$-$C_{10}$ cyclic alkyl; $C_1$-$C_{10}$ linear alkoxy, $C_3$-$C_{10}$ branched alkoxy; linear fluorinated $C_1$-$C_6$ alkyl, or linear fluorinated $C_1$-$C_6$ alkoxy; $C_3$-$C_6$ branched cyclic fluorinated alkyl, $C_3$-$C_6$ cyclic fluorinated alkyl, $C_3$-$C_6$ cyclic fluorinated alkoxy, nitrile, OR, SR, (C=O)R, (C=O)NR$_2$, SiR$_3$, (S=O)R, (S=O)$_2$R, and (P=O)R$_2$.

Further preferred, $Ar^2$ can be independently selected from:
- formula I, with the exception that $X^1$ to $X^{20}$ are not C—Z,
- substituted or unsubstituted $C_{18-60}$ aryl, or substituted or unsubstituted $C_3$-$C_{17}$ heteroaryl; wherein the substituents of the $C_{18-60}$ aryl and $C_3$-$C_{17}$ heteroaryl are independently selected from $C_1$-$C_{10}$ linear alkyl, $C_3$-$C_{10}$ branched alkyl or $C_3$-$C_{10}$ cyclic alkyl; $C_1$-$C_{10}$ linear alkoxy, $C_3$-$C_{10}$ branched alkoxy; linear fluorinated $C_1$-$C_6$ alkyl, or linear fluorinated $C_1$-$C_6$ alkoxy; $C_3$-$C_6$ branched cyclic fluorinated alkyl, $C_3$-$C_6$ cyclic fluorinated alkyl, $C_3$-$C_6$ cyclic fluorinated alkoxy, nitrile, OR, SR, (C=O)R, (C=O)NR$_2$, SiR$_3$, (S=O)R, (S=O)$_2$R, and (P=O)R$_2$.

In addition preferred, $Ar^2$ can be independently selected from:
- formula I, wherein $X^1$ to $X^{20}$ are independently selected from N and C—H, preferably C—H,
- substituted or unsubstituted $C_{24-60}$ aryl, and substituted or unsubstituted $C_3$-$C_{11}$ heteroaryl; wherein the substituents of the $C_{24-60}$ aryl and $C_3$-$C_{11}$ heteroaryl are independently selected from $C_1$-$C_{10}$ linear alkyl, $C_3$-$C_{10}$ branched alkyl or $C_3$-$C_{10}$ cyclic alkyl; $C_1$-$C_{10}$ linear alkoxy, $C_3$-$C_{10}$ branched alkoxy; linear fluorinated $C_1$-$C_6$ alkyl, or linear fluorinated $C_1$-$C_6$ alkoxy; $C_3$-$C_6$ branched cyclic fluorinated alkyl, $C_3$-$C_6$ cyclic fluorinated alkyl, $C_3$-$C_6$ cyclic fluorinated alkoxy, nitrile, OR, SR, (C=O)R, (C=O)NR$_2$, SiR$_3$, (S=O)R, (S=O)$_2$R, and (P=O)R$_2$.

Also preferred, $Ar^2$ can be independently selected from:
- formula I, wherein $X^1$ to $X^{20}$ are independently selected from N and C—H, preferably C—H,
- substituted or unsubstituted $C_{24-60}$ aryl, and substituted or unsubstituted $C_3$-$C_{11}$ heteroaryl; wherein the substituents of the $C_{24-60}$ aryl and $C_3$-$C_{11}$ heteroaryl are independently selected from nitrile and (P=O)R$_2$.

In the present specification, when a definition is not otherwise provided, m is selected from 1, 2 or 3. Further preferred, m can be 1 or 2.

According to one embodiment at least one of the aromatic rings A, B, C and D may comprises one N-atom.

According to one embodiment at least one of the aromatic rings A, B, C and D may comprises two N-atoms.

According to one embodiment at least one of the aromatic rings A, B, C and D may comprises three N-atoms.

According to one embodiment, $Ar^2$ may comprise at least one heteroaryl 6-member ring with one N-atom.

According to one embodiment, $Ar^2$ may comprise at least one heteroaryl 6-member ring with two N-atoms.

According to one embodiment, $Ar^2$ may comprise at least one heteroaryl 6-member ring with three N-atom.

According to one embodiment, $Ar^2$ may comprise at least one heteroaryl 6-member ring that is a triazine.

According to one embodiment the compound according to formula I:
- comprises at least 5 to 20 aromatic rings, preferably at least 6 to 18 aromatic rings, further preferred at least 7 to 16 aromatic rings, in addition preferred at least 8 to 15 aromatic rings and more preferred at least 8 to 14 aromatic rings; and/or the compound of formula I comprises at least 1 to 5, preferably 2 to 4 or 2 to 3, hetero aromatic rings; and/or
- comprises at least one of the aromatic rings A, B, C and D, wherein at least one thereof is different substituted, further preferred at least two of the aromatic rings A, B, C and D of formula I are substituted different; and/or
- is non-superimposable on its mirror image; and/or
- comprises at least one hetero atom N, O, S and/or a substituent of (P=O)R$_2$, —CN, preferably at least one hetero atom N, two or three hetero N atoms, further preferred at least one hetero N and at least one substituent selected from (P=O)R$_2$, or —CN; and/or
- comprises at least two triazine ring; and/or
- comprises one non-hetero tetraarylethylene group (TAE) only and/or one hetero tetraarylethylene group (TAE) only.

According to one preferred embodiment the compound according to formula I may comprises at least 5 to 20 aromatic rings and at least one triazine ring; preferably at least 6 to 18 aromatic rings and at least one triazine ring; further preferred at least 7 to 16 aromatic rings and at least one triazine ring; in addition preferred at least 8 to 15 aromatic rings and at least one triazine ring; and more preferred at least 8 to 14 aromatic rings and at least one triazine ring.

According to one preferred embodiment the compound of formula I comprises at least 1 to 5, preferably 2 to 4 or 2 to 3, hetero aromatic rings; wherein at least one hetero aromatic ring is a triazine ring.

According to one preferred embodiment the compound according to formula I may comprise:
- at least 5 to 20 aromatic rings, preferably at least 6 to 18 aromatic rings, further preferred at least 7 to 16 aromatic rings, in addition preferred at least 8 to 15 aromatic rings and more preferred at least 8 to 14 aromatic rings; and
- at least 1 to 5, preferably 2 to 4 or 2 to 3, hetero aromatic rings, wherein at least one hetero aromatic ring is a triazine ring.

According to one embodiment the compound according to formula I may comprise at least 6 to 12 non-hetero aromatic rings and 1 to 3 hetero aromatic rings, wherein at least one hetero aromatic ring is a triazine ring.

According to one preferred embodiment the compound according to formula I may comprise at least 6 to 12 non-hetero aromatic rings and 1 to 3 hetero aromatic rings, wherein at least one hetero aromatic ring is a triazine ring.

According to one preferred embodiment the compound according to formula I may comprise at least 7 to 11 non-hetero aromatic rings and 1 to 2 hetero aromatic rings, wherein at least one hetero aromatic ring is a triazine ring.

According to one preferred embodiment the compound according to formula I may comprise at least 6 to 12 non-substituted or substituted non-hetero aromatic rings and at least 1 to 3 non-substituted or substituted hetero aromatic rings, wherein at least one hetero aromatic ring is a triazine ring, and at least 1 to 3 substituents selected from nitrile, di-alkyl phosphine oxide, di-aryl phosphine oxide, $C_2$-$C_{16}$ heteroaryl, fluorinated $C_1$-$C_6$ alkyl or fluorinated $C_1$-$C_6$ alkoxy, preferably nitrile or di-alkyl phosphine oxide.

According to one preferred embodiment the compound according to formula I may comprise at least 7 to 11 non-substituted or substituted non-hetero aromatic rings and at least one hetero aromatic ring, which is a triazine ring, and at least one substituent selected from nitrile, di-alkyl phosphine oxide, di-aryl phosphine oxide, $C_2$-$C_{16}$ heteroaryl, fluorinated $C_1$-$C_6$ alkyl or fluorinated $C_1$-$C_6$ alkoxy; wherein at least one non-hetero aromatic ring is substituted.

According to one preferred embodiment the compound according to formula I may comprise at least 7 to 11 non-substituted or substituted non-hetero aromatic rings and at least one hetero aromatic ring and at least one substituent selected from nitrile and/or di-alkyl phosphine oxide; wherein at least one non-hetero aromatic ring is substituted.

According to one preferred embodiment the compound according to formula I may comprises at least one of the aromatic rings A, B, C and D, wherein at least one aromatic ring thereof is different substituted, further preferred at least two of the aromatic rings A, B, C and D of formula I are different substituted.

According to one preferred embodiment the compound according to formula I can be non-superimposable on its mirror image.

According to one preferred embodiment the compound according to formula I may comprises at least one hetero atom selected from N, O, and/or S, preferably at least one N, two or three N atoms.

According to one preferred embodiment the compound according to formula I may comprises at least one substituent selected from nitrile, OR, SR, (C═O)R, (C═O)NR$_2$, SiR$_3$, (S═O)R, (S═O)$_2$R, (P═O)R$_2$.

According to one preferred embodiment the compound according to formula I may comprises at least one hetero atom selected from N, O, and/or S, and at least one substituent selected from nitrile, OR, SR, (C═O)R, (C═O)NR$_2$, SiR$_3$, (S═O)R, (S═O)$_2$R, (P═O)R$_2$.

According to one preferred embodiment the compound according to formula I may comprises at least one N and in addition at least one hetero atom selected from N, O, and/or S, and at least one substituent selected from nitrile, and/or (P═O)R$_2$.

According to one preferred embodiment the compound according to formula I may comprises at least two triazine rings.

According to one preferred embodiment the compound according to formula I may comprises one non-hetero tetraarylethylene group (TAE) only and/or one hetero tetraarylethylene group (TAE) only.

According to one preferred embodiment the compound according to formula I may comprises at least two non-hetero tetraarylethylene group (TAE).

Non-hetero tetraarylethylene (TAE) group means that none of the aryl substituents at the ethylene comprises a hetero atom, which is an atom different from carbon or hydrogen.

Hetero tetraarylethylene (TAE) group means that at least one of the aryl substituents at the ethylene comprises at least one hetero atom, which is an atom different from carbon or hydrogen.

The term "$C_6$-arylene ring" means single $C_6$-arylene rings and $C_6$-arylene rings which form condensed ring systems. For example, a naphthalene group would be counted as two $C_6$-arylene rings.

According to another embodiment of formula I, wherein for Ar$^2$ at least one heteroarylene group is selected from triazine, quinazoline, benzimidazole, benzothiazole, benzo[4,5]thieno[3,2-d]pyrimidine, pyrimidine and pyridine and is preferably selected from triazine and pyrimidine.

According to another embodiment, wherein the compound of formula I may have a dipole moment of about ≥0 and about ≤3 Debye, preferably about ≥0 and about ≤2 Debye.

Preferably, the dipole moment of the compound of formula I may be selected ≥0 and ≤1 Debye, further preferred ≥0 and ≤0.8 Debye, also preferred ≥0 and ≤0.4 Debye.

Surprisingly, it has been found that particularly high conductivity and low operating voltage of an organic semiconductor layer comprising compounds of formula I may be obtained when the dipole moment of compound for formula I is selected in this range.

The dipole moment $|\vec{\mu}|$ of a molecule containing N atoms is given by:

$$\vec{\mu} = \sum_i^N q_i \vec{r}_i$$

$$|\vec{\mu}| = \sqrt{\mu_x^2 + \mu_y^2 + \mu_z^2}$$

where $q_i$ and $\vec{r}_i$ are the partial charge and position of atom in the molecule.

The dipole moment is determined by a semi-empirical molecular orbital method.

The partial charges and atomic positions in the gas phase are obtained using the hybrid functional B3LYP with a 6-31G* basis set as implemented in the program package TURBOMOLE V6.5. If more than one conformation is viable, the conformation with the lowest total energy is selected to determine the dipole moment.

According to another embodiment, the reduction potential of the compound of formula I may be selected more negative than −1.9 V and less negative than −2.6 V against Fc/Fc$^+$ in tetrahydrofuran, preferably more negative than −2 V and less negative than −2.5 V.

The reduction potential may be determined by cyclic voltammetry with potentiostatic device Metrohm PGSTAT30 and software Metrohm Autolab GPES at room temperature. The redox potentials are measured in an argon de-aerated, anhydrous 0.1M THF solution of the compound of formula I, under argon atmosphere, with 0.1M tetrabutylammonium hexafluorophosphate as supporting electrolyte, between platinum working electrodes and with an Ag/AgCl pseudo-standard electrode (Metrohm Silver rod electrode), consisting of a silver wire covered by silver chloride and immersed directly in the measured solution, with the scan rate 100 mV/s. The first run is done in the broadest range of the potential set on the working electrodes, and the range is then adjusted within subsequent runs appropriately. The final three runs are done with the addition of ferrocene (in 0.1M concentration) as the standard. The average of potentials corresponding to cathodic and anodic peak of the compound is determined through subtraction of the average of cathodic and anodic potentials observed for the standard Fc$^+$/Fc redox couple.

Particularly good electron injection and/or electron transport into the emission layer and/or stability may be achieved if the reduction potential is selected in this range.

According to another embodiment the compound of formula I may have a glass transition temperature Tg of about ≥105° C. and about ≤380° C., preferably about ≥110° C. and about ≤350° C., further preferred about ≥150° C. and about ≤320° C.

According to another embodiment the compound of formula I may have a glass transition temperature Tg of about ≥105° C. and about ≤170° C.

The glass transition temperature is measured under nitrogen and using a heating rate of 10 K per min in a Mettler Toledo DSC 822e differential scanning calorimeter as described in DIN EN ISO 11357, published in March 2010.

According to another embodiment the compound of formula I may have a rate onset temperature $T_{RO}$ of about ≥150° C. and ≤400° C., preferably about ≥180° C. and about ≤380° C.

Weight loss curves in TGA (thermogravimetric analysis) are measured by means of a Mettler Toledo TGA-DSC 1 system, heating of samples from room temperature to 600° C. with heating rate 10 K/min under a stream of pure nitrogen. 9 to 11 mg sample are placed in a 100 μL Mettler Toledo aluminum pan without lid. The temperature is determined at which 0.5 wt.-% weight loss occurs.

Room temperature, also named ambient temperature, is 23° C.

The rate onset temperature for transfer into the gas phase is determined by loading 100 mg compound into a VTE source. As VTE source a point source for organic materials is used as supplied by Kurt J. Lesker Company (www.lesker.com) or CreaPhys GmbH (http://www.creaphys.com). The VTE (vacuum thermal evaporation) source temperature is determined through a thermocouple in direct contact with the compound in the VTE source.

The VTE source is heated at a constant rate of 15 K/min at a pressure of $10^{-7}$ to $10^{-8}$ mbar in the vacuum chamber and the temperature inside the source measured with a thermocouple.

Evaporation of the compound is detected with a QCM detector which detects deposition of the compound on the quartz crystal of the detector. The deposition rate on the quartz crystal is measured in Å ngstrom per second. To determine the rate onset temperature, the deposition rate on a logarithmic scale is plotted against the VTE source temperature. The rate onset is the temperature at which noticeable deposition on the QCM detector occurs (defined as a rate of 0.02 Å/s. The VTE source is heated and cooled three time and only results from the second and third run are used to determine the rate onset temperature.

The rate onset temperature is an indirect measure of the volatility of a compound. The higher the rate onset temperature the lower is the volatility of a compound.

Surprisingly, it was found that the compounds of formula I and the inventive organic electronic devices solve the problem underlying the present invention by being superior over the organic electroluminescent devices and compounds known in the art, in particular with respect to cd/A efficiency, also referred to as current efficiency. At the same time the operating voltage is kept at a similar or even improved level which is important for reducing power consumption and increasing battery life, for example of a mobile display device. High cd/A efficiency is important for high efficiency and thereby increased battery life of a mobile device, for example a mobile display device.

The inventors have surprisingly found that particular good performance can be achieved when using the organic electroluminescent device as a fluorescent blue device.

The specific arrangements mentioned herein as preferred were found to be particularly advantageous.

Likewise, some compounds falling within the scope of the broadest definition of the present invention have surprisingly be found to be particularly well performing with respect to the mentioned property of cd/A efficiency. These compounds are discussed herein to be particularly preferred.

Further an organic optoelectronic device having high efficiency and/or long life-span may be realized.

Hereinafter, a compound for an organic optoelectronic device according to an embodiment is described.

A compound for an organic optoelectronic device according to an embodiment is represented by formula I according to the invention.

The compound of the invention of formula I may help injection or transport of electrons or increases a glass transition temperature of the compound, and thus luminance efficiency may be increased due to suppression of an intermolecular interaction, and the compound may have a low deposition temperature relative to the molecular weight.

Accordingly, when the compound for an organic optoelectronic device represented by formula I forms a film or layer, the compound may optimize injection and transport of holes or electrons and the film or layer durability in the device due to the specific steric shape of the compound of formula I. Thereby, a better intermolecular arrangement of charge transporting groups may be achieved.

Therefore, when the compound of formula I are used for an organic optoelectronic device these compounds may increase luminance efficiency due to rapid injection of electrons into an emission layer. On the other hand, when the compound is mixed with a material having excellent hole injection or transport characteristics to form the emission layer, the compound may also obtain excellent luminance efficiency due to efficient charge injection and formation of excitons.

In addition, excellent electron injection and transport characteristics of the compound for an organic optoelectronic device represented by formula I may be obtained. In addition, the compound of formula I may still maintain excellent electron injection and transport characteristics even when used to from an electron injection auxiliary layer or to form an emission layer as a mixture with a compound having excellent hole characteristics.

According to one embodiment a compound, for use as a layer material for an organic electronic device, according to formula I is provided:

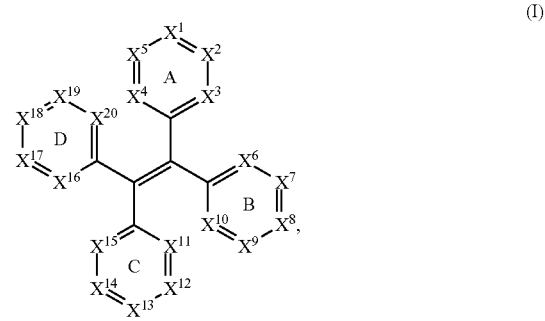

(I)

wherein $X^1$ to $X^{20}$ are independently selected from N, C—H, C—$R^1$, C—Z, and/or at least two of $X^1$ to $X^5$, $X^6$ to $X^{10}$, $X^{11}$ to $X^{15}$, $X^{16}$ to $X^{20}$, which are connected to each other by a chemical bond, are bridged to form an anellated aromatic ring or anellated heteroaromatic ring; and wherein at least one $X^1$ to $X^{20}$ is C—Z;

Z is a substituent of formula II:

(II)

wherein
Ar$^1$ is a substituted or unsubstituted triazine ring,
wherein the substituents of the substituted triazine ring are independently selected from linear $C_{1-20}$ alkyl, branched $C_{3-20}$ alkyl or $C_{3-20}$ cyclic alkyl, linear $C_{1-12}$ fluorinated alkyl, linear $C_{1-12}$ fluorinated alkoxy, branched $C_{3-12}$ fluorinated alkyl, branched $C_{3-12}$ fluorinated alkoxy, $C_{3-12}$ cyclic fluorinated alkyl, $C_{3-12}$ cyclic fluorinated alkoxy, OR, SR, (P=O)R$_2$ or formula I with the exception that X$^1$ to X$^{20}$ are not C—Z;

Ar$^2$ are independently selected from:
formula I, with the exception that X$^1$ to X$^{20}$ are not C—Z,
substituted or unsubstituted $C_{6-60}$ aryl, and substituted or unsubstituted $C_2$-$C_{60}$ heteroaryl;
wherein the substituents of the $C_{6-60}$ aryl and $C_2$-$C_{60}$ heteroaryl are independently selected from $C_1$-$C_{20}$ linear alkyl, $C_3$-$C_{20}$ branched alkyl or $C_3$-$C_{20}$ cyclic alkyl; $C_1$-$C_{20}$ linear alkoxy, $C_3$-$C_{20}$ branched alkoxy; linear fluorinated $C_1$-$C_{12}$ alkyl, or linear fluorinated $C_1$-$C_{12}$ alkoxy; $C_3$-$C_{12}$ branched cyclic fluorinated alkyl, $C_3$-$C_{12}$ cyclic fluorinated alkoxy; nitrile; OR, SR, (C=O)R, (C=O)NR$_2$, SiR$_3$, (S=O)R, (S=O)$_2$R, (P=O)R$_2$;

R is $C_1$-$C_{20}$ linear alkyl, $C_1$-$C_{20}$ alkoxy, $C_1$-$C_{20}$ thioalkyl, $C_3$-$C_2$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl;

m is selected from 1, 2 or 3.

According to one embodiment a compound, for use as a layer material for an organic electronic device, according to formula I is provided:

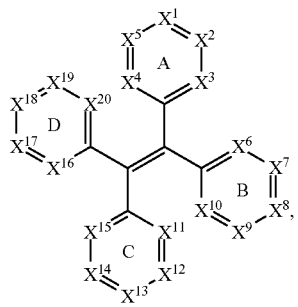

(I)

wherein
X$^1$ to X$^{20}$ are independently selected from N, C—H, C—R$^1$, C—Z, and/or at least two of X$^1$ to X$^5$, X$^6$ to X$^{10}$, X$^{11}$ to X$^{15}$, X$^{16}$ to X$^{20}$, which are connected to each other by a chemical bond, are bridged to form an anellated aromatic ring or anellated heteroaromatic ring; and
wherein at least one X$^1$ to X$^{20}$ is C—Z;
Z is a substituent of formula II:

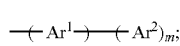

(II)

wherein
Ar$^1$ is a substituted or unsubstituted triazine ring,
wherein the substituents are independently selected from linear $C_{1-20}$ alkyl, branched $C_{3-20}$ alkyl or $C_{3-20}$ cyclic alkyl, linear $C_{1-12}$ fluorinated alkyl, linear $C_{1-12}$ fluorinated alkoxy, branched $C_{3-12}$ fluorinated alkyl, branched $C_{3-12}$ fluorinated alkoxy, $C_{3-12}$ cyclic fluorinated alkyl, $C_{3-12}$ cyclic fluorinated alkoxy, OR, SR, (P=O)R$_2$ or formula I with the exception that X$^1$ to X$^{20}$ are not C—Z;

Ar$^2$ are independently selected from:
formula I, with the exception that X$^1$ to X$^{20}$ are not C—Z,
substituted or unsubstituted $C_{6-60}$ aryl, and substituted or unsubstituted $C_2$-$C_{60}$ heteroaryl;
wherein the substituents of the $C_{6-60}$ aryl and $C_2$-$C_{60}$ heteroaryl are independently selected from $C_1$-$C_{20}$ linear alkyl, $C_3$-$C_{20}$ branched alkyl, $C_3$-$C_{20}$ cyclic alkyl; $C_1$-$C_{20}$ linear alkoxy, $C_3$-$C_{20}$ branched alkoxy; linear fluorinated $C_1$-$C_{12}$ alkyl, or linear fluorinated $C_1$-$C_{12}$ alkoxy; $C_3$-$C_{12}$ branched cyclic fluorinated alkyl, $C_3$-$C_{12}$ cyclic fluorinated alkyl, $C_3$-$C_{12}$ cyclic fluorinated alkoxy; nitrile; OR, SR, (C=O)R, (C=O)NR$_2$, SiR$_3$, (S=O)R, (S=O)$_2$R, (P=O)R$_2$;

R is $C_1$-$C_{20}$ linear alkyl, $C_1$-$C_{20}$ alkoxy, $C_1$-$C_{20}$ thioalkyl, $C_3$-$C_2$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl;

m is selected from 1, 2 or 3; wherein at least one of the aromatic rings A, B, C and D are connected via a single bond to a triazine ring; and wherein compounds of formula I that are superimposable on its mirror image are excluded.

According to one embodiment a compound, for use as a layer material for an organic electronic device, according to formula I is provided:

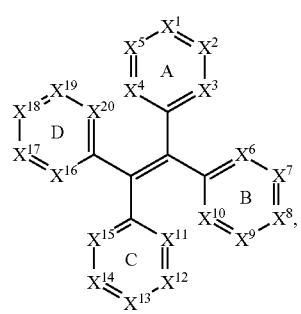

(I)

wherein
X$^1$ to X$^{20}$ are independently selected from N, C—H, C—R$^1$, C—Z, and/or at least two of X$^1$ to X$^5$, X$^6$ to X$^{10}$, X$^{11}$ to X$^{15}$, X$^{16}$ to X$^{20}$, which are connected to each other by a chemical bond, are bridged to form an anellated aromatic ring or anellated heteroaromatic ring; and
wherein at least one X$^1$ to X$^{20}$ is C—Z; or optional at least one X$^1$ to X$^{20}$ is C—Z and at least one X$^1$ to X$^{20}$ is C—R$^1$;

R$^1$ is selected from —NR$^2$R$^3$ or —BR$^2$R$^3$;

R$^2$ and R$^3$ are independently selected $C_{6-24}$ aryl and $C_{2-20}$ heteroaryl;

Z is a substituent of formula II:

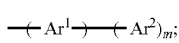
(II)

wherein
Ar$^1$ is a substituted or unsubstituted triazine ring, wherein the substituents are independently selected from linear C$_{1-20}$ alkyl, branched C$_{3-20}$ alkyl or C$_{3-20}$ cyclic alkyl, linear C$_{1-12}$ fluorinated alkyl, linear C$_{1-12}$ fluorinated alkoxy, branched C$_{3-12}$ fluorinated alkyl, branched C$_{3-12}$ fluorinated alkoxy, C$_{3-12}$ cyclic fluorinated alkyl, C$_{3-12}$ cyclic fluorinated alkoxy, OR, SR, (P=O)R$_2$ or formula 1 with the exception that X$^1$ to X$^{20}$ are not C—Z;
Ar$^2$ are independently selected from:
  formula I, with the exception that X$^1$ to X$^{20}$ are not C—Z,
  substituted or unsubstituted C$_{6-60}$ aryl, and substituted or unsubstituted C$_2$-C$_{60}$ heteroaryl;
  wherein the substituents of the C$_{6-60}$ aryl and C$_2$-C$_{60}$ heteroaryl are independently selected from C$_1$-C$_{20}$ linear alkyl, C$_3$-C$_{20}$ branched alkyl, C$_3$-C$_{20}$ cyclic alkyl; C$_1$-C$_{20}$ linear alkoxy, C$_3$-C$_{20}$ branched alkoxy; linear fluorinated C$_1$-C$_{12}$ alkyl, or linear fluorinated C$_1$-C$_{12}$ alkoxy; C$_3$-C$_{12}$ branched cyclic fluorinated alkyl, C$_3$-C$_{12}$ cyclic fluorinated alkyl, C$_3$-C$_{12}$ cyclic fluorinated alkoxy; nitrile; OR, SR, (C=O)R, (C=O)NR$_2$, SiR$_3$, (S=O)R, (S=O)$_2$R, (P=O)R$_2$;
R is C$_1$-C$_{20}$ linear alkyl, C$_1$-C$_{20}$ alkoxy, C$_1$-C$_{20}$ thioalkyl, C$_3$-C$_2$ branched alkyl, C$_3$-C$_{20}$ cyclic alkyl, C$_3$-C$_{20}$ branched alkoxy, C$_3$-C$_{20}$ cyclic alkoxy, C$_3$-C$_{20}$ branched thioalkyl, C$_3$-C$_{20}$ cyclic thioalkyl, C$_6$-C$_{20}$ aryl and C$_3$-C$_{20}$ heteroaryl;
m is selected from 1 or 2; wherein
at least one of the aromatic rings A, B, C and D are connected via a single bond to a triazine ring.

According to one embodiment a compound, for use as a layer material for an organic electronic device, according to formula I is provided:

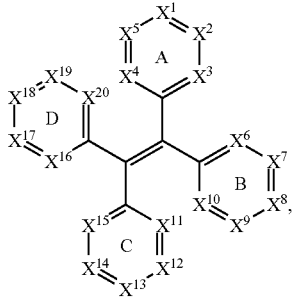
(I)

wherein
X$^1$ to X$^{20}$ are independently selected from N, C—H, C—R$^1$, C—Z, and/or at least two of X$^1$ to X$^5$, X$^6$ to X$^{10}$, X$^{11}$ to X$^{15}$, X$^{16}$ to X$^{20}$, which are connected to each other by a chemical bond, are bridged to form an anellated aromatic ring or anellated heteroaromatic ring; and
wherein at least one X$^1$ to X$^{20}$ is C—Z; or at least one X$^1$ to X$^{20}$ is C—Z and optional at least one X$^1$ to X$^{20}$ is C—R$^1$;

R$^1$ is selected from —NR$^2$R$^3$ or —BR$^2$R$^3$;
R$^2$ and R$^3$ are independently selected C$_{6-24}$ aryl and C$_{2-20}$ heteroaryl;
Z is a substituent of formula II:

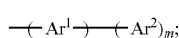
(II)

wherein
Ar$^1$ is a substituted or unsubstituted triazine ring, wherein the substituents are independently selected from linear C$_{1-20}$ alkyl, branched C$_{3-20}$ alkyl or C$_{3-20}$ cyclic alkyl, linear C$_{1-12}$ fluorinated alkyl, linear C$_{1-12}$ fluorinated alkoxy, branched C$_{3-12}$ fluorinated alkyl, branched C$_{3-12}$ fluorinated alkoxy, C$_{3-12}$ cyclic fluorinated alkyl, C$_{3-12}$ cyclic fluorinated alkoxy, OR, SR, (P=O)R$_2$;
Ar$^2$ are independently selected from:
  formula I, with the exception that X$^1$ to X$^{20}$ are not C—Z,
  substituted or unsubstituted C$_{6-60}$ aryl, and substituted or unsubstituted C$_2$-C$_{60}$ heteroaryl;
  wherein the substituents of the C$_{6-60}$ aryl and C$_2$-C$_{60}$ heteroaryl are independently selected from C$_1$-C$_{20}$ linear alkyl, C$_3$-C$_{20}$ branched alkyl, C$_3$-C$_{20}$ cyclic alkyl; C$_1$-C$_{20}$ linear alkoxy, C$_3$-C$_{20}$ branched alkoxy; linear fluorinated C$_1$-C$_{12}$ alkyl, or linear fluorinated C$_1$-C$_{12}$ alkoxy; C$_3$-C$_{12}$ branched cyclic fluorinated alkyl, C$_3$-C$_{12}$ cyclic fluorinated alkyl, C$_3$-C$_{12}$ cyclic fluorinated alkoxy; nitrile; OR, SR, (C=O)R, (C=O)NR$_2$, SiR$_3$, (S=O)R, (S=O)$_2$R, (P=O)R$_2$;
R is C$_1$-C$_{20}$ linear alkyl, C$_1$-C$_{20}$ alkoxy, C$_1$-C$_{20}$ thioalkyl, C$_3$-C$_2$ branched alkyl, C$_3$-C$_{20}$ cyclic alkyl, C$_3$-C$_{20}$ branched alkoxy, C$_3$-C$_{20}$ cyclic alkoxy, C$_3$-C$_{20}$ branched thioalkyl, C$_3$-C$_{20}$ cyclic thioalkyl, C$_6$-C$_{20}$ aryl and C$_3$-C$_{20}$ heteroaryl;
m is selected from 1, 2 or 3; wherein
at least one of the aromatic rings A, B, C and D are connected via a single bond to a triazine ring.

According to one embodiment a compound, for use as a layer material for an organic electronic device, according to formula I is provided:

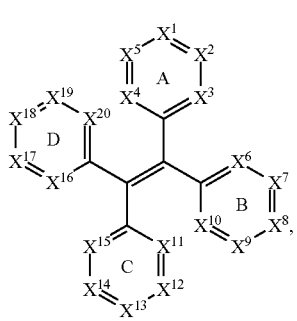
(I)

wherein
X$^1$ to X$^{20}$ are independently selected from N, C—H, C—R$^1$, C—Z, and/or at least two of X$^1$ to X$^5$, X$^6$ to X$^{10}$, X$^{11}$ to X$^{15}$, X$^{16}$ to X$^{20}$, which are connected to each other by a chemical bond, are bridged to form an anellated aromatic ring or anellated heteroaromatic ring; and wherein at least one $X^1$ to $X^{20}$ is C—Z; or optional at least one $X^1$ to $X^{20}$ is C—Z and at least one $X^1$ to $X^{20}$ is C—$R^1$;

$R^1$ is selected from —$NR^2R^3$ or —$BR^2R^3$;

$R^2$ and $R^3$ are independently selected $C_{6-24}$ aryl and $C_{2-20}$ heteroaryl;

Z is a substituent of formula II:

(II)

wherein $Ar^1$ is a substituted or unsubstituted triazine ring, wherein the substituents of $C_6$-$C_{60}$ aryl or $C_2$-$C_{60}$ heteroaryl are independently selected from linear $C_{1-20}$ alkyl, branched $C_{3-20}$ alkyl or $C_{3-20}$ cyclic alkyl, linear $C_{1-12}$ fluorinated alkyl, linear $C_{1-12}$ fluorinated alkoxy, branched $C_{3-12}$ fluorinated alkyl, branched $C_{3-12}$ fluorinated alkoxy, $C_{3-12}$ cyclic fluorinated alkyl, $C_{3-12}$ cyclic fluorinated alkoxy, OR, SR, (P=O)$R_2$;

$Ar^2$ are independently selected from:
formula I, with the exception that $X^1$ to $X^{20}$ are not C—Z,
substituted or unsubstituted $C_{6-60}$ aryl, and substituted or unsubstituted $C_{2-60}$ heteroaryl;
wherein the substituents of the $C_{6-60}$ aryl and $C_{2-60}$ heteroaryl are independently selected from $C_1$-$C_{20}$ linear alkyl, $C_3$-$C_{20}$ branched alkyl or $C_3$-$C_{20}$ cyclic alkyl; $C_1$-$C_{20}$ linear alkoxy, $C_3$-$C_{20}$ branched alkoxy; linear fluorinated $C_1$-$C_{12}$ alkyl, or linear fluorinated $C_1$-$C_{12}$ alkoxy; $C_3$-$C_{12}$ branched cyclic fluorinated alkyl, $C_3$-$C_{12}$ cyclic fluorinated alkyl, $C_3$-$C_{12}$ cyclic fluorinated alkoxy; nitrile; OR, SR, (C=O)R, (C=O)$NR_2$, $SiR_3$, (S=O)R, (S=O)$_2$R, (P=O)$R_2$;

R is $C_1$-$C_{20}$ linear alkyl, $C_1$-$C_{20}$ alkoxy, $C_1$-$C_{20}$ thioalkyl, $C_3$-$C_2$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl;

m is selected from 1, 2 or 3; wherein none at least one of the aromatic rings A, B, C and D are connected via a single bond to a triazine ring; wherein compounds of formula I that are superimposable on its mirror image are excluded, and wherein compounds of formula I, wherein $Ar^1$ and $Ar^2$ are identical, are excluded.

According to one embodiment a compound, for use as a layer material for an organic electronic device, according to formula I is provided:

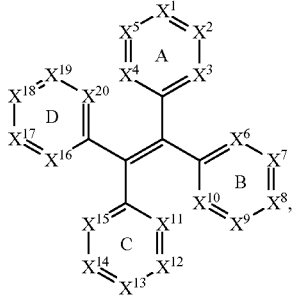

(I)

wherein $X^1$ to $X^{20}$ are independently selected from N, C—H, C—$R^1$, C—Z, and/or at least two of $X^1$ to $X^5$, $X^6$ to $X^{10}$, $X^{11}$ to $X^{15}$, $X^{16}$ to $X^{20}$, which are connected to each other by a chemical bond, are bridged to form an anellated aromatic ring or anellated heteroaromatic ring; and wherein at least one $X^1$ to $X^{20}$ is C—Z; or optional at least one $X^1$ to $X^{20}$ is C—Z and at least one $X^1$ to $X^{20}$ is C—$R^1$;

$R^1$ is selected from —$NR^2R^3$ or —$BR^2R^3$;

$R^2$ and $R^3$ are independently selected $C_{6-24}$ aryl and $C_{2-20}$ heteroaryl;

Z is a substituent of formula II:

(II)

wherein $Ar^1$ is a substituted or unsubstituted triazine ring, wherein the substituents of $C_6$-$C_{60}$ aryl or $C_2$-$C_{60}$ heteroaryl are independently selected from linear $C_{1-20}$ alkyl, branched $C_{3-20}$ alkyl or $C_{3-20}$ cyclic alkyl, linear $C_{1-12}$ fluorinated alkyl, linear $C_{1-12}$ fluorinated alkoxy, branched $C_{3-12}$ fluorinated alkyl, branched $C_{3-12}$ fluorinated alkoxy, $C_{3-12}$ cyclic fluorinated alkyl, $C_{3-12}$ cyclic fluorinated alkoxy, OR, SR, (P=O)$R_2$;

$Ar^2$ are independently selected from:
formula I, with the exception that $X^1$ to $X^{20}$ are not C—Z,
substituted or unsubstituted $C_{6-60}$ aryl, and substituted or unsubstituted $C_{2-60}$ heteroaryl;
wherein the substituents of the $C_{6-60}$ aryl and $C_{2-60}$ heteroaryl are independently selected from $C_1$-$C_{20}$ linear alkyl, $C_3$-$C_{20}$ branched alkyl or $C_3$-$C_{20}$ cyclic alkyl; $C_1$-$C_{20}$ linear alkoxy, $C_3$-$C_{20}$ branched alkoxy; linear fluorinated $C_1$-$C_{12}$ alkyl, or linear fluorinated $C_1$-$C_{12}$ alkoxy; $C_3$-$C_{12}$ branched cyclic fluorinated alkyl, $C_3$-$C_{12}$ cyclic fluorinated alkyl, $C_3$-$C_{12}$ cyclic fluorinated alkoxy; nitrile; OR, SR, (C=O)R, (C=O)$NR_2$, $SiR_3$, (S=O)R, (S=O)$_2$R, (P=O)$R_2$;

R is $C_1$-$C_{20}$ linear alkyl, $C_1$-$C_{20}$ alkoxy, $C_1$-$C_{20}$ thioalkyl, $C_3$-$C_2$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl;

m is selected from 0, 1, 2 or 3; wherein at least one of the aromatic rings A, B, C and D are connected via a single bond to a triazine ring; wherein compounds of formula I that are superimposable on its mirror image are excluded, wherein compounds of formula I, wherein $Ar^1$ and $Ar^2$ are identical, are excluded; and wherein Z comprises at least 4 $C_6$ aryl rings, or preferably Z comprises at least 4 $C_6$ aryl rings and at least one 6 member N-hetero aryl ring.

According to one embodiment of the compound according to formula I:
the $Ar^1$ group is a triazine ring; and
the $Ar^2$ group may comprises 1 to 10 non-hetero aromatic 6 membered rings, preferably 2 to 8 non-hetero aromatic 6 membered rings, further preferred 3 to 6 non-hetero aromatic 6 membered rings; in addition preferred 4 or 5 non-hetero aromatic 6 membered rings; and/or at least one $C_6$ to Cis arylene, preferably at least one $C_6$ or $C_{12}$ arylene, is anellated to at least on aromatic ring A, B, C and D of formula (I).

According to one embodiment, wherein in formula I:
$X^1$ to $X^{20}$ are independently selected from C—H, C—$R^1$, C—Z,
  wherein at least one $X^1$ to $X^{20}$ is selected from C—Z;
$R^1$ is selected from —$NR^2R^3$ or —$BR^2R^3$;
$R^2$ and $R^3$ are independently selected $C_{6-16}$ aryl or $C_{2-12}$ heteroaryl;
Z is a substituent of formula II:

$$-\!\!+\!Ar^1\!\!+\!\!\!\!\!\!-_n\!\!+\!Ar^2)_m, \quad (II)$$

wherein
$Ar^1$ is a triazine ring;
$Ar^2$ are independently selected from substituted or unsubstituted $C_{12-60}$ aryl and substituted or unsubstituted $C_{10}$-$C_{59}$ heteroaryl,
  wherein the substituents are independently selected from nitrile, di-alkyl phosphine oxide, di-aryl phosphine oxide, $C_2$-$C_{16}$ heteroaryl, fluorinated $C_1$-$C_6$ alkyl or fluorinated $C_1$-$C_6$ alkoxy,
    wherein the substituents are selected from $C_1$-$C_2$ linear alkyl, $C_3$-$C_{20}$ branched alkyl, $C_3$-$C_{20}$ cyclic alkyl, linear fluorinated $C_1$-$C_{12}$ alkyl, linear $C_1$-$C_{20}$ alkoxy, branched $C_1$-$C_{12}$ fluorinated alkyl, $C_3$-$C_{12}$ cyclic fluorinated alkyl, branched $C_1$-$C_{12}$ fluorinated alkoxy, $C_3$-$C_{12}$ cyclic fluorinated alkoxy, nitrile, OR, SR, (C=O)R, (C=O)$NR_2$, $SiR_3$, (S=O)R, (S=O)$_2$R, (P=O)$R_2$;
R is $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl;
m is selected from 1, 2 or 3, preferably 1.

According to one embodiment, wherein in formula I:
$X^1$ to $X^{20}$ are independently selected from C—H and C—Z, or optional from C—H, C—$R^1$, C—Z;
  wherein at least one $X^1$ to $X^{20}$ is selected from C—$R^1$ or C—Z;
$R^1$ is selected from —$NR^2R^3$ or —$BR^2R^3$;
$R^2$ and $R^3$ are independently selected $C_{6-16}$ aryl or $C_{2-12}$ heteroaryl;
Z is a substituent of formula II:

$$-\!\!+\!Ar^1\!\!+\!\!\!\!\!\!-_n\!\!+\!Ar^2)_m, \quad (II)$$

wherein
$Ar^1$ is a triazine ring;
$Ar^2$ are independently selected from substituted or unsubstituted $C_{12-60}$ aryl or substituted or unsubstituted $C_{10}$-$C_{59}$ heteroaryl,
  wherein the substituents are independently selected from nitrile, di-alkyl phosphine oxide, di-aryl phosphine oxide, $C_2$-$C_{16}$ heteroaryl, fluorinated $C_1$-$C_6$ alkyl or fluorinated $C_1$-$C_6$ alkoxy, OR, SR, (C=O)R, (C=O)$NR_2$, $SiR_3$, (S=O)R, (S=O)$_2$R, (P=O)$R_2$;
R is independently selected from a linear $C_1$-$C_2$ alkyl, linear $C_1$-$C_{20}$ alkoxy, linear $C_1$-$C_{20}$ thioalkyl, a branched $C_3$-$C_{20}$ alkyl, branched $C_3$-$C_{20}$ alkoxy, branched $C_3$-$C_{20}$ thioalkyl, $C_{6-20}$ aryl and $C_3$-$C_{20}$ heteroaryl;
m is selected from 1 or 2, preferably 1.

According to one embodiment, wherein in formula I:
$X^1$ to $X^{20}$ are independently selected from C—H and C—Z,
  wherein at least one $X^1$ to $X^{20}$ is selected from C—Z;
Z is a substituent of formula II:

$$-\!\!+\!Ar^1\!\!+\!\!\!\!\!\!-_n\!\!+\!Ar^2)_m, \quad (II)$$

wherein
$Ar^1$ is a triazine ring;
$Ar^2$ are independently selected from substituted or unsubstituted $C_{12-52}$ aryl and substituted or unsubstituted $C_3$-$C_{51}$ heteroaryl,
  wherein the substituents are independently selected from nitrile, di-alkyl phosphine oxide, di-aryl phosphine oxide, $C_2$-$C_{16}$ heteroaryl, fluorinated $C_1$-$C_6$ alkyl or fluorinated $C_1$-$C_6$ alkoxy, OR, SR, (C=O)R, (C=O)$NR_2$, $SiR_3$, (S=O)R, (S=O)$_2$R, (P=O)$R_2$;
R is independently selected from a linear $C_1$-$C_{10}$ alkyl, linear $C_1$-$C_{10}$ alkoxy, linear $C_1$-$C_{10}$ thioalkyl, a branched $C_3$-$C_{10}$ alkyl, branched $C_3$-$C_{10}$ alkoxy, branched $C_3$-$C_{10}$ thioalkyl, $C_{6-12}$ aryl and $C_3$-$C_{11}$ heteroaryl;
m is selected from 1 or 2, preferably 1.

According to one embodiment, wherein in formula I:
$X^1$ to $X^{20}$ are independently selected from C—H and C—Z,
  wherein one $X^1$ to $X^{20}$ is selected from C—Z;
Z is a substituent of formula II:

$$-\!\!+\!Ar^1\!\!+\!\!\!\!\!\!-_n\!\!+\!Ar^2)_m, \quad (II)$$

wherein
$Ar^1$ is a triazine ring;
$Ar^2$ are independently selected from substituted or unsubstituted $C_{12-52}$ aryl and substituted or unsubstituted $C_3$-$C_{51}$ heteroaryl,
  wherein the substituents are independently selected from nitrile, di-alkyl phosphine oxide, di-aryl phosphine oxide, $C_2$-$C_{16}$ heteroaryl, fluorinated $C_1$-$C_6$ alkyl or fluorinated $C_1$-$C_6$ alkoxy, OR, SR, (C=O)R, (C=O)$NR_2$, $SiR_3$, (S=O)R, (S=O)$_2$R, (P=O)$R_2$;
R is independently selected from a linear $C_1$-$C_{10}$ alkyl, linear $C_1$-$C_{10}$ alkoxy, linear $C_1$-$C_{10}$ thioalkyl, a branched $C_3$-$C_{10}$ alkyl, branched $C_3$-$C_{10}$ alkoxy, branched $C_3$-$C_{10}$ thioalkyl, $C_{6-12}$ aryl and $C_3$-$C_{11}$ heteroaryl;
m is selected from 1 or 2, preferably 1.

According to one embodiment, wherein in formula I:
$X^1$ to $X^{20}$ are independently selected from C—H and C—Z,
  wherein one $X^1$ to $X^{20}$ is selected from C—Z;

Z is a substituent of formula II:

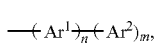
(II)

wherein
Ar$^1$ is a triazine ring,
Ar$^2$ is independently selected from substituted or unsubstituted C$_{12-52}$ aryl and substituted or unsubstituted C$_3$-C$_{51}$ heteroaryl,
wherein the substituents are independently selected from nitrile, di-alkyl phosphine oxide, di-aryl phosphine oxide, C$_2$-C$_{16}$ heteroaryl, fluorinated C$_1$-C$_6$ alkyl or fluorinated C$_1$-C$_6$ alkoxy, OR, SR, (C=O)R, (C=O)NR$_2$, SiR$_3$, (S=O)R, (S=O)$_2$R, (P=O)R$_2$;
R is independently selected from a linear C$_1$-C$_{10}$ alkyl, linear C$_1$-C$_{10}$ alkoxy, linear C$_1$-C$_{10}$ thioalkyl, a branched C$_3$-C$_{10}$ alkyl, branched C$_3$-C$_{10}$ alkoxy, branched C$_3$-C$_{10}$ thioalkyl, C$_{6-12}$ aryl and C$_3$-C$_{11}$ heteroaryl;
m is selected from 1 or 2, preferably 1.
According to one embodiment, wherein in formula I:
X$^1$ to X$^{20}$ are independently selected from C—H and C—Z,
wherein one X$^1$ to X$^{20}$ is selected from C—Z;
Z is a substituent of formula II:

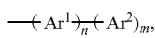
(II)

wherein
Ar$^1$ is a triazine ring,
Ar$^2$ is independently selected from substituted or unsubstituted C$_{12-52}$ aryl and substituted or unsubstituted C$_3$-C$_{51}$ heteroaryl,
wherein the substituents are independently selected from nitrile and (P=O)R$_2$;
R is independently selected from a linear C$_1$-C$_{10}$ alkyl, C$_{6-12}$ aryl and C$_3$-C$_{11}$ heteroaryl;
m is selected from 1 or 2, preferably 1.
According to one embodiment, wherein in formula I:
X$^1$ to X$^{20}$ are independently selected from C—H and C—Z,
wherein one X$^1$ to X$^{20}$ is selected from C—Z;
Z is a substituent of formula II:

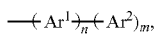
(II)

wherein
Ar$^1$ is a triazine ring,
Ar$^2$ is independently selected from substituted or unsubstituted C$_{12-48}$ aryl and at least one substituted or unsubstituted C$_3$-C$_{17}$ heteroaryl,
wherein the substituents are independently selected from nitrile and (P=O)R$_2$;
R is independently selected from a linear C$_1$-C$_{10}$ alkyl, C$_{6-12}$ aryl and C$_3$-C$_{11}$ heteroaryl;
m is selected from 1 or 2, preferably 1.
According to one embodiment, wherein in formula I:
X$^1$ to X$^{20}$ are independently selected from C—H and C—Z,
wherein one X$^1$ to X$^{20}$ is selected from C—Z;
Z is a substituent of formula II:

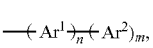
(II)

wherein
Ar$^1$ is a triazine ring,
Ar$^2$ is independently selected from substituted or unsubstituted C$_{12-48}$ aryl and at least one substituted or unsubstituted C$_3$-C$_{17}$ heteroaryl,
wherein the substituents are independently selected from nitrile and (P=O)R$_2$;
R is independently selected from a linear C$_1$-C$_{10}$ alkyl;
m is selected from 1 or 2, preferably 1.
According to one embodiment, wherein the compound of formula I can be:
X$^1$ to X$^{20}$ are independently selected from C—H and C—Z,
wherein one X$^1$ to X$^{20}$ is selected from C—Z;
Z is a substituent of formula II:

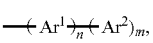
(II)

wherein
Ar$^1$ is a triazine ring,
Ar$^2$ is independently selected from unsubstituted C$_{12-48}$ aryl and at least one unsubstituted C$_3$-C$_{17}$ heteroaryl,
wherein the substituents are independently selected from nitrile and (P=O)R$_2$;
R is independently selected from a linear C$_1$-C$_{10}$ alkyl;
m is selected from 1 or 2, preferably 1.
According to one embodiment of the compound according to formula I, wherein Z may have the formula III:

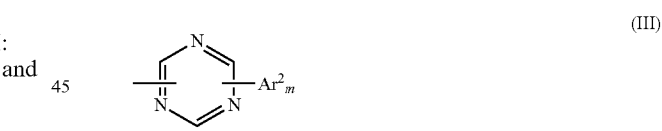
(III)

wherein
Ar$^2$ is independently selected from substituted or unsubstituted C$_{6-60}$ aryl or C$_2$-C$_{60}$ heteroaryl;
wherein
the substituents are independently selected from nitrile, C$_1$-C$_{20}$ di-alkyl phosphine oxide, C$_{6-20}$ di-aryl phosphine oxide, C$_2$-C$_{36}$ heteroaryl, fluorinated C$_1$-C$_6$ alkyl or fluorinated C$_1$-C$_6$ alkoxy, OR, SR, (C=O)R, (C=O)NR$_2$, SiR$_3$, (S=O)R, (S=O)$_2$R, (P=O)R$_2$;
R is independently selected from a linear C$_1$-C$_{20}$ alkyl, linear C$_1$-C$_{20}$ alkoxy, linear C$_1$-C$_{20}$ thioalkyl, a branched C$_3$-C$_{20}$ alkyl, branched C$_3$-C$_{20}$ alkoxy, branched C$_3$-C$_{20}$ thioalkyl, C$_{6-20}$ aryl and C$_3$-C$_{20}$ heteroaryl;
m is selected from 1 or 2, preferably 1.
According to one embodiment of the compound according to formula I, wherein Ar$^2$ can be selected from formula F1 to F16:

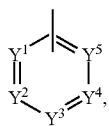
(F1)

wherein
$Y^1$ to $Y^5$ are independently selected from N, OR, SR, (C=O)R, (C=O)NR$_2$, SiR$_3$, (S=O)R, (S=O)$_2$R, (P=O)R$_2$, C—H, C—R, and/or at least two of $Y^1$ to $Y^5$, which are connected to each other by a chemical bond, are bridged to form an anellated aromatic ring or anellated heteroaromatic ring,
wherein R is independently selected from a linear C$_1$-C$_{20}$ alkyl, linear C$_1$-C$_{20}$ alkoxy, linear C$_1$-C$_{20}$ thioalkyl, a branched C$_3$-C$_{20}$ alkyl, branched C$_3$-C$_{20}$ alkoxy, branched C$_3$-C$_{20}$ thioalkyl, C$_{6-20}$ aryl and C$_3$-C$_{20}$ heteroaryl;

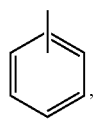
F2

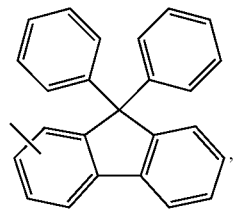
F3

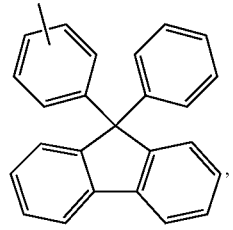
F4

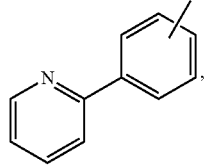
F5

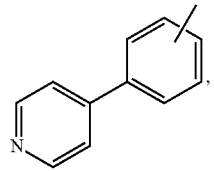
F6

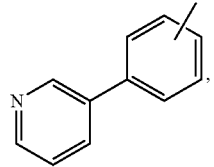
F7

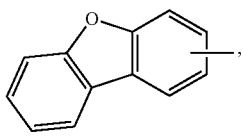
F8

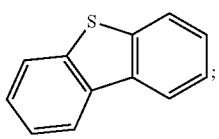
F9

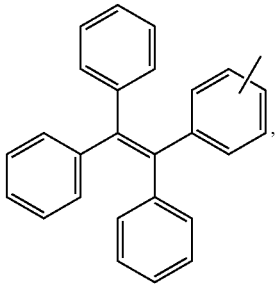
F10

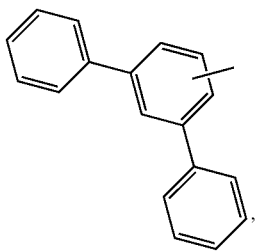
F11

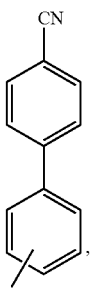
F12

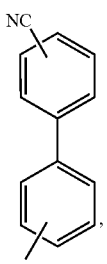
F13

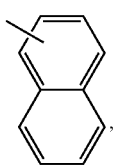
F14

-continued

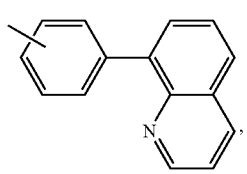

F15

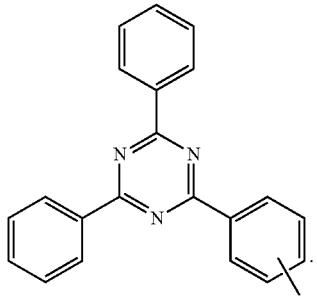

F16

According to one embodiment the compound according to formula I, wherein
- Ar² comprises at least one pyridine, pyrimidine or triazine ring, preferably a triazine ring; and/or
- Ar² comprises at least one substituted or unsubstituted benzothiazole group; and/or
- Ar² comprises at least one nitril and/or phosphine oxide substituent;

or
- Ar² is free of a pyridine, pyrimidine or triazine ring; and/or
- Ar² is free of a substituted or unsubstituted benzothiazole group.

According to one embodiment the compound according to formula I, wherein Ar² may comprises at least one substituted or unsubstituted 1,1,2,2-Tetraphenylethylene group, preferably an unsubstituted 1,1,2,2-Tetraphenylethylene group; which can be:
a) bonded via a single bond to a pyridine, a pyrimidine or a triazine ring, preferably a triazine ring; or
b) bonded via a single bond to a phenyl group, wherein the phenyl group is bonded via a single bond to pyridine, pyrimidine or triazine ring, preferably a triazine ring.

According to one embodiment, wherein the compound of Formula I can be selected from G1 to G28:

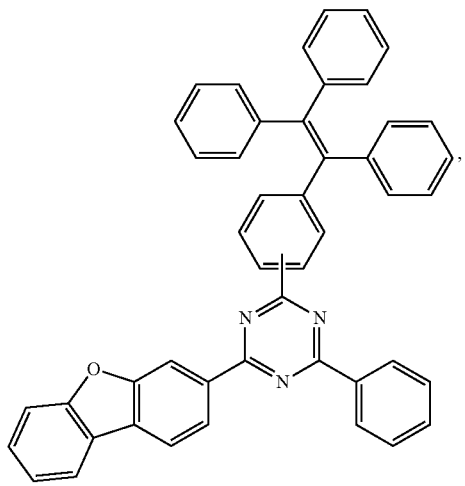

G1

-continued

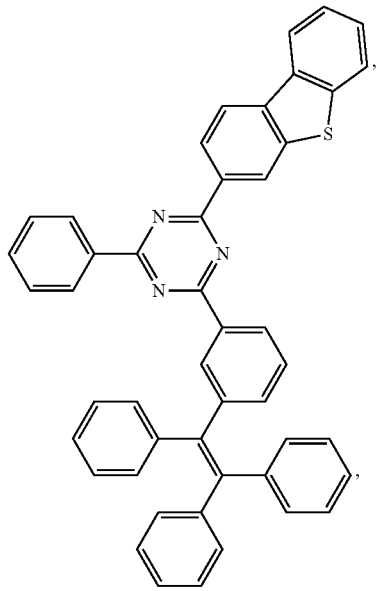

G2

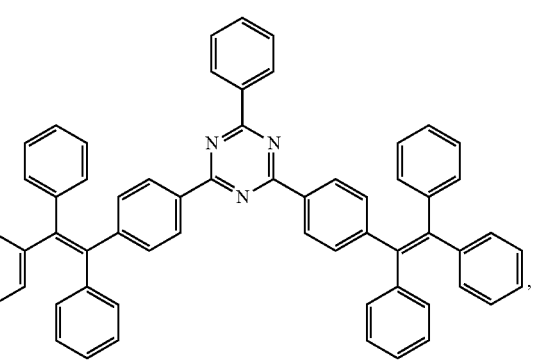

G3

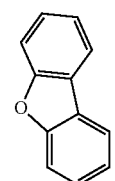

G4

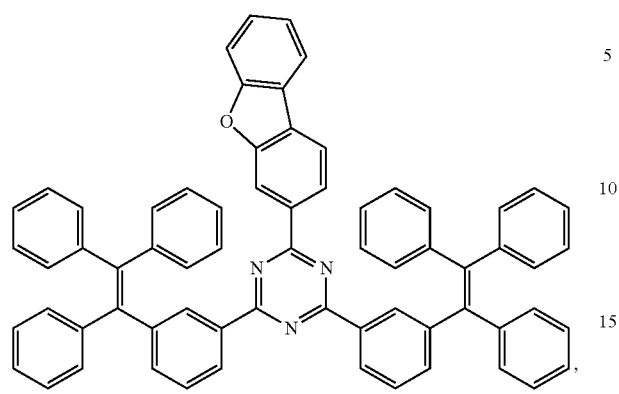
G5
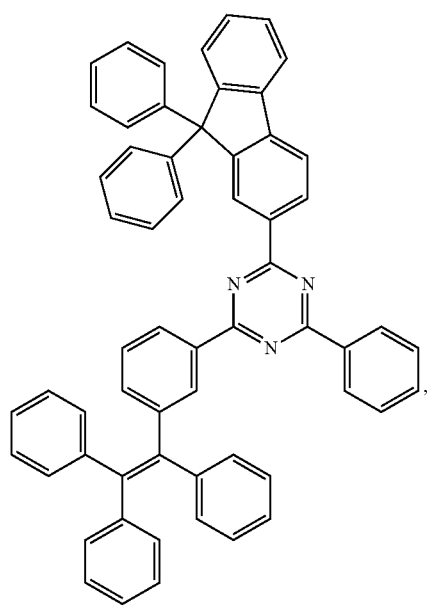
G6
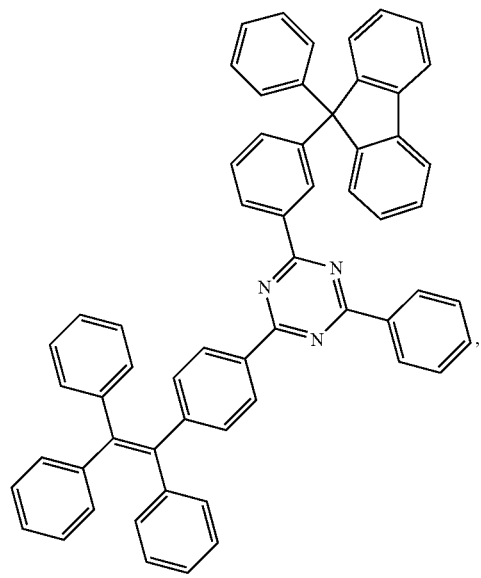
G7
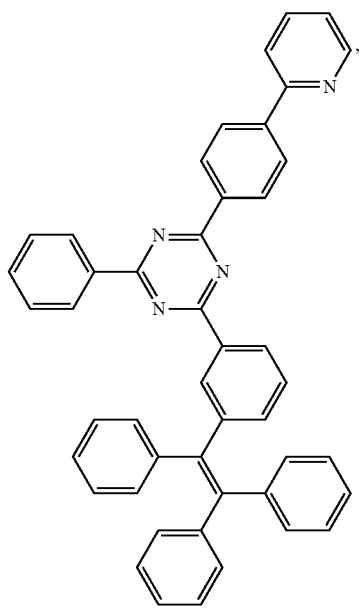
G8
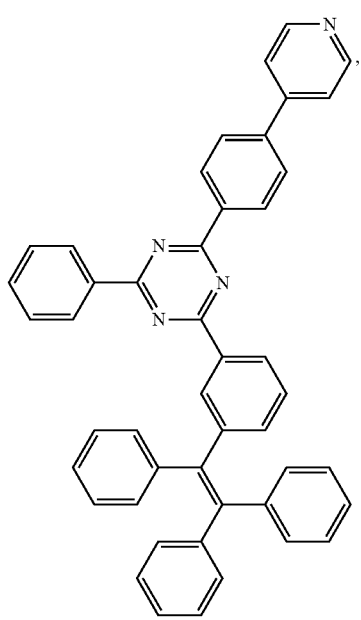
G9

G10
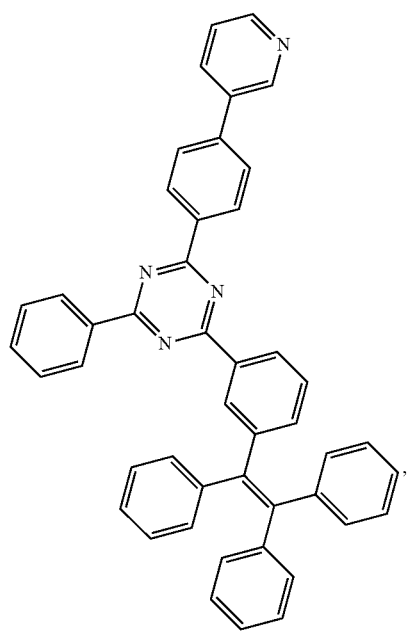
G12
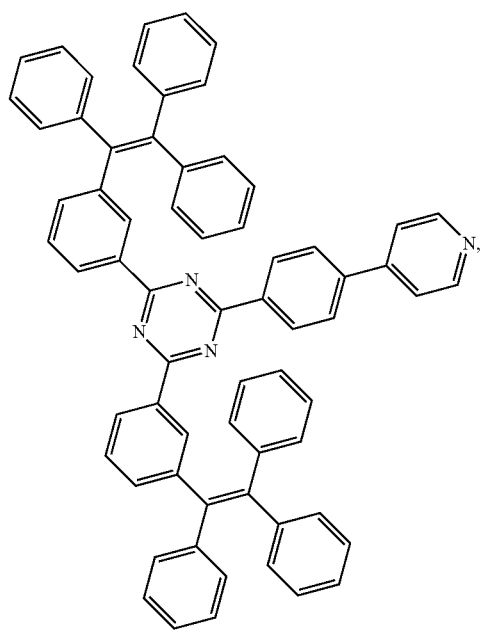
G11
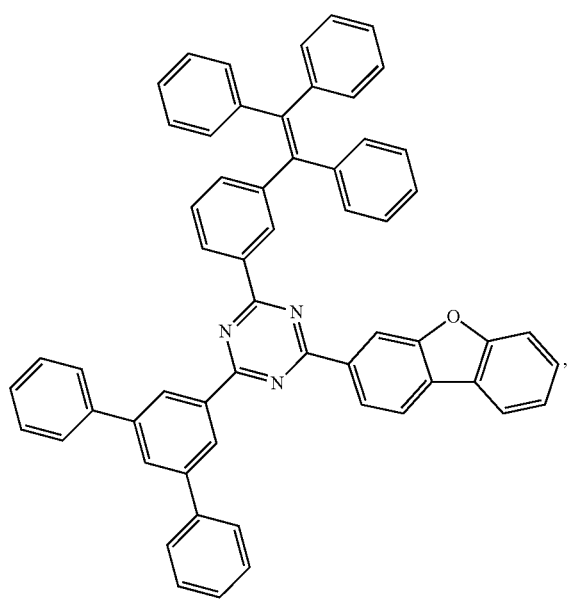
G13
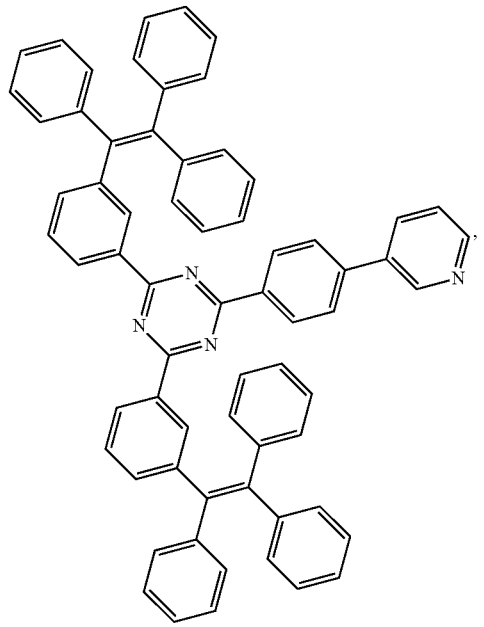

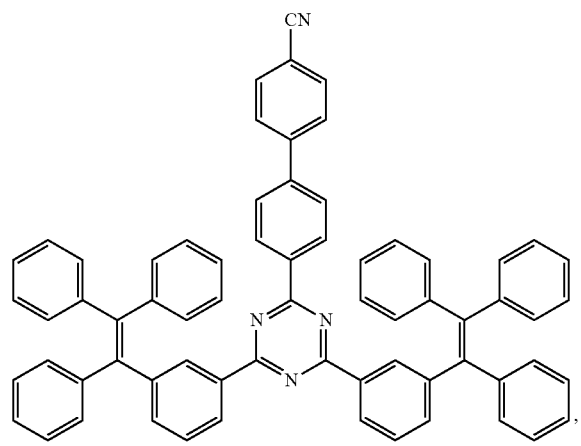
G14
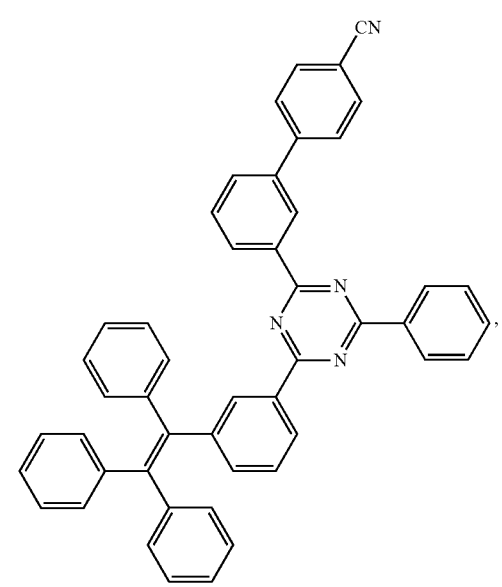
G15
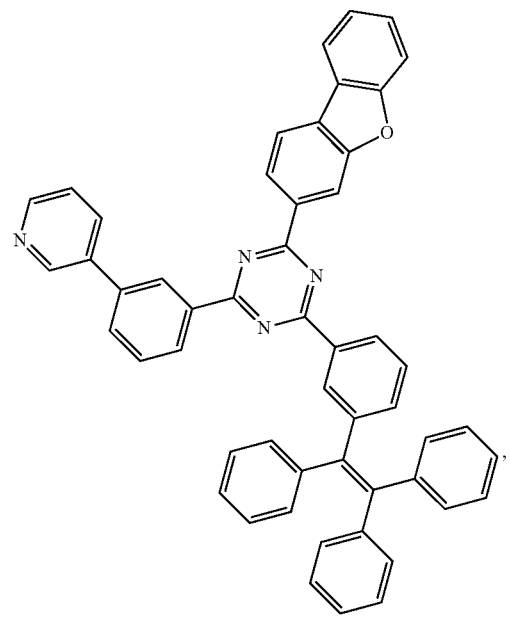
G16
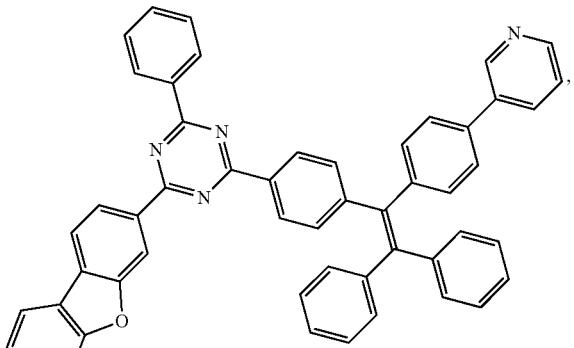
G17
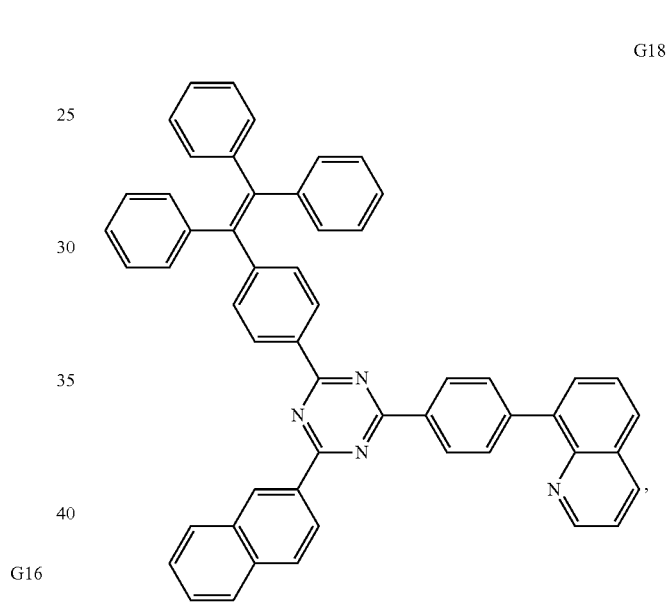
G18, G19

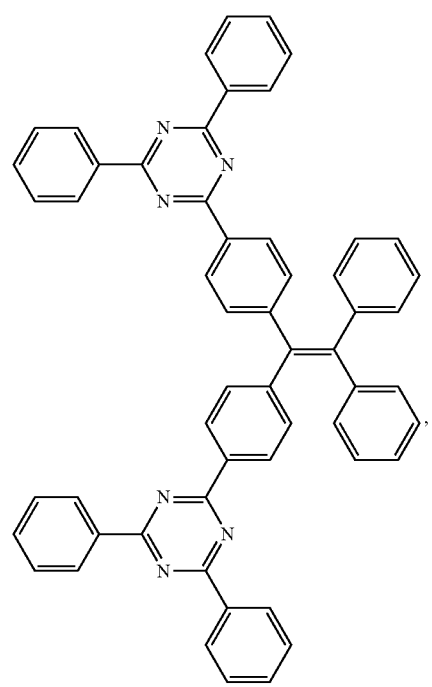
G20
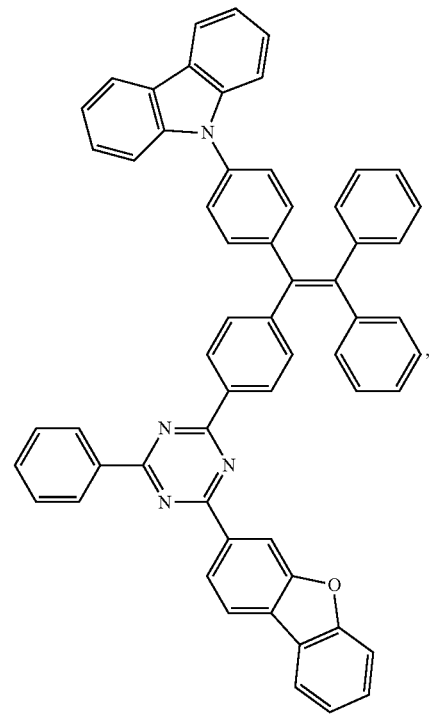
G22
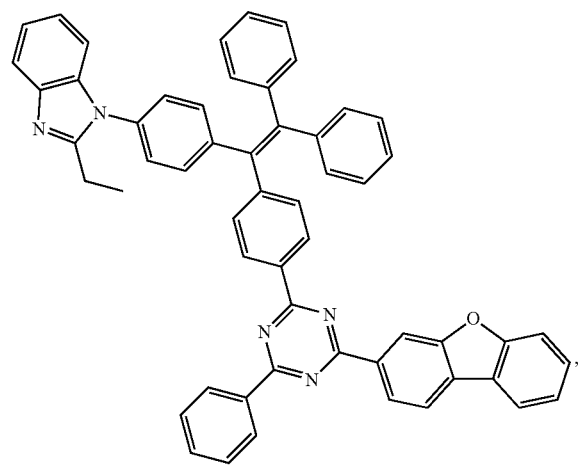
G21
G23

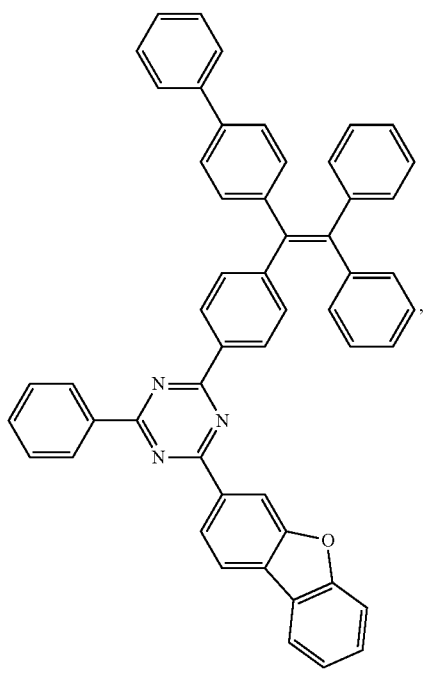 G24
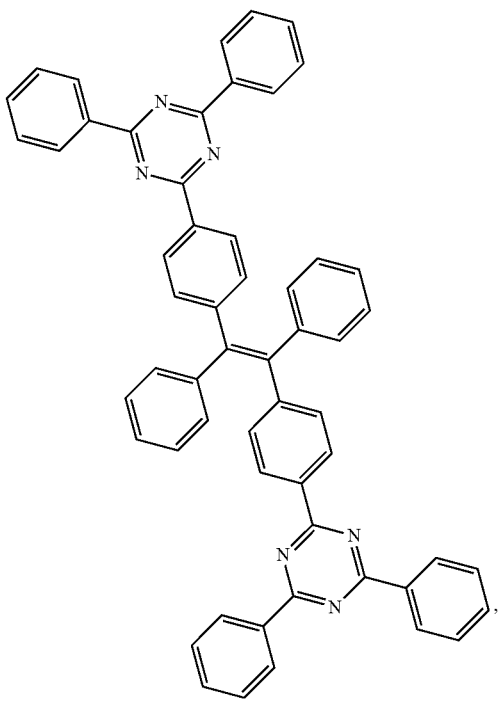 G26
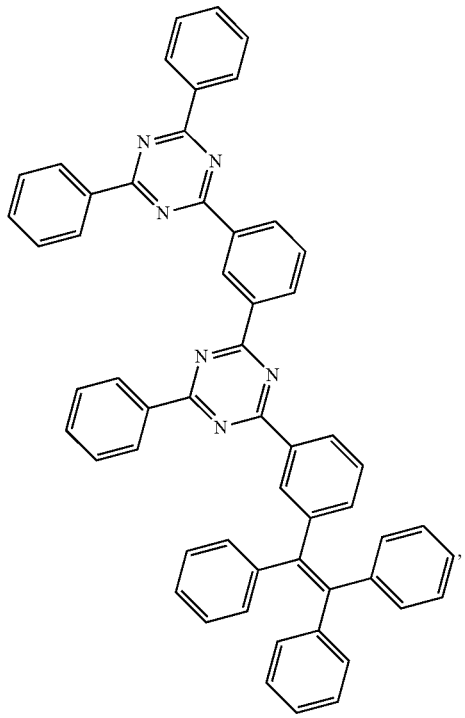 G25
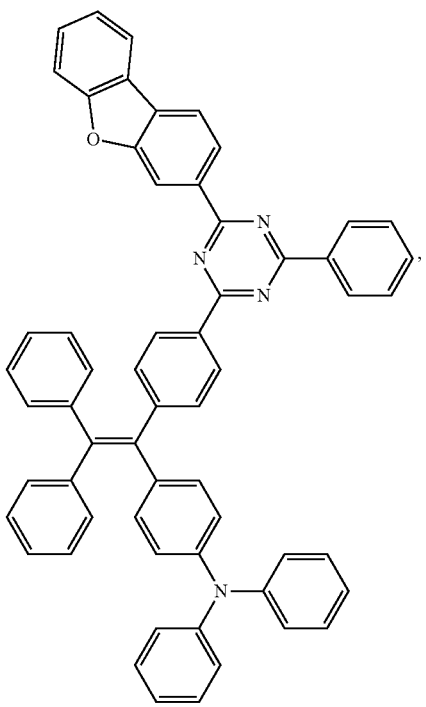 G27

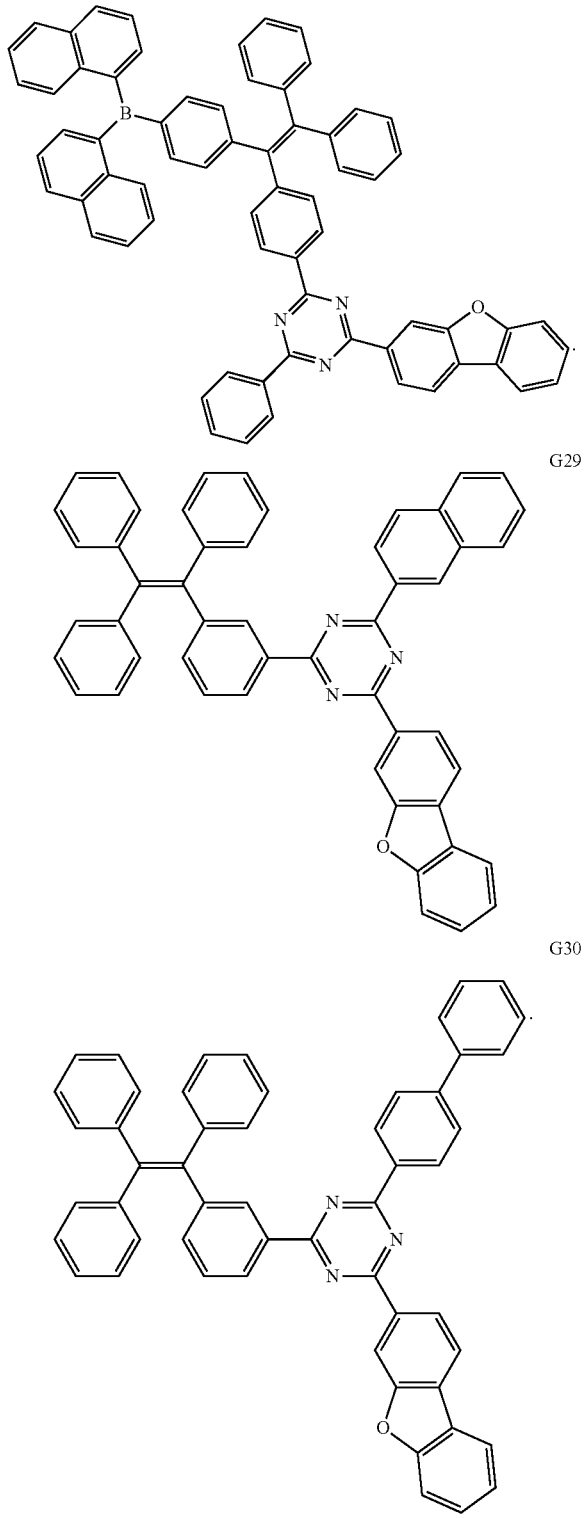

Particularly good performance characteristics are obtained when the compound of formula I is chosen from this selection.

Anode

A material for the anode may be a metal or a metal oxide, or an organic material, preferably a material with work function above about 4.8 eV, more preferably above about 5.1 eV, most preferably above about 5.3 eV. Preferred metals are noble metals like Pt, Au or Ag, preferred metal oxides are transparent metal oxides like ITO or IZO which may be advantageously used in bottom-emitting OLEDs having a reflective cathode.

In devices comprising a transparent metal oxide anode or a reflective metal anode, the anode may have a thickness from about 50 nm to about 100 nm, whereas semitransparent metal anodes may be as thin as from about 5 nm to about 15 nm, and non-transparent metal anodes may have a thickness from about 15 nm to about 150 nm.

Hole Injection Layer (HIL)

The hole injection layer may improve interface properties between the anode and an organic material used for the hole transport layer, and is applied on a non-planarized anode and thus may planarize the surface of the anode. For example, the hole injection layer may include a material having a median value of the energy level of its highest occupied molecular orbital (HOMO) between the work function of the anode material and the energy level of the HOMO of the hole transport layer, in order to adjust a difference between the work function of the anode and the energy level of the HOMO of the hole transport layer.

When the hole transport region comprises a hole injection layer 36, the hole injection layer may be formed on the anode by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-6}$ Pa to about $10^{-1}$ Pa, and a deposition rate of about 0.1 to about 10 nm/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

The hole injection layer may further comprise a p-dopant to improve conductivity and/or hole injection from the anode.

The hole injection layer may comprise a compound of formula I.

In another embodiment the hole injection layer may consist of a compound of formula I.

p-Dopant

In another aspect, the p-dopant may be homogeneously dispersed in the hole injection layer.

In another aspect, the p-dopant may be present in the hole injection layer in a higher concentration closer to the anode and in a lower concentration closer to the cathode.

The p-dopant may be one of a quinone derivative or a radialene compound but not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), 4,4', 4"-((1E,1'E,1"E)-cyclopropane-1,2,3-triylidenetris(cyanomethanylylidene))-tris(2,3,5,6-tetrafluorobenzonitrile).

Hole Transport Layer (HTL)

Conditions for forming the hole transport layer and the electron blocking layer may be defined based on the above-described formation conditions for the hole injection layer.

A thickness of the hole transport part of the charge transport region may be from about 10 nm to about 1000 nm, for example, about 10 nm to about 100 nm. When the hole transport part of the charge transport region comprises the hole injection layer and the hole transport layer, a thickness of the hole injection layer may be from about 10 nm to about 1000 nm, for example about 10 nm to about 100 nm and a thickness of the hole transport layer may be from about 5 nm to about 200 nm, for example about 10 nm to about 150 nm. When the thicknesses of the hole transport part of the charge transport region, the HIL, and the HTL are within these ranges, satisfactory hole transport characteristics may be obtained without a substantial increase in operating voltage.

Hole transport matrix materials used in the hole transport region are not particularly limited. Preferred are covalent compounds comprising a conjugated system of at least 6 delocalized electrons, preferably organic compounds comprising at least one aromatic ring, more preferably organic compounds comprising at least two aromatic rings, even more preferably organic compounds comprising at least three aromatic rings, most preferably organic compounds comprising at least four aromatic rings. Typical examples of hole transport matrix materials which are widely used in hole transport layers are polycyclic aromatic hydrocarbons, triarylene amine compounds and heterocyclic aromatic compounds. Suitable ranges of frontier orbital energy levels of hole transport matrices useful in various layer of the hole transport region are well-known. In terms of the redox potential of the redox couple HTL matrix/cation radical of the HTL matrix, the preferred values (if measured for example by cyclic voltammetry against ferrocene/ferrocenium redox couple as reference) may be in the range 0.0-1.0 V, more preferably in the range 0.2-0.7 V, even more preferably in the range 0.3-0.5 V.

The hole transport layer may comprise a compound of formula I.

In another embodiment the hole transport layer may consist of a compound of formula I.

Buffer Layer

The hole transport part of the charge transport region may further include a buffer layer.

Buffer layer that can be suitable used are disclosed in U.S. Pat. Nos. 6,140,763, 6,614,176 and in US2016/248022.

The buffer layer may compensate for an optical resonance distance of light according to a wavelength of the light emitted from the EML, and thus may increase efficiency. The buffer layer may comprise a compound of formula I.

In another embodiment the buffer layer may consist of a compound of formula I.

Emission Layer (EML)

The emission layer may be formed on the hole transport region by using vacuum deposition, spin coating, casting, LB method, or the like. When the emission layer is formed using vacuum deposition or spin coating, the conditions for deposition and coating may be similar to those for the formation of the hole injection layer, though the conditions for the deposition and coating may vary depending on the material that is used to form the emission layer. The emission layer may include an emitter host (EML host) and an emitter dopant (further only emitter).

Emitter Host

According to another embodiment, the emission layer comprises compound of formula I as emitter host.

The emitter host compound has at least three aromatic rings, which are independently selected from carbocyclic rings and heterocyclic rings.

Other compounds that can be used as the emitter host is an anthracene matrix compound represented by formula 400 below:

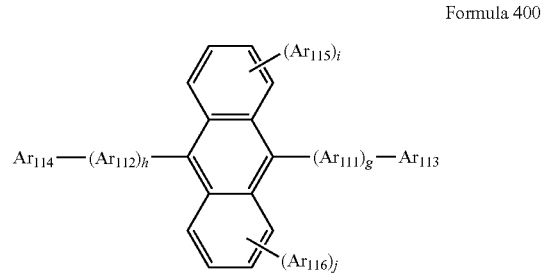

Formula 400

In formula 400, $Ar_{111}$ and $Ar_{112}$ may be each independently a substituted or unsubstituted $C_6$-$C_{60}$ arylene group; $Ar_{113}$ to $Ar_{116}$ may be each independently a substituted or unsubstituted $C_1$-$C_{10}$ alkyl group or a substituted or unsubstituted $C_6$-$C_{60}$ arylene group; and g, h, i, and j may be each independently an integer from 0 to 4.

In some embodiments, $Ar_{111}$ and $Ar_{112}$ in formula 400 may be each independently one of a phenylene group, a naphthalene group, a phenanthrenylene group, or a pyrenylene group; or a phenylene group, a naphthalene group, a phenanthrenylene group, a fluorenyl group, or a pyrenylene group, each substituted with at least one of a phenyl group, a naphthyl group, or an anthryl group.

In formula 400, g, h, i, and j may be each independently an integer of 0, 1, or 2.

In formula 400, $Ar_{113}$ to $Ar_{116}$ may be each independently one of a $C_1$-$C_{10}$ alkyl group substituted with at least one of a phenyl group, a naphthyl group, or an anthryl group;

a phenyl group, a naphthyl group, an anthryl group, a pyrenyl group, a phenanthrenyl group, or a fluorenyl group;

a phenyl group, a naphthyl group, an anthryl group, a pyrenyl group, a phenanthrenyl group, or a fluorenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group

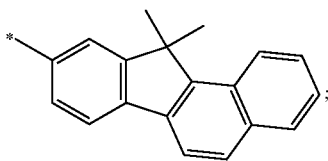 [SMILES: Cc1ccc2c(c1)C(C)(C)c1c-2ccc2ccccc12]

or
formulas 7 or 8

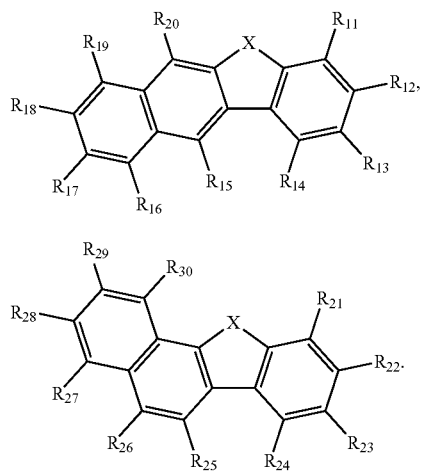

Wherein in the formulas 7 and 8, X is selected form an oxygen atom and a sulfur atom, but embodiments of the invention are not limited thereto.

In the formula 7, any one of $R_{11}$ to $R_{14}$ is used for bonding to $Ar_{111}$. $R_{11}$ to $R_{14}$ that are not used for bonding to $Ar_{11}$ and $R_{15}$ to $R_{20}$ are the same as $R_1$ to $R_8$.

In the formula 8, any one of $R_{21}$ to $R_{24}$ is used for bonding to $Ar_{11}$. $R_{21}$ to $R_{24}$ that are not used for bonding to $Ar_{11}$ and $R_{25}$ to $R_{30}$ are the same as $R_1$ to $R_8$.

Preferably, the EML host comprises between one and three heteroatoms selected from the group consisting of N, O or S. More preferred the EML host comprises one heteroatom selected from S or O.

The emitter host compound may have a dipole moment in the range from about $\geq 0$ Debye to about $\leq 2.0$ Debye.

Preferably, the dipole moment of the EML host is selected $\geq 0.2$ Debye and $\leq 1.45$ Debye, preferably $\geq 0.4$ Debye and $\leq 1.2$ Debye, also preferred $\geq 0.6$ Debye and $\leq 1.1$ Debye.

The dipole moment is calculated using the optimized using the hybrid functional B3LYP with the 6-31G* basis set as implemented in the program package TURBOMOLE V6.5. If more than one conformation is viable, the conformation with the lowest total energy is selected to determine the dipole moment of the molecules. Using this method, 2-(10-phenyl-9-anthracenyl)-benzo[b]naphtho[2,3-d]furan (CAS 1627916-48-6) has a dipole moment of 0.88 Debye, 2-(6-(10-phenylanthracen-9-yl)naphthalen-2-yl)dibenzo[b,d]thiophene (CAS 1838604-62-8) of 0.89 Debye, 2-(6-(10-phenylanthracen-9-yl)naphthalen-2-yl)dibenzo[b,d]furan (CAS 1842354-89-5) of 0.69 Debye, 2-(7-(phenanthren-9-yl)tetraphen-12-yl)dibenzo[b,d]furan (CAS 1965338-95-7) of 0.64 Debye, 4-(4-(7-(naphthalen-1-yl)tetraphen-12-yl)phenyl) dibenzo[b,d] furan (CAS 1965338- of 1.01 Debye.

Emitter Dopant

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The emitter may be a red, green, or blue emitter.

The dopant may be a fluorescent dopant, for example ter-fluorene, the structures are shown below. 4.4'-bis(4-diphenyl amiostyryl)biphenyl (DPAVBI, 2,5,8,11-tetra-tert-butyl perylene (TBPe), and Compound 8 below are examples of fluorescent blue dopants.

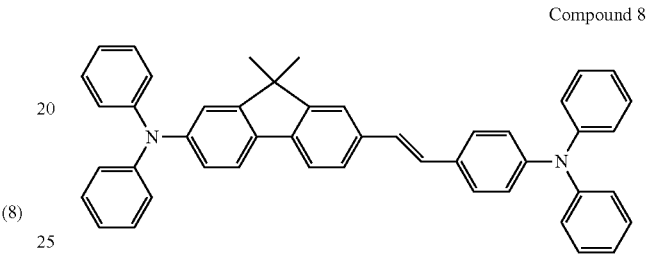

Compound 8

The dopant may be a phosphorescent dopant, and examples of the phosphorescent dopant may be an organic metal compound comprising Ir, Pt, Os, Ti, Zr, Hf, Eu, Tb, Tm, Fe, Co, Ni, Ru, Rh, Pd, or a combination thereof. The phosphorescent dopant may be, for example a compound represented by formula Z, but is not limited thereto:

$$J_2MX \qquad (Z).$$

In formula Z, M is a metal, and J and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the J and X may be, for example a bidendate ligand.

Electron Transport Layer (ETL)

According to another embodiment, the organic semiconductor layer comprising a compound of formula I is an electron transport layer. In another embodiment the electron transport layer may consist of a compound of formula I.

For example, an organic light emitting diode according to an embodiment of the present invention comprises at least one electron transport layer, and in this case, the electron transport layer comprises a compound of formula I, or preferably of at least one compound of formulae G1 to G50.

In another embodiment, the organic electronic device comprises an electron transport region of a stack of organic layers formed by two or more electron transport layers, wherein at least one electron transport layer comprises a compound of formula 1.

The electron transport layer may include one or two or more different electron transport compounds.

According to another embodiment, a second electron transport layer comprises at least one compound of formula 1 according to the invention and a first electron transport layer comprises a matrix compound, which is selected different to the compound of formula 1 according to the invention, and may be selected from:

an anthracene based compound or a hetero substituted anthracene based compound, preferably 2-(4-(9,10-di (naphthalen-2-yl)anthracene-2-yl)phenyl)-1-phenyl- 1H-benzo[d]imidazole and/or N4,N4"-di(naphthalen-1-yl)-N4,N4"-diphenyl-[1,1':4',1"-terphenyl]-4,4"-diamine.

According to another embodiment, a first electron transport layer comprises at least one compound of formula 1 according to the invention and a second electron transport layer comprises a matrix compound, which is selected different to the compound of formula 1 according to the invention, and may be selected from:
- a phosphine oxide based compound, preferably (3-(dibenzo[c,h]acridin-7-yl)phenyl)diphenylphosphine oxide and/or phenyl bis(3-(pyren-1-yl)phenyl)phosphine oxide and/or 3-Phenyl-3H-benzo[b]dinaphtho[2,1-d:1',2'-f]phosphepine-3-oxide; or
- a substituted phenanthroline compound, preferably 2,4,7,9-tetraphenyl-1,10-phenanthroline or 2,9-di(biphenyl-4-yl)-4,7-diphenyl-1,10-phenanthroline.

According to another embodiment a first electron transport layer comprises at least one compound of formula 1 according to the invention and a second electron transport layer comprises a matrix compound, which is selected different to the compound of formula 1 according to the invention, and may be selected from a phosphine oxide based compound, preferably (3-(dibenzo[c,h]acridin-7-yl)phenyl)diphenylphosphine oxide and/or phenyl bis(3-(pyren-1-yl)phenyl)phosphine oxide and/or 3-Phenyl-3H-benzo[b]dinaphtho[2,1-d:1',2'-f]phosphepine-3-oxide.

According to another embodiment, a first and a second electron transport layers comprise a compound of formula 1, wherein the compound of formula 1 is not selected the same.

The thickness of the first electron transport layer may be from about 0.5 nm to about 100 nm, for example about 2 nm to about 40 nm. When the thickness of the first electron transport layer is within these ranges, the first electron transport layer may have improved electron transport ability without a substantial increase in operating voltage.

A thickness of an optional second electron transport layer may be about 1 nm to about 100 nm, for example about 2 nm to about 20 nm. When the thickness of the electron transport layer is within these ranges, the electron transport layer may have satisfactory electron transporting ability without a substantial increase in operating voltage.

The electron transport layer may further comprise an alkali halide and/or alkali organic complex.

According to another embodiment, the first and second electron transport layers comprise a compound of formula 1, wherein the second electron transport layer further comprises an alkali halide and/or alkali organic complex.

Alkali Halide

Alkali halides, also known as alkali metal halides, are the family of inorganic compounds with the chemical formula MX, where M is an alkali metal and X is a halogen.

M can be selected from Li, Na, Potassium, Rubidium and Cesium.

X can be selected from F, Cl, Br and J.

According to various embodiments of the present invention a lithium halide may be preferred. The lithium halide can be selected from the group comprising LiF, LiCl, LiBr and LiJ. However, most preferred is LiF.

The alkali halide is essentially non-emissive or non-emissive.

Alkali Organic Complex

According to various embodiments of the present invention the organic ligand of the lithium organic complex is a quinolate, a borate, a phenolate, a pyridinolate or a Schiff base ligand;

preferably the lithium quinolate complex has the formula III, IV or V:

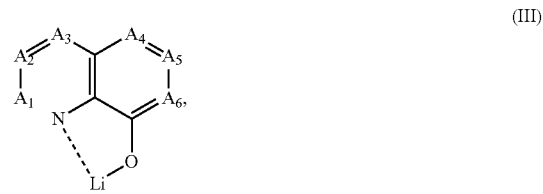

(III)

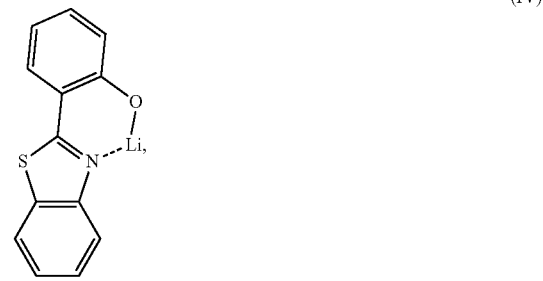

(IV)

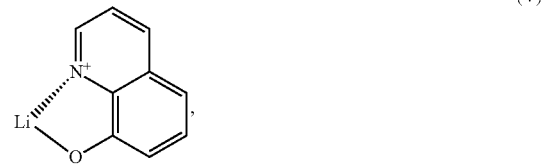

(V)

wherein
$A_1$ to $A_6$ are same or independently selected from CH, CR, N, O;
R is same or independently selected from hydrogen, halogen, alkyl or arylene or heteroarylene with 1 to 20 carbon atoms; and more preferred A1 to A6 are CH;
preferably the borate based organic ligand is a tetra(1H-pyrazol-1-yl)borate;
preferably the phenolate is a 2-(pyridin-2-yl)phenolate, a 2-(diphenylphosphoryl)phenolate, an imidazol phenolates, or 2-(pyridin-2-yl)phenolate and more preferred 2-(1-phenyl-1H-benzo[d]imidazol-2-yl)phenolate;
preferably the pyridinolate is a 2-(diphenylphosphoryl)pyridin-3-olate.

According to various embodiments of the present invention the organic ligand of the alkali organic complex, preferably of a lithium organic complex, can be a quinolate. Quinolates that can be suitable used are disclosed in WO 2013079217 A1 and incorporated by reference.

According to various embodiments of the present invention the organic ligand of the lithium organic complex can be a borate based organic ligand, Preferably the lithium organic complex is a lithium tetra(1H-pyrazol-1-yl)borate. Borate based organic ligands that can be suitable used are disclosed in WO 2013079676 A1 and incorporated by reference.

According to various embodiments of the present invention the organic ligand of the lithium organic complex can be a phenolate ligand, Preferably the lithium organic complex is a lithium 2-(diphenylphosphoryl)phenolate. Phenolate ligands that can be suitable used are disclosed in WO 2013079678 A1 and incorporated by reference.

Further, phenolate ligands can be selected from the group of pyridinolate, preferably 2-(diphenylphosphoryl)pyridin- 3-olate. Pyridine phenolate ligands that can be suitable used are disclosed in JP 2008195623 and incorporated by reference.

In addition, phenolate ligands can be selected from the group of imidazol phenolates, preferably 2-(1-phenyl-1H-benzo[d]imidazol-2-yl)phenolate. Imidazol phenolate ligands that can be suitable used are disclosed in JP 2001291593 and incorporated by reference.

Also, phenolate ligands can be selected from the group of oxazol phenolates, preferably 2-(benzo[d]oxazol-2-yl)phenolate. Oxazol phenolate ligands that can be suitable used are disclosed in US 20030165711 and incorporated by reference.

The alkali organic complex may be essentially non-emissive.

n-Dopant

According to various embodiments, the organic semiconductor layer comprising a compound of formula 1 may further comprise an n-dopant.

Electrically neutral metal complexes suitable as n-dopants may be e.g. strongly reductive complexes of some transition metals in low oxidation state. Particularly strong n-dopants may be selected for example from Cr(II), Mo(II) and/or W(II) guanidinate complexes such as $W_2(hpp)_4$, as described in more detail in WO2005/086251.

Electrically neutral organic radicals suitable as n-dopants may be e.g. organic radicals created by supply of additional energy from their stable dimers, oligomers or polymers, as described in more detail in EP 1 837 926 B1, WO2007/107306, or WO2007/107356. Specific examples of such suitable radicals may be diazolyl radicals, oxazolyl radicals and/or thiazolyl radicals.

In another embodiment, the organic semiconductor layer may further comprise an elemental metal. An elemental metal is a metal in a state of metal in its elemental form, a metal alloy, or a metal cluster. It is understood that metals deposited by vacuum thermal evaporation from a metallic phase, e.g. from a bulk metal, vaporize in their elemental form. It is further understood that if the vaporized elemental metal is deposited together with a covalent matrix, the metal atoms and/or clusters are embedded in the covalent matrix. In other words, it is understood that any metal doped covalent material prepared by vacuum thermal evaporation contains the metal at least partially in its elemental form.

For the use in consumer electronics, only metals containing stable nuclides or nuclides having very long halftime of radioactive decay might be applicable. As an acceptable level of nuclear stability, the nuclear stability of natural potassium can be taken.

In one embodiment, the n-dopant is selected from electropositive metals selected from alkali metals, alkaline earth metals, rare earth metals and metals of the first transition period Ti, V, Cr and Mn. Preferably, the n-dopant is selected from Li, Na, K, Rb, Cs, Mg, Ca, Sr, Ba, Sm, Eu, Tm, Yb; more preferably from Li, Na, K, Rb, Cs, Mg and Yb, even more preferably from Li, Na, Cs and Yb, most preferably from Li, Na and Yb.

The n-dopant may be essentially non-emissive.

Electron Injection Layer (EIL)

According to another aspect of the invention, the organic electroluminescent device may further comprise an electron injection layer between the electron transport layer (first-ETL) and the cathode.

The electron injection layer (EIL) may facilitate injection of electrons from the cathode.

According to another aspect of the invention, the electron injection layer comprises:
(i) an electropositive metal selected from alkali metals, alkaline earth metals and rare earth metals in substantially elemental form, preferably selected from Li, Na, K, Rb, Cs, Mg, Ca, Sr, Ba, Eu and Yb, more preferably from Li, Na, Mg, Ca, Sr and Yb, even more preferably from Li and Yb, most preferably Yb; and/or
(ii) an alkali metal complex and/or alkali metal salt, preferably the Li complex and/or salt, more preferably a Li quinolinolate, even more preferably a lithium 8-hydroxyquinolinolate, most preferably the alkali metal salt and/or complex of the second electron transport layer (second-ETL) is identical with the alkali metal salt and/or complex of the injection layer. The electron injection layer may include at least one selected from LiF, NaCl, CsF, $Li_2O$, and BaO.

A thickness of the EIL may be from about 0.1 nm to about 10 nm, or about 0.3 nm to about 9 nm. When the thickness of the electron injection layer is within these ranges, the electron injection layer may have satisfactory electron injection ability without a substantial increase in operating voltage.

The electron injection layer may comprise a compound of formula 1.

Cathode

A material for the cathode may be a metal, an alloy, or an electrically conductive compound that have a low work function, or a combination thereof. Specific examples of the material for the cathode may be lithium (Li), magnesium (Mg), aluminum (Al), aluminum-lithium (Al—Li), calcium (Ca), magnesium-indium (Mg—In), magnesium-silver (Mg—Ag), silver (Ag) etc. In order to manufacture a top-emission light-emitting device having a reflective anode deposited on a substrate, the cathode may be formed as a light-transmissive electrode from, for example, indium tin oxide (ITO), indium zinc oxide (IZO) or silver (Ag).

In devices comprising a transparent metal oxide cathode or a reflective metal cathode, the cathode may have a thickness from about 50 nm to about 100 nm, whereas semitransparent metal cathodes may be as thin as from about 5 nm to about 15 nm.

A substrate may be further disposed under the anode or on the cathode. The substrate may be a substrate that is used in a general organic light emitting diode and may be a glass substrate or a transparent plastic substrate with strong mechanical strength, thermal stability, transparency, surface smoothness, ease of handling, and water resistance.

The hole injection layer may improve interface properties between ITO as an anode and an organic material used for the hole transport layer, and may be applied on a non-planarized ITO and thus may planarize the surface of the ITO.

The hole injection layer may be formed on the anode by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-8}$ torr to about $10^{-3}$ torr, and a deposition rate of about 0.01 to about 100 Å/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

Conditions for forming the hole transport layer and the electron blocking layer may be defined based on the above-described formation conditions for the hole injection layer.

A thickness of the hole transport region may be from about 100 Å to about 10000 Å, for example, about 100 Å to about 1000 Å. When the hole transport region comprises the hole injection layer and the hole transport layer, a thickness of the hole injection layer may be from about 100 Å to about 10,000 Å, for example about 100 Å to about 1000 Å and a thickness of the hole transport layer may be from about 50 Å to about 2,000 Å, for example about 100 Å to about 1500 Å. When the thicknesses of the hole transport region, the HIL, and the HTL are within these ranges, satisfactory hole transport characteristics may be obtained without a substantial increase in operating voltage.

A thickness of the emission layer may be about 100 Å to about 1000 Å, for example about 200 Å to about 600 Å. When the thickness of the emission layer is within these ranges, the emission layer may have improved emission characteristics without a substantial increase in a operating voltage.

Next, an electron transport region is disposed on the emission layer.

The electron transport region may include at least one of an electron transport layer and an electron injection layer.

The thickness of the electron transport layer may be from about 20 Å to about 1000 Å, for example about 30 Å to about 300 Å. When the thickness of the electron transport layer is within these ranges, the electron transport layer may have improved electron transport auxiliary ability without a substantial increase in operating voltage.

A thickness of the electron transport layer may be about 100 Å to about 1000 Å, for example about 150 Å to about 500 Å. When the thickness of the electron transport layer is within these ranges, the electron transport layer may have satisfactory electron transporting ability without a substantial increase in operating voltage.

In addition, the electron transport region may include an electron injection layer (EIL) that may facilitate injection of electrons from the anode.

The electron injection layer is disposed on an electron transport layer and may play a role of facilitating an electron injection from a cathode and ultimately improving power efficiency and be formed by using any material used in a related art without a particular limit, for example, LiF, Liq, NaCl, CsF, $Li_2O$, BaO, Yb and the like.

The electron injection layer may include at least one selected from LiF, NaCl, CsF, $Li_2O$, and BaO.

A thickness of the EIL may be from about 1 Å to about 100 Å, or about 3 Å to about 90 Å. When the thickness of the electron injection layer is within these ranges, the electron injection layer may have satisfactory electron injection ability without a substantial increase in operating voltage.

A second electrode may be disposed on the organic layer. A material for the second electrode may be a metal, an alloy, or an electrically conductive compound that have a low work function, or a combination thereof. Specific examples of the material for the second electrode may be lithium (Li), magnesium (Mg), aluminum (Al), aluminum-lithium (Al—LI, calcium (Ca), magnesium-indium (Mg—In), magnesium-silver (Mg—Ag), silver (Ag) etc. In order to manufacture a top-emission light-emitting device, the second electrode may be formed as a light-transmissive electrode from, for example, indium tin oxide ITO) or indium zinc oxide IZO). The second electrode may be the cathode.

According to another aspect of the invention, a method of manufacturing an organic electroluminescent device is provided, wherein on an anode electrode the other layers of a hole injection layer, a hole transport layer, optional an electron blocking layer, an emission layer, optional a hole blocking layer, a first electron transport layer, optional an second electron transport layer, an electron injection layer, and a cathode, are deposited in that order; or the layers are deposited the other way around, starting with the cathode.

Hereinafter, the embodiments are illustrated in more detail with reference to examples. However, the present disclosure is not limited to the following examples.

DESCRIPTION OF THE DRAWINGS

These and/or other aspects and advantages of the present invention will become apparent and more readily appreciated from the following description of the exemplary embodiments, taken in conjunction with the accompanying drawings, of which.

Figure 1:
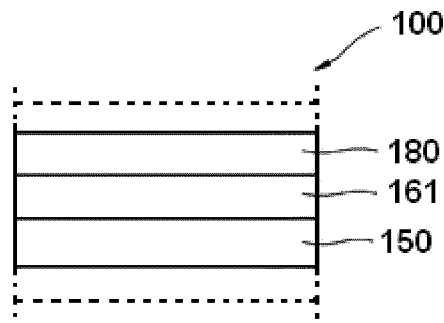
FIG. 1 is a schematic sectional view of an organic light-emitting diode (OLED), according to an exemplary embodiment of the present invention with an emission layer, one electron transport layer and an electron injection layer.

Reference will now be made in detail to the exemplary aspects, examples of which are illustrated in the accompanying drawings, wherein like reference numerals refer to the like elements throughout. The exemplary embodiments are described below, in order to explain the aspects, by referring to the figures.

Herein, when a first element is referred to as being formed or disposed "on" a second element, the first element can be disposed directly on the second element, or one or more other elements may be disposed there between. When a first element is referred to as being formed or disposed "directly on" a second element, no other elements are disposed there between.

The term "contacting sandwiched" refers to an arrangement of three layers whereby the layer in the middle is in direct contact with the two adjacent layers.

The organic light emitting diodes according to an embodiment of the present invention may include a hole transport region; an emission layer; and a first electron transport layer comprising a compound according to formula I.

FIG. 1 is a schematic sectional view of an organic light-emitting diode 100, according to an exemplary embodiment of the present invention. The OLED 100 comprises an emission layer 150, an electron transport layer (ETL) 161 comprising a compound of formula I and an electron injection layer 180, whereby the first electron transport layer 161 is disposed directly on the emission layer 150 and the electron injection layer 180 is disposed directly on the first electron transport layer 161.

Figure 2:
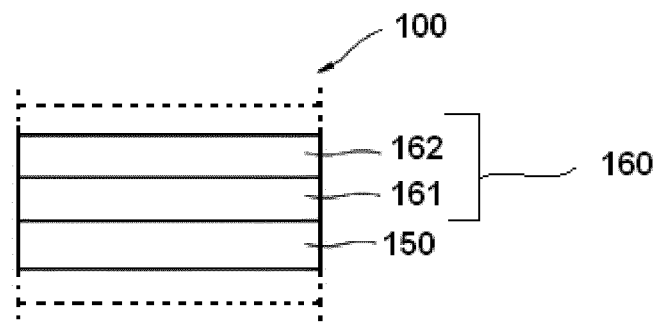
FIG. 2 is a schematic sectional view of an organic light-emitting diode (OLED), according to an exemplary embodiment of the present invention with an emission layer and two electron transport layers.

FIG. 2 is a schematic sectional view of an organic light-emitting diode 100, according to an exemplary embodiment of the present invention. The OLED 100 comprises an emission layer 150 and an electron transport layer stack (ETL) 160 comprising a first electron transport layer 161 comprising a compound of formula I and a second electron transport layer 162, whereby the second electron transport layer 162 is disposed directly on the first electron transport layer 161.

Figure 3:
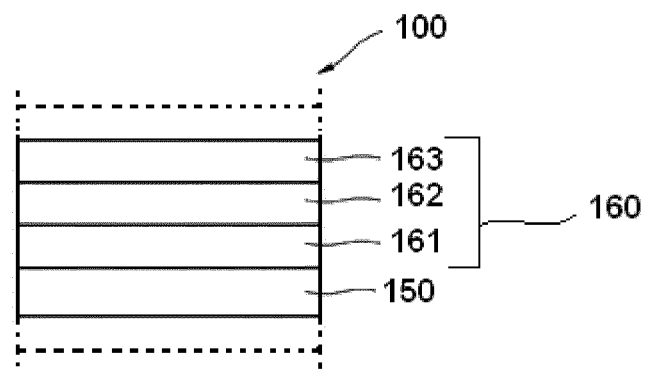
FIG. 3 is a schematic sectional view of an OLED, according to an exemplary embodiment of the present invention with an emission layer and three electron transport layers.

FIG. 3 is a schematic sectional view of an organic light-emitting diode 100, according to an exemplary embodiment of the present invention. The OLED 100 comprises an emission layer 150 and an electron transport layer stack (ETL) 160 comprising a first electron transport layer 161 that comprises a compound of formula I, a second electron transport layer 162 that comprises a compound of formula I but different to the compound of the first electron transport layer, and a third electron transport layer 163, whereby the second electron transport layer 162 is disposed directly on the first electron transport layer 161 and the third electron transport layer 163 is disposed directly on the first electron transport layer 162.

Figure 4:
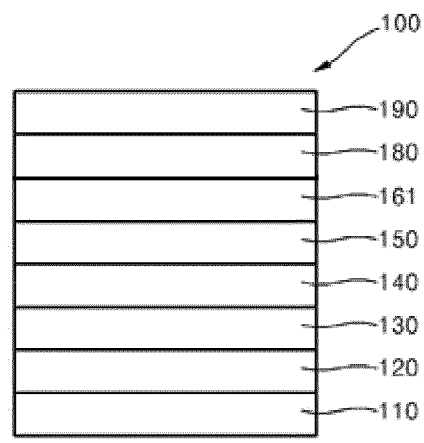
FIG. 4 is a schematic sectional view of an organic light-emitting diode (OLED), according to an exemplary embodiment of the present invention with an emission layer and one electron transport layer.

FIG. 4 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, one first electron transport layer (ETL) 161, an electron injection layer (EIL) 180, and a cathode electrode 190. The first electron transport layer (ETL) 161 comprises a compound of formula I and optionally an alkali halide or alkali organic complex. The electron transport layer (ETL) 161 is formed directly on the EML 150.

Figure 5:
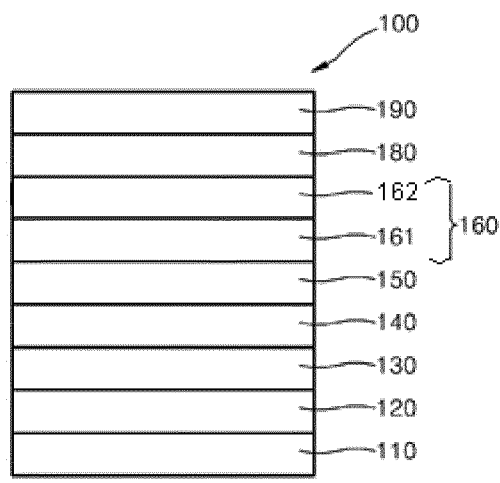
FIG. 5 is a schematic sectional view of an organic light-emitting diode (OLED), according to an exemplary embodiment of the present invention with an emission layer and two electron transport layers.

FIG. 5 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, an electron transport layer stack (ETL) 160, an electron injection layer (EIL) 180, and a cathode electrode 190. The electron transport layer (ETL) 160 comprises a first electron transport layer 161 and a second electron transport layer 162, wherein the first electron transport layer is arranged near to the anode (120) and the second electron transport layer is arranged near to the cathode (190). The first and/or the second electron transport layer comprise a compound of formula I and optionally an alkali halide or alkali organic complex.

Figure 6:
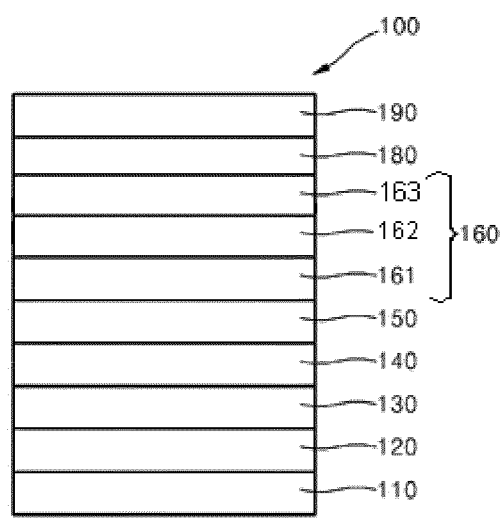
FIG. 6 is a schematic sectional view of an OLED, according to an exemplary embodiment of the present invention with an emission layer and three electron transport layers.

FIG. 6 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, an electron transport layer stack (ETL) 160, an electron injection layer (EIL) 180, and a second cathode electrode 190. The electron transport layer stack (ETL) 160 comprises a first electron transport layer 161, a second electron transport layer 162 and a third electron transport layer 163. The first electron transport layer 161 is formed directly on the emission layer (EML) 150. The first, second and/or third electron transport layer comprise a compound of formula I that is different for each layer, and optionally an alkali halide or alkali organic complex.

A substrate may be further disposed under the anode 120 or on the cathode 190. The substrate may be a substrate that is used in a general organic light emitting diode and may be a glass substrate or a transparent plastic substrate with strong mechanical strength, thermal stability, transparency, surface smoothness, ease of handling, and water resistance.

The hole injection layer 130 may improve interface properties between ITO as an anode and an organic material used for the hole transport layer 140, and may be applied on a non-planarized ITO and thus may planarize the surface of the ITO. For example, the hole injection layer 130 may include a material having particularly desirable conductivity between a work function of ITO and HOMO of the hole transport layer 140, in order to adjust a difference a work function of ITO as an anode and HOMO of the hole transport layer 140.

When the hole transport region comprises a hole injection layer 130, the hole injection layer may be formed on the anode 120 by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-8}$ torr to about $10^{-3}$ torr, and a deposition rate of about 0.01 to about 100 Å/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

Conditions for forming the hole transport layer and the electron blocking layer may be defined based on the above-described formation conditions for the hole injection layer.

A thickness of the hole transport region may be from about 100 Å to about 10000 Å, for example, about 100 Å to about 1000 Å. When the hole transport region comprises the hole injection layer and the hole transport layer, a thickness of the hole injection layer may be from about 100 Å to about 10,000 Å, for example about 100 Å to about 1000 Å and a thickness of the hole transport layer may be from about 50 to about 2,000 Å, for example about 100 Å to about 1500 Å. When the thicknesses of the hole transport region, the HIL, and the HTL are within these ranges, satisfactory hole transport characteristics may be obtained without a substantial increase in operating voltage.

A thickness of the emission layer may be about 100 Å to about 1000 Å, for example about 200 Å to about 600 Å. When the thickness of the emission layer is within these ranges, the emission layer may have improved emission characteristics without a substantial increase in a operating voltage.

Next, an electron transport region is disposed on the emission layer.

The electron transport region may include at least one of a second electron transport layer, a first electron transport layer comprising a compound of formula I, and an electron injection layer.

The thickness of the electron transport layer may be from about 20 Å to about 1000 Å, for example about 30 Å to about 300 Å. When the thickness of the electron transport layer is within these ranges, the electron transport layer may have improved electron transport auxiliary ability without a substantial increase in operating voltage.

A thickness of the electron transport layer may be about 100 Å to about 1000 Å, for example about 150 Å to about 500 Å. When the thickness of the electron transport layer is within these ranges, the electron transport layer may have satisfactory electron transporting ability without a substantial increase in operating voltage.

In addition, the electron transport region may include an electron injection layer (EIL) that may facilitate injection of electrons from the anode.

The electron injection layer is disposed on an electron transport layer and may play a role of facilitating an electron injection from a cathode and ultimately improving power efficiency and be formed by using any material used in a related art without a particular limit, for example, LiF, Liq, NaCl, CsF, $Li_2O$, BaO, Yb and the like.

The electron injection layer may include at least one selected from LiF, NaCl, CsF, $Li_2O$, and BaO.

A thickness of the EIL may be from about 1 Å to about 100 Å, or about 3 Å to about 90 Å. When the thickness of the electron injection layer is within these ranges, the electron injection layer may have satisfactory electron injection ability without a substantial increase in operating voltage.

The anode can be disposed on the organic layer. A material for the anode may be a metal, an alloy, or an electrically conductive compound that have a low work function, or a combination thereof. Specific examples of the material for the anode 120 may be lithium (Li, magnesium (Mg), aluminum (Al), aluminum-lithium (Al—Li, calcium (Ca), magnesium-indium (Mg—In), magnesium-silver (Mg—Ag), silver (Ag) etc. In order to manufacture a top-emission light-emitting device, the anode 120 may be formed as a light-transmissive electrode from, for example, indium tin oxide ITO) or indium zinc oxide IZO).

According to another aspect of the invention, a method of manufacturing an organic electroluminescent device is provided, wherein
- on an anode electrode (120) the other layers of hole injection layer (130), hole transport layer (140), optional an electron blocking layer, an emission layer (130), first electron transport layer (161) comprising a compound of formula I, second electron transport layer (162), electron injection layer (180), and a cathode (190), are deposited in that order; or
- the layers are deposited the other way around, starting with the cathode (190).

Organic Semiconductor Layer

The organic electronic device according to the present invention may comprise an organic semiconductor layer, wherein at least one organic semiconductor layer comprises a compound of formula I.

The organic semiconductor layer of the organic electronic device according to the invention is essentially non-emissive or non-emitting.

The organic semiconductor layer can be an electron transport layer, a hole injection layer, a hole transport layer, an emission layer, an electron blocking layer, a hole blocking layer or an electron injection layer, preferably an electron transport layer or an emission layer, more preferred an electron transport layer.

According to one embodiment, the organic semiconductor layer can be arranged between a photoactive layer and a cathode layer, preferably between an emission layer or light-absorbing layer and the cathode layer, preferably the organic semiconductor layer is an electron transport layer.

According to one embodiment, the organic semiconductor layer may comprise at least one alkali halide or alkali organic complex.

Organic Electronic Device

An organic electronic device according to the invention comprises an organic semiconductor layer comprising a compound according to formula I.

An organic electronic device according to one embodiment may include a substrate, an anode layer, an organic semiconductor layer comprising a compound of formula 1 and a cathode layer.

An organic electronic device according to one embodiment comprises at least one organic semiconductor layer comprising at least one compound of formula I, at least one anode layer, at least one cathode layer and at least one emission layer, wherein the organic semiconductor layer is preferably arranged between the emission layer and the cathode layer.

An organic light-emitting diode (OLED) according to the invention may include an anode, a hole transport layer (HTL), an emission layer (EML), an electron transport layer (ETL) comprising at least one compound of formula 1, and a cathode, which are sequentially stacked on a substrate. In this regard, the HTL, the EML, and the ETL are thin films formed from organic compounds.

An organic electronic device according to one embodiment can be a light emitting device, thin film transistor, a battery, a display device or a photovoltaic cell, and preferably a light emitting device.

According to one embodiment the OLED may have the following layer structure, wherein the layers having the following order:
- an anode layer, a hole injection layer, optional a first hole transport layer, optional a second hole transport layer, an emission layer, an electron transport layer comprising a compound of formula 1 according to the invention, an electron injection layer, and a cathode layer.

According to another aspect of the present invention, there is provided a method of manufacturing an organic electronic device, the method using:

at least one deposition source, preferably two deposition sources and more preferred at least three deposition sources.

The methods for deposition that can be suitable comprise: deposition via vacuum thermal evaporation;

deposition via solution processing, preferably the processing is selected from spin-coating, printing, casting; and/or slot-die coating.

According to various embodiments of the present invention, there is provided a method using:

a first deposition source to release the compound of formula 1 according to the invention, and a second deposition source to release the alkali halide or alkali organic complex, preferably a lithium halide or lithium organic complex;

the method comprising the steps of forming the electron transport layer stack; whereby for an organic light-emitting diode (OLED):

the first electron transport layer is formed by releasing the compound of formula 1 according to the invention from the first deposition source and the alkali halide or alkali organic complex, preferably a lithium halide or lithium organic complex from the second deposition source.

According to various embodiments of the present invention, the method may further include forming on the anode electrode an emission layer and at least one layer selected from the group consisting of forming a hole injection layer, forming a hole transport layer, or forming a hole blocking layer, between the anode electrode and the first electron transport layer.

According to various embodiments of the present invention, the method may further include the steps for forming an organic light-emitting diode (OLED), wherein on a substrate a first anode electrode is formed, on the first anode electrode an emission layer is formed, on the emission layer an electron transport layer stack is formed, preferably a first electron transport layer is formed on the emission layer and optional a second electron transport layer is formed, and finally a cathode electrode is formed, optional a hole injection layer, a hole transport layer, and a hole blocking layer, formed in that order between the first anode electrode and the emission layer, optional an electron injection layer is formed between the electron transport layer and the cathode electrode.

According to various embodiments of the present invention, the method may further include forming an electron injection layer on a first electron transport layer. However, according to various embodiments of the OLED of the present invention, the OLED may not comprise an electron injection layer.

According to various embodiments, the OLED may have the following layer structure, wherein the layers having the following order:

an anode, first hole transport layer, second hole transport layer, emission layer, optional second electron transport layer, first electron transport layer comprising a compound of formula 1 according to the invention, optional an electron injection layer, and a cathode.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

Hereinafter, the embodiments are illustrated in more detail with reference to examples.

However, the present disclosure is not limited to the following examples. Reference will now be made in detail to the exemplary aspects.

Preparation of Compounds of Formula I

Compound of formula I may be prepared as described below and disclosed by Huang et al Chemical Communications (Cambridge, United Kingdom) (2012), 48(77), 9586-9588.

General procedure for Suzuki coupling:

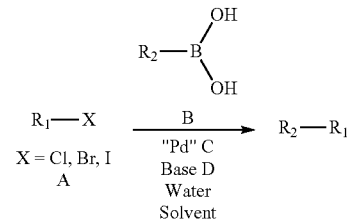

Setup is brought under inert atmosphere. Flask is charged with A, B, C, and D in a counter flow of nitrogen. Water (dist.) is degassed for ~30 min with N2 (under stirring). Solvent mixture is added and the mixture is heated with stirring. (TLC control.).

Synthesis of Compounds of Formula I

Synthesis of 2-(dibenzo[b,d]thiophen-3-yl)-4-phenyl-6-(3-(1,2,2-triphenylvinyl)phenyl)-1,3,5-triazine

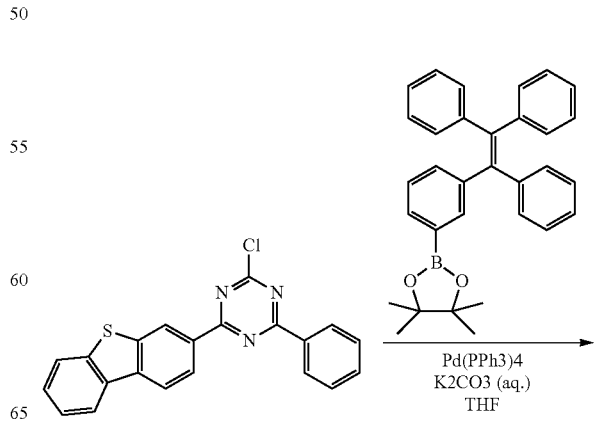

-continued

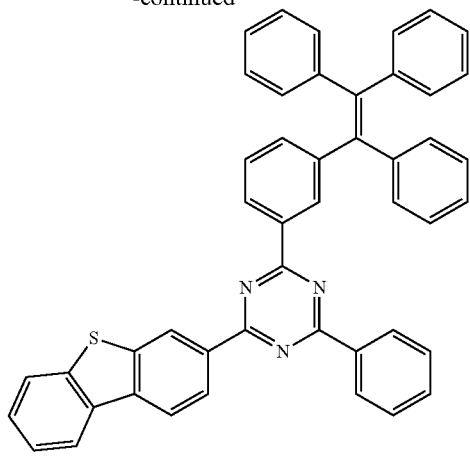

Reagents and reaction conditions: 2-chloro-4-(dibenzo[b,d]thiophen-3-yl)-6-phenyl-1,3,5-triazine (1.0 eq.), 4,4,5,5-tetramethyl-2-(3-(1,2,2-triphenylvinyl)phenyl)-1,3,2-dioxaborolane (1.2 eq.), tetrakistriphenylphosphine palladium (0) (Pd(PPh$_3$)$_4$) (0.02 eq.), potassium carbonate (2.0 eq.). 21 h at 75° C. (210 mL, THF/H$_2$O 2/1).

When the reaction was completed according TLC, it was cooled down to 5° C. Precipitate was filtered, dissolved in dichloromethane and washed with water. Organic phase was filtered over a pad of florisil and then concentrated. With the addition of hexane, precipitate was formed, filtered and further recrystallized in toluene. 15.6 g (69% yield). MS (ESI): 670 (M+H).

Synthesis of 2-(dibenzo[b,d]furan-3-yl)-4-phenyl-6-(4-(1,2,2-triphenylvinyl)phenyl)-1,3,5-triazine

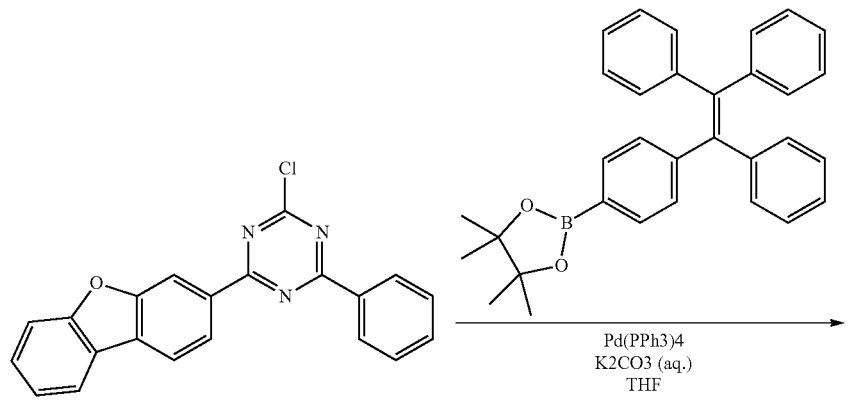

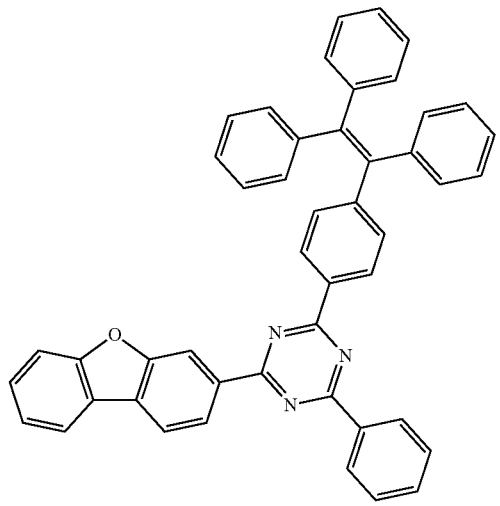

Reagents and reaction conditions: 2-chloro-4-(dibenzo[b,d]furan-3-yl)-6-phenyl-1,3,5-triazine (1.0 eq.), 4,4,5,5-tetramethyl-2-(4-(1,2,2-triphenylvinyl)phenyl)-1,3,2-dioxaborolane (1.2 eq.), tetrakistriphenylphosphine palladium (0) (Pd(PPh$_3$)$_4$) (0.02 eq.), potassium carbonate (2.0 eq.). 66 h at 75° C. (180 mL, THF/H$_2$O 2/1).

When the reaction was completed according TLC, it was cooled down to 5° C. Precipitate was filtered, dissolved in dichloromethane and washed with water. Organic phase was filtered over a pad of florisil and then concentrated. With the addition of hexane, some precipitate was formed, filtered and further recrystallized in toluene. 16.0 g (87% yield). MS (ESI): 654 (M+H).

Synthesis of 2-(dibenzo[b,d]furan-3-yl)-4-phenyl-6-(3-(1,2,2-triphenylvinyl)phenyl)-1,3,5-triazine

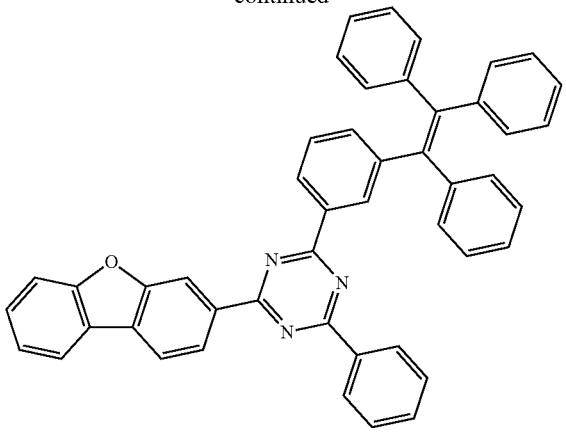

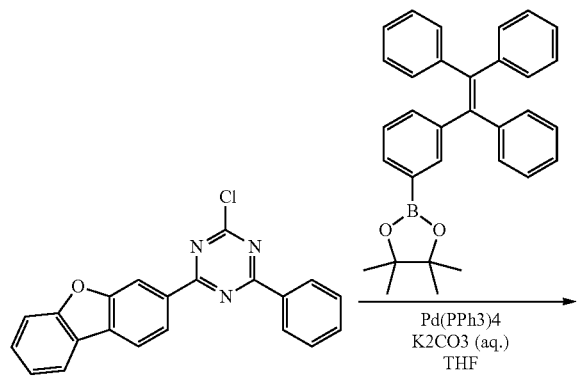

Reagents and reaction conditions: 2-chloro-4-(dibenzo[b,d]furan-3-yl)-6-phenyl-1,3,5-triazine (1.0 eq.), 4,4,5,5-tetramethyl-2-(3-(1,2,2-triphenylvinyl)phenyl)-1,3,2-dioxaborolane (1.2 eq.), tetrakistriphenylphosphine palladium (0) (Pd(PPh$_3$)$_4$) (0.02 eq.), potassium carbonate (2.0 eq.). 21 h at 90° C. (150 mL, THF/H$_2$O 2/1).

When the reaction was completed according TLC, precipitate was filtered, washed with water and methanol, and triturated in methanol. Then, the solid was dissolved in hot chloroform and filtered over a pad of silicagel. Solvent was evaporated. Solid was then triturated in hexane. 15.3 g (84% yield). MS (ESI): 670 (M+H).

Synthesis of 2,4-di(naphthalen-2-yl)-6-(4-(1,2,2-triphenylvinyl)phenyl)-1,3,5-triazine

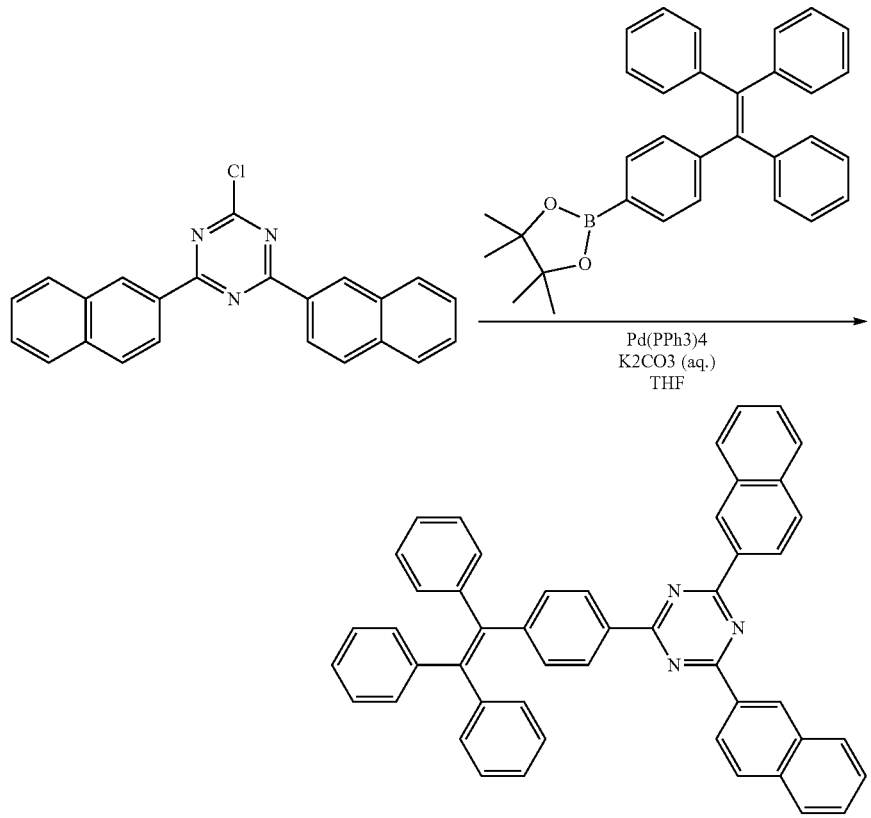

Reagents and reaction conditions: 2-chloro-4,6-di(naphthalen-2-yl)-1,3,5-triazine (1.0 eq.), 4,4,5,5-tetramethyl-2-(4-(1,2,2-triphenylvinyl)phenyl)-1,3,2-dioxaborolane (1.2 eq.), tetrakistriphenylphosphine palladium (0) (Pd(PPh$_3$)$_4$) (0.02 eq.), potassium carbonate (2.0 eq.). 64 h at 75° C. (180 mL, THF/H$_2$O 2/1).

When the reaction was completed according TLC, it was cooled down to 5° C. Precipitate was filtered, dissolved in chloroform and washed with water. Organic phase was filtered over a pad of florisil and then concentrated. With the addition of hexane, some precipitate was formed, filtered and further triturated in toluene. 16.3 g (90% yield). MS (ESI): 664 (M+H).

Synthesis of 2-([1,1'-biphenyl]-2-yl)-4-(dibenzo[b,d]furan-3-yl)-6-(3-(1,2,2-triphenyl-vinyl)phenyl)-1,3,5-triazine

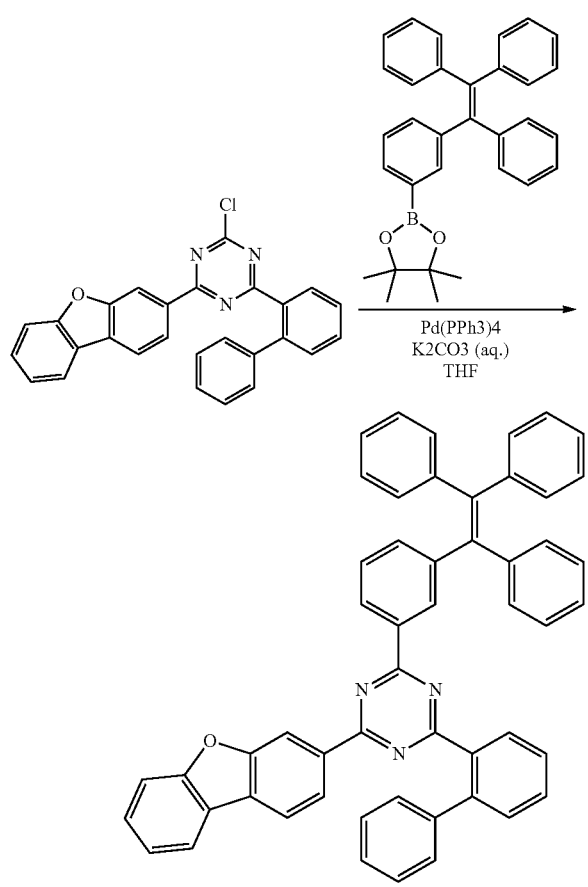

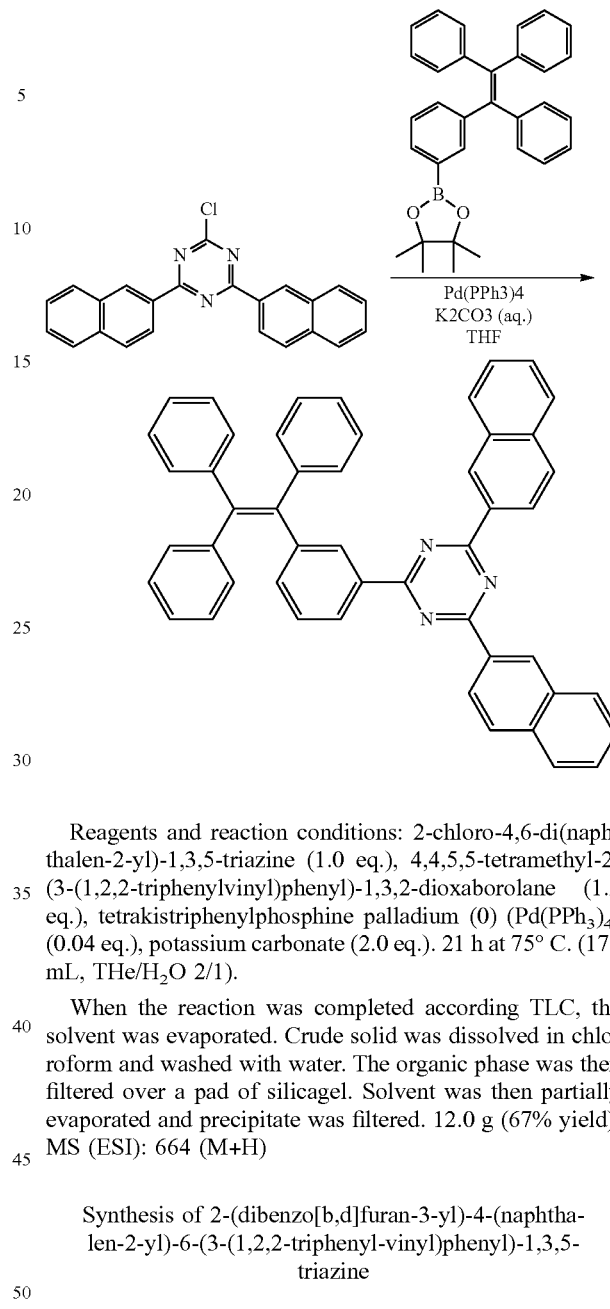

Reagents and reaction conditions: 2-chloro-4,6-di(naphthalen-2-yl)-1,3,5-triazine (1.0 eq.), 4,4,5,5-tetramethyl-2-(3-(1,2,2-triphenylvinyl)phenyl)-1,3,2-dioxaborolane (1.2 eq.), tetrakistriphenylphosphine palladium (0) (Pd(PPh$_3$)$_4$) (0.04 eq.), potassium carbonate (2.0 eq.). 21 h at 75° C. (175 mL, THe/H$_2$O 2/1).

When the reaction was completed according TLC, the solvent was evaporated. Crude solid was dissolved in chloroform and washed with water. The organic phase was then filtered over a pad of silicagel. Solvent was then partially evaporated and precipitate was filtered. 12.0 g (67% yield). MS (ESI): 664 (M+H)

Synthesis of 2-(dibenzo[b,d]furan-3-yl)-4-(naphthalen-2-yl)-6-(3-(1,2,2-triphenyl-vinyl)phenyl)-1,3,5-triazine Reagents and reaction conditions: 2-([1,1'-biphenyl]-2-yl)-4-chloro-6-(dibenzo[b,d]furan-3-yl)-1,3,5-triazine (1.0 eq.), 4,4,5,5-tetramethyl-2-(3-(1,2,2-triphenylvinyl)phenyl)-1,3,2-dioxaborolane (1.2 eq.), tetrakistriphenylphosphine palladium (0) (Pd(PPh$_3$)$_4$) (0.02 eq.), potassium carbonate (2.0 eq.). 21 h at 75° C. (75 mL, THF/H$_2$O 2/1).

When the reaction was completed according TLC, the solvent was evaporated. The crude solid was dissolved in chloroform and washed with water. Organic phase was filtered over a pad of florisil, and the solvent was evaporated. Solid was dissolved in dichloromethane and Synthesis of 2,4-di(naphthalen-2-yl)-6-(3-(1,2,2-triphenylvinyl)phenyl)-1,3,5-triazine

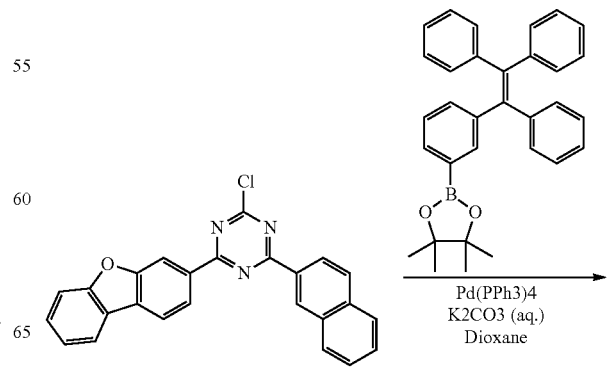

-continued

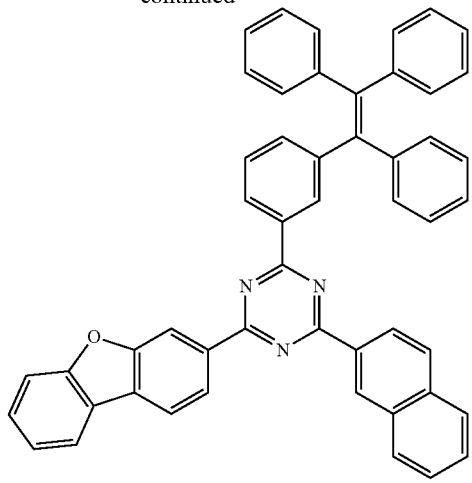

Reagents and reaction conditions: 2-chloro-4-(dibenzo[b,d]furan-3-yl)-6-(naphthalen-2-yl)-1,3,5-triazine (1.0 eq.) 4,4,5,5-tetramethyl-2-(3-(1,2,2-triphenylvinyl)phenyl)-1,3,2-dioxaborolane (1.2 eq.), tetrakistriphenylphosphine palladium (0) (Pd(PPh$_3$)$_4$) (0.02 eq.), potassium carbonate (2.0 eq.). 17 h at 90° C. (160 mL, dioxane/H$_2$O 4/1).

When the reaction was completed according TLC, it was cooled down to 5° C. Precipitate was filtered and washed with water. Then, it was dissolved in dichloromethane and filtered over a pad of florisil and the solvent was evaporated. The solid was recrystallized in o-xylene. 3.5 g (20% yield). MS (ESI): 704 (M+H).

Synthesis of 2-([1,1'-biphenyl]-4-yl)-4-(dibenzo[b,d]furan-3-yl)-6-(3-(1,2,2-triphenyl-vinyl)phenyl)-1,3,5-triazine

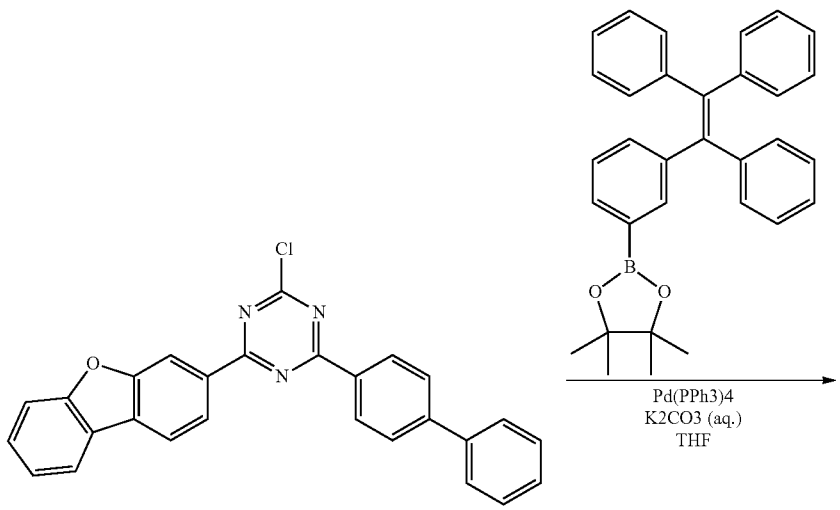

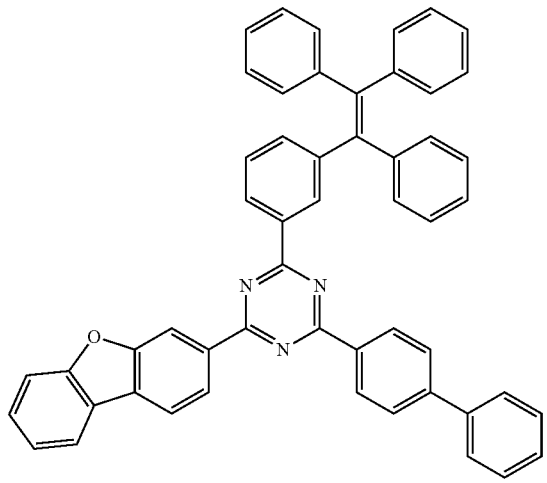

Reagents and reaction conditions: 2-([1,1'-biphenyl]-4-yl)-4-chloro-6-(dibenzo[b,d]furan-3-yl)-1,3,5-triazine (1.0 eq.), 4,4,5,5-tetramethyl-2-(3-(1,2,2-triphenylvinyl)phenyl)-1,3,2-dioxaborolane (1.2 eq.), tetrakistriphenylphosphine palladium (0) (Pd(PPh$_3$)$_4$) (0.02 eq.), potassium carbonate (2.0 eq.). 24 h at 75° C. (125 mL, THF/H$_2$O 4/1).

When the reaction was completed according TLC, reaction was cooled down to room temperature and precipitate was filtered, dissolved in chloroform and washed with water. Organic phase was filtered over a pad of florisil and solvent was then evaporated. 9.6 g (78% yield). MS (ESI): 730 (M+H).

Synthesis of 2-phenyl-4-(4-(pyridin-2-yl)phenyl)-6-(3-(1,2,2-triphenylvinyl)phenyl)-1,3,5-triazine

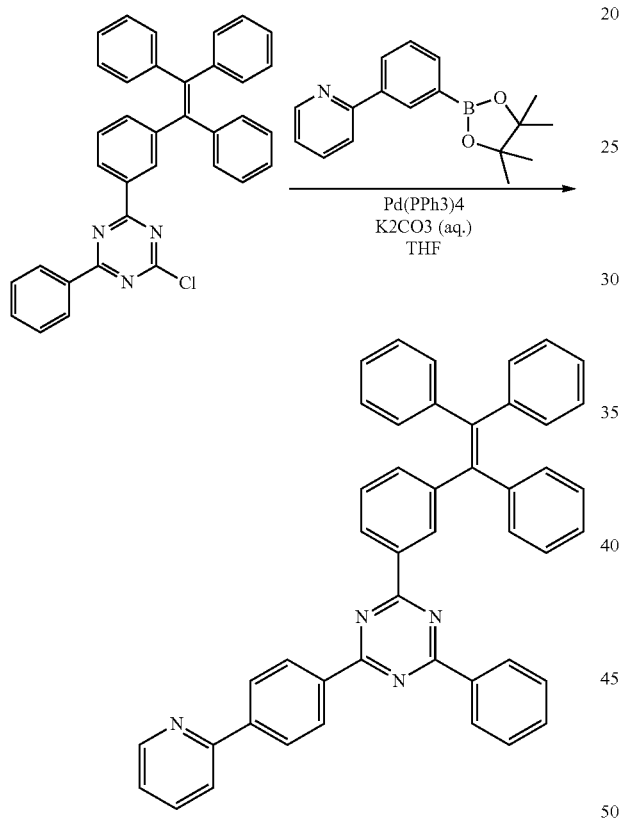

Reagents and reaction conditions: 2-chloro-4-phenyl-6-(3-(1,2,2-triphenylvinyl)phenyl)-1,3,5-triazine (1.0 eq.), 2-(3-(4,4,5,5-tetramethyl-1,3,2-dioxaborolan-2-yl)phenyl)pyridine (1.2 eq.), tetrakistriphenylphosphine palladium (0) (Pd(PPh$_3$)$_4$) (0.02 eq.), potassium carbonate (2.0 eq.). 21 h at 75° C. (90 mL, THF/H$_2$O 2/1).

When the reaction was completed according TLC, the solvent was evaporated. The crude mixture was dissolved in dichloromethane and washed with water. Organic phase was filtered over a pad of Florisil, and the solvent was evaporated. The crude solid was purified by column chromatography (hexane/dichloromethane 3/1 to hexane/dichloromethane 2/1). The solid collected was dissolved in dochloromethane and precipitated upon addition of methanol. 6.2 g (46% yield). MS (ESI): 640 (M+H).

Synthesis of 2-(9,9-diphenyl-9H-fluoren-2-yl)-4-phenyl-6-(3-(1,2,2-triphenylvinyl)phenyl)-1,3,5-triazine

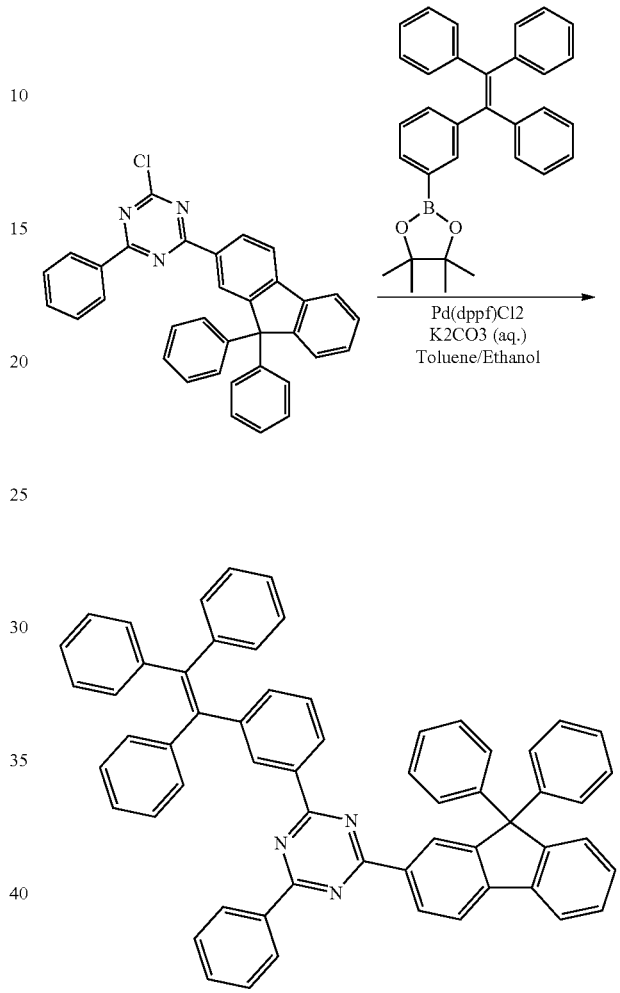

Reagents and reaction conditions: 2-chloro-4-(9,9-diphenyl-9H-fluoren-2-yl)-6-phenyl-1,3,5-triazine (1.0 eq.), 4,4,5,5-tetramethyl-2-(3-(1,2,2-triphenylvinyl)phenyl)-1,3,2-dioxaborolane (1.2 eq.), Pd(dppf)Cl$_2$ (0.02 eq.), potassium carbonate (2.0 eq.). 18 h at 100° C. (600 mL, toluene/ethanol/H$_2$O 4/1/1).

When the reaction was completed according TLC, the solvent was evaporated. The crude mixture was dissolved in chloroform and washed with water. Organic phase was filtered over a pad of silicagel, and the solvent was evaporated. The resulting oil was stirred overnight in a mixture of hexane/dichloromethane. Solid was then filtered, and stirred overnight in a mixture cyclohexane/dichloromethane. Solid was filtered and dissolved in a hot mixture of cyclohexane and toluene. Some insoluble side-products were filtered off. The solution was cooled down to room temperature and the precipitate was filtered. 10.5 g (40% yield). MS (ESI): 804 (M+H).

Synthesis of 2-phenyl-4,6-bis(4-(1,2,2-triphenylvinyl)phenyl)-1,3,5-triazine

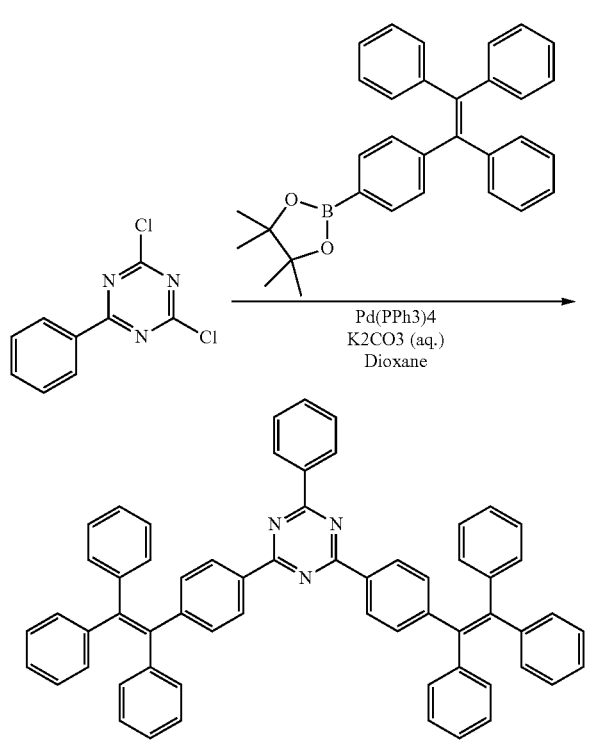

Reagents and reaction conditions: 2,4-dichloro-6-phenyl-1,3,5-triazine (1.0 eq.), 4,4,5,5-tetramethyl-2-(4-(1,2,2-triphenylvinyl)phenyl)-1,3,2-dioxaborolane (2.2 eq.), tetrakistriphenylphosphine palladium (0) (Pd(PPh$_3$)$_4$) (0.04 eq.), potassium carbonate (4.0 eq.). 17 h at 90° C. (126 mL, dioxane/H$_2$O 2/1).

When the reaction was completed according TLC, reaction was cooled down to room temperature and solvent was evaporated. Crude compound was dissolved in chloroform and washed with water. Organic phase was filtered over a pad of silicagel and solvent was then evaporated. Crude solid was recrystallized first in toluene, and then in chlorobenzene. 5.5 g (49% yield). MS (ESI): 818 (M+H).

Synthesis of 2-(dibenzo[b,d]furan-3-yl)-4,6-bis(4-(1,2,2-triphenylvinyl)phenyl)-1,3,5-triazine

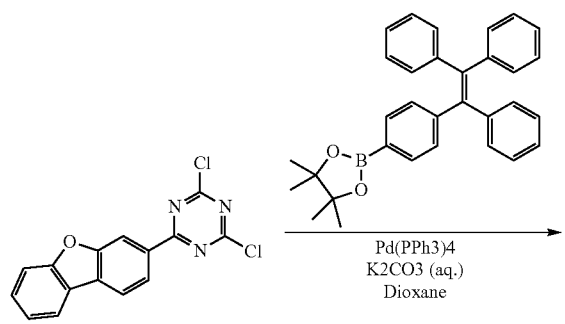

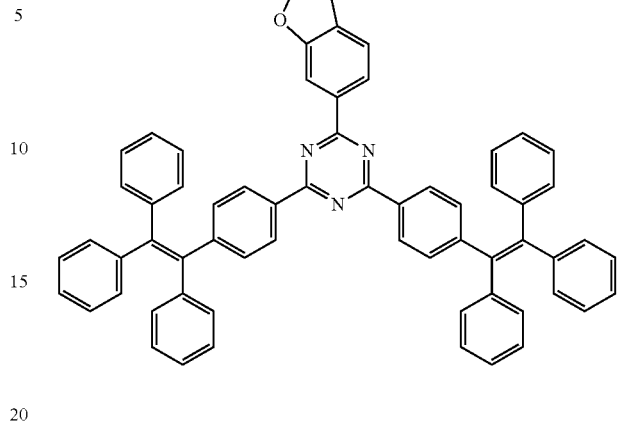

Reagents and reaction conditions: 2,4-dichloro-6-(dibenzo[b,d]furan-3-yl)-1,3,5-triazine (1.0 eq.), 4,4,5,5-tetramethyl-2-(4-(1,2,2-triphenylvinyl)phenyl)-1,3,2-dioxaborolane (2.2 eq.), tetrakistriphenylphosphine palladium (0) (Pd(PPh$_3$)$_4$) (0.04 eq.), potassium carbonate (4.0 eq.). 17 h at 90° C. (112 mL, dioxane/H$_2$O 2/1).

When the reaction was completed according TLC, precipitate was filtered and washed with water. Then it was dissolved in dichloromethane and filtered over a pad of florisil, then concentrated to induce precipitation. Upon addition of cyclohexane, precipitation took place. Solid was filtered and recrystallized in toluene. 4.1 g (36% yield). MS (ESI): 908 (M+H).

Synthesis of 2-(dibenzo[b,d]furan-3-yl)-4,6-bis(3-(1,2,2-triphenylvinyl)phenyl)-1,3,5-triazine

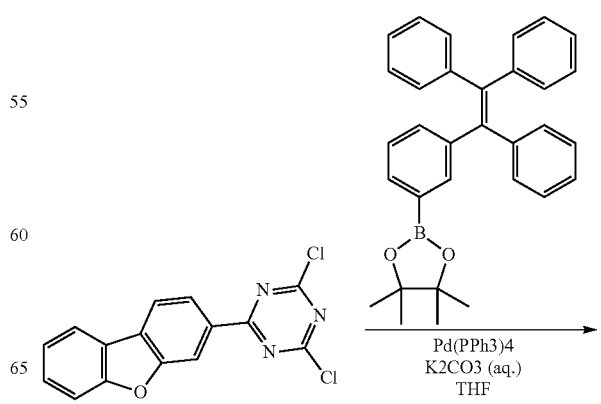

-continued

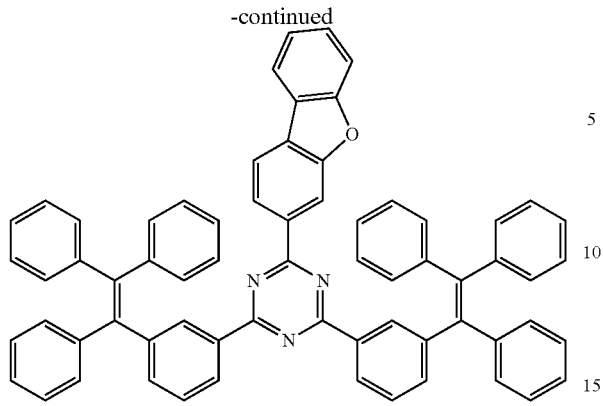

Reagents and reaction conditions: 2,4-dichloro-6-(dibenzo[b,d]furan-3-yl)-1,3,5-triazine (1.0 eq.), 4,4,5,5-tetramethyl-2-(3-(1,2,2-triphenylvinyl)phenyl)-1,3,2-dioxaborolane (2.2 eq.), tetrakistriphenylphosphine palladium (0) (Pd(PPh$_3$)$_4$) (0.04 eq.), potassium carbonate (4.0 eq.). 19 h at 100° C. (150 mL, THF/H$_2$O 2/1).

When the reaction was completed according TLC, the solvent was evaporated. The crude mixture was dissolved in chloroform and washed with water. Organic phase was filtered over a pad of silicagel, and the solvent was evaporated. The resulting oil was stirred overnight in a mixture of hexane/dichloromethane. Solid was then filtered, dissolved in chloroform and precipitated upon addition of hexanes. Finally it was dissolved in dichloromethane and precipitated upon addition of cyclohexanes. 6.2 g (36% yield). MS (ESI): 908 (M+H).

Synthesis of Intermediates

Synthesis of 4,4,5,5-tetramethyl-2-(3-(1,2,2-triphenylvinyl)phenyl)-1,3,2-dioxaborolane, 4,4,5,5-tetramethyl-2-(4-(1,2,2-triphenylvinyl)phenyl)-1,3,2-dioxaborolane, (2-(3-bromophenyl)ethene-1,1,2-triyl)tribenzene and (2-(4-bromophenyl)ethene-1,1,2-triyl)tribenzene according to Chemical Communications, 48(77), 9586-9588; 2012.

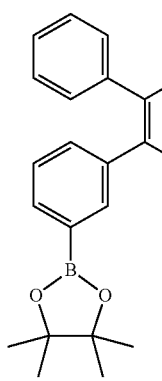

-continued

Synthesis of 2-(3-(4,4,5,5-tetramethyl-1,3,2-dioxaborolan-2-yl)phenyl)pyridine according to Angewandte Chemie International Edition, 54(50), 15284-15288; 2015.

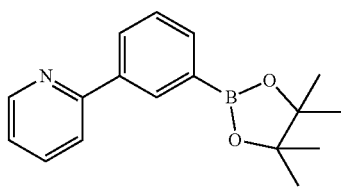 [SMILES: CC1(C)OB(c2cccc(-c3ccccn3)c2)OC1(C)C]

Synthesis of 2-chloro-4,6-di(naphthalen-2-yl)-1,3,5-triazine according to U.S. Pat. Appl. Publ., 20130248830, 26 Sep. 2013

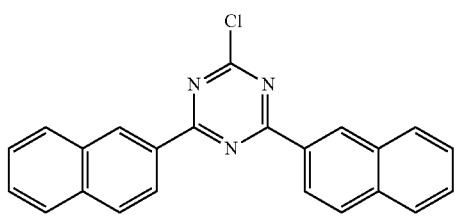 [SMILES: Clc1nc(-c2ccc3ccccc3c2)nc(-c2ccc3ccccc3c2)n1]

Synthesis of 2,4-dichloro-6-(naphthalen-2-yl)-1,3,5-triazine according to Repub. Korean Kongkae Taeho Kongbo, 2014094408, 30 Jul. 2014

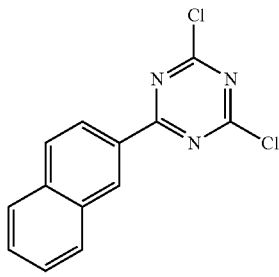 [SMILES: Clc1nc(Cl)nc(-c2ccc3ccccc3c2)n1]

Synthesis of 2-([1,1'-biphenyl]-4-yl)-4,6-dichloro-1,3,5-triazine according to PCT Int. Appl., 2016204375, 22 Dec. 2016

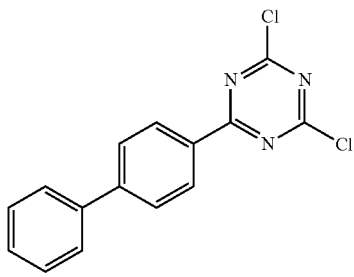 [SMILES: Clc1nc(Cl)nc(-c2ccc(-c3ccccc3)cc2)n1]

Synthesis of 2,4-dichloro-6-(dibenzo[b,d]furan-3-yl)-1,3,5-triazine was synthesized by Grignard reaction following the same procedure than the one reported for the naphtyl analogue (2,4-dichloro-6-(naphthalen-2-yl)-1,3,5-triazine)

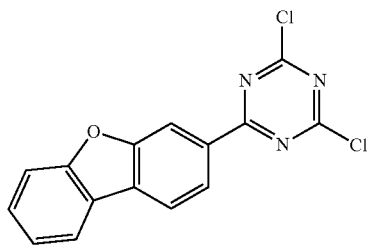 [SMILES: Clc1nc(Cl)nc(-c2ccc3c(c2)oc2ccccc23)n1]

Synthesis of 2-(3-bromo-5-chlorophenyl)benzo[d]thiazole was synthesized starting from 3-bromo-5-chlorobenzoic acid following the same procedure as for the synthesis of 2-(4-bromophenyl)benzo[d]thiazole (From Eur. Pat. Appl., 1746096, 24 Jan. 2007)

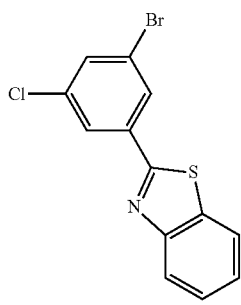 [SMILES: Clc1cc(Br)cc(-c2nc3ccccc3s2)c1]

Synthesis of 2-(dibenzo[b,d]thiophen-3-yl)-4,4,5,5-tetramethyl-1,3,2-dioxaborolane was carried out according PCT Int. Appl., 2015165826, 5 Nov. 2015

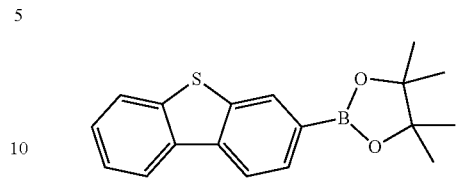

Synthesis of 2-chloro-4-(dibenzo[b,d]thiophen-3-yl)-6-phenyl-1,3,5-triazine

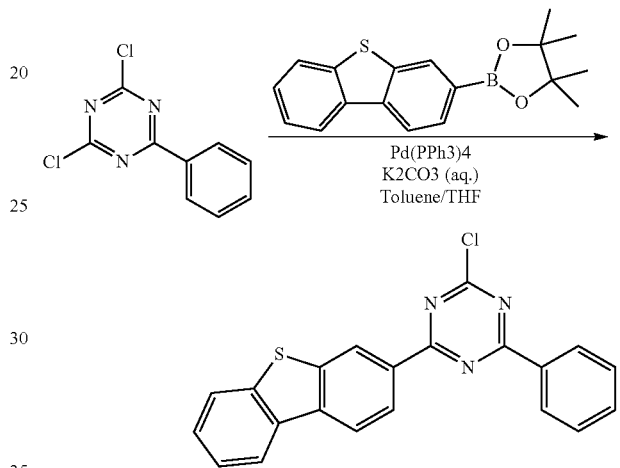

Reagents and reaction conditions: 2,4-dichloro-6-phenyl-1,3,5-triazine (1.0 eq.), 2-(dibenzo[b,d]thiophen-3-yl)-4,4,5,5-tetramethyl-1,3,2-dioxaborolane (0.8 eq.), tetrakistriphenylphosphine palladium (0) (Pd(PPh$_3$)$_4$) (0.02 eq.), potassium carbonate (2.0 eq.). 4 h at 65° C. (270 mL THF/toluene/H$_2$O 1/1/1).

When the reaction was completed according TLC, the solvent was evaporated. The crude mixture was dissolved in toluene and washed with water. Organic phase was filtered over a pad of florisil, and the solvent was partially evaporated. Upon addition of hexane, precipitation was observed. Solid was then filtered, and recrystallized in toluene. 12.6 g (37% yield). GC-MS: 373.

Synthesis of 2-chloro-4-(dibenzo[b,d]furan-3-yl)-6-phenyl-1,3,5-triazine

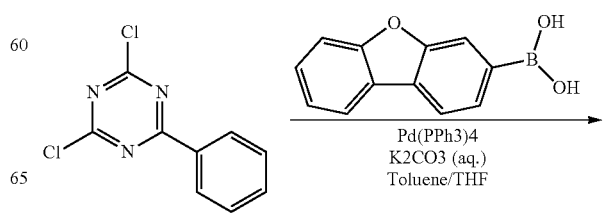

-continued

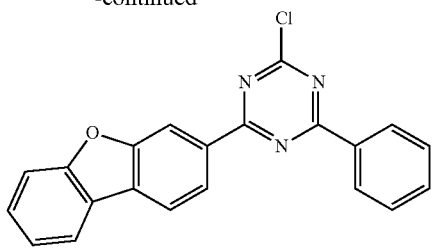

Reagents and reaction conditions: 2,4-dichloro-6-phenyl-1,3,5-triazine (1.0 eq.), dibenzo[b,d]furan-3-ylboronic acid (0.8 eq.), tetrakistriphenylphosphine palladium (0) (Pd(PPh₃)₄) (0.02 eq.), potassium carbonate (2.0 eq.). 1 h at 100° C. (1110 mL THF/toluene/H₂O 1/1/1).

When the reaction was completed according TLC, the reaction was cooled down to 5° C. The precipitate was filtered and washed with water. Solid was dissolved in chloroform at 60° C., filtered over a pad of silicagel and then solvent is partially evaporated. Upon addition of hexane a precipitate was formed. The solid was filtered and further purified by sublimation 63 g (41% yield). GC-MS: 357.

Synthesis of 2-chloro-4-phenyl-6-(3-(1,2,2-triphenylvinyl)phenyl)-1,3,5-triazine

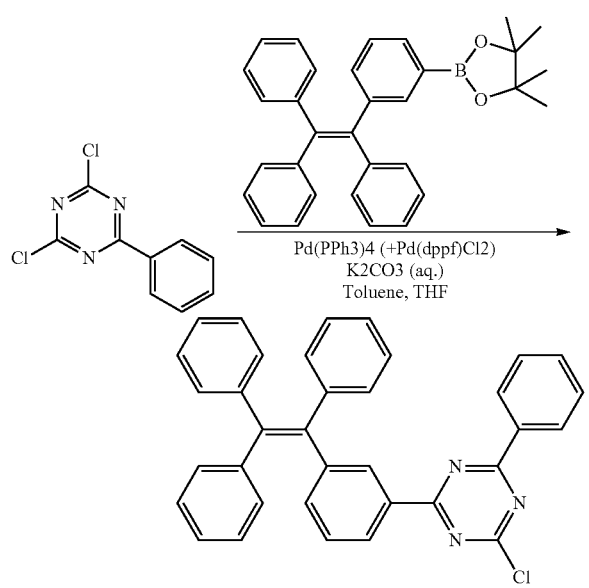

Reagents and reaction conditions: 2,4-dichloro-6-phenyl-1,3,5-triazine (1.0 eq.), 4,4,5,5-tetramethyl-2-(3-(1,2,2-triphenylvinyl)phenyl)-1,3,2-dioxaborolane (0.8 eq.), tetrakistriphenylphosphine palladium (0) (Pd(PPh₃)₄) (0.02 eq.)+ Pd(dppf)Cl₂ (0.05 eq.), potassium carbonate (2.0 eq.). 13 h at 65° C. (450 mL THF/toluene/H₂O 1/1/1).

When the reaction was completed according TLC, the aqueous phase was separated. Organic phase was extracted with water. Solvent was evaporated and the crude material was purified by column chromatography (hexane/dichloromethane 4/1), and used directly as such. 11.5 g (25% yield). GC-MS: 521.

Synthesis of 2-chloro-4-(9,9-diphenyl-9H-fluoren-2-yl)-6-phenyl-1,3,5-triazine

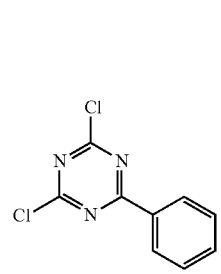 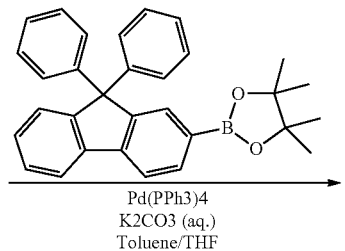

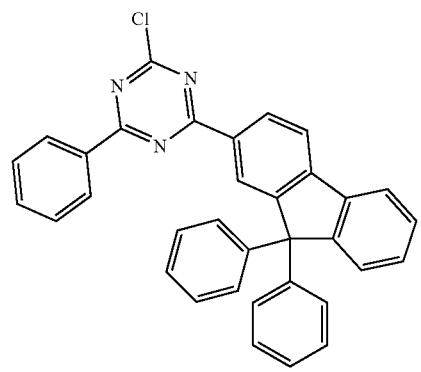

Reagents and reaction conditions: 2,4-dichloro-6-phenyl-1,3,5-triazine (1.0 eq.), 2-(9,9-diphenyl-9H-fluoren-2-yl)-4,4,5,5-tetramethyl-1,3,2-dioxaborolane (0.8 eq.), tetrakistriphenylphosphine palladium (0) (Pd(PPh₃)₄) (0.02 eq.), potassium carbonate (2.0 eq.). 7 h at 95° C. (900 mL THF/toluene/H₂O 1/1/1).

When the reaction was completed according TLC, aqueous phase was separated and organic phase was washed with water. Organic solvent was partially evaporated and upon addition of acetonitrile, precipitation was observed. Solid was then filtered, and further purified through column chromatography (toluene/hexane 1/2). 14.5 g (42% yield). ESI-MS: 508 (M+H).

Synthesis of 2-chloro-4-(dibenzo[b,d]furan-3-yl)-6-(naphthalen-2-yl)-1,3,5-triazine

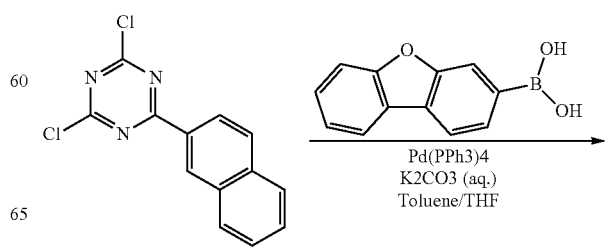

-continued

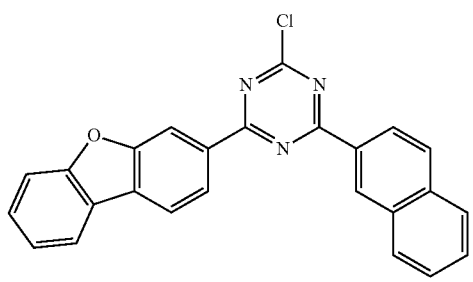

Reagents and reaction conditions: 2,4-dichloro-6-(naphthalen-2-yl)-1,3,5-triazine (1.0 eq.), dibenzo[b,d]furan-3-yl-boronic acid (0.8 eq.), tetrakistriphenylphosphine palladium (0) (Pd(PPh$_3$)$_4$) (0.02 eq.), potassium carbonate (2.0 eq.). 2 h at 90° C. (2550 mL, THF/toluene/H$_2$O 1/1/1).

When the reaction was completed according TLC, the reaction was cooled down to room temperature. The precipitate was filtered and washed with water. Solid was dissolved in hot chlorobenzene, filtered over a pad of silicagel and then solvent was partially evaporated. Solid was filtered, triturated in ethylacetate and further purified by sublimation. 130.8 g, (41% yield). ESI-MS: 408 (M+H).

Synthesis of 2-([1,1'-biphenyl]-4-yl)-4-chloro-6-(dibenzo[b,d]furan-3-yl)-1,3,5-triazine

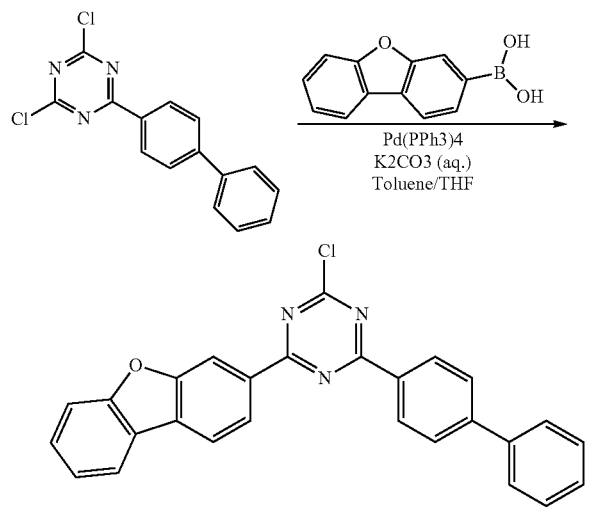 [SMILES: Clc1nc(Cl)nc(-c2ccc(-c3ccccc3)cc2)n1 ; OB(O)c1ccc2c(c1)oc1ccccc12 ; Clc1nc(-c2ccc(-c3ccccc3)cc2)nc(-c2ccc3c(c2)oc2ccccc23)n1]

Reagents and reaction conditions: 2-([1,1'-biphenyl]-4-yl)-4,6-dichloro-1,3,5-triazine (1.0 eq.), dibenzo[b,d]furan-3-ylboronic acid (0.8 eq.), tetrakistriphenylphosphine palladium (0) (Pd(PPh$_3$)$_4$) (0.02 eq.), potassium carbonate (2.0 eq.). 4 h at 65° C. (2400 mL THF/toluene/H$_2$O 1/1/1).

When the reaction was completed according TLC, the reaction was cooled down to room temperature. The precipitate was filtered and washed with water. Solid was dissolved in hot toluene, filtered hot over a pad of silicagel and then solvent was partially evaporated. Solid was filtered. 60 g, (27% yield). ESI-MS: 434 (M+H).

Synthesis of 2-([1,1'-biphenyl]-2-yl)-4-chloro-6-(dibenzo[b,d]furan-3-yl)-1,3,5-triazine

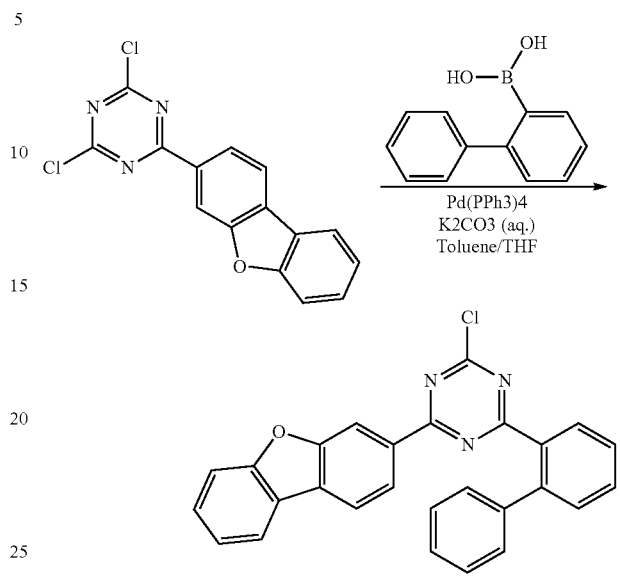

Reagents and reaction conditions: 2,4-dichloro-6-(dibenzo[b,d]furan-3-yl)-1,3,5-triazine (1.0 eq.), [1,1'-biphenyl]-2-ylboronic acid (0.8 eq.), tetrakistriphenylphosphine palladium (0) (Pd(PPh$_3$)$_4$) (0.05 eq.), potassium carbonate (2.5 eq.). 11 h at 65° C. (570 mL THF/toluene/H$_2$O 1/1/1).

When the reaction was completed according TLC, the solvent was evaporated. The crude mixture was dissolved in chloroform and washed with water. Organic phase was filtered over a pad of silicagel and the solvent was partially evaporated. Upon addition of hexane, precipitation was observed. Solid was then filtered, stirred in dichloromethane and filtered again. 12.8 g (39% yield). GC-MS: 433.

General Procedure for Fabrication of Organic Electronic Devices

In general organic electronic devices may be organic light-emitting diodes (OLEDs), organic photovoltaic cells (OSCs), organic field-effect transistors (OFETs) or organic light emitting transistors (OLETs).

Any functional layer in the organic electronic device may comprise a compound of formula 1 or may consist of a compound of formula 1.

An OLED may be composed of individual functional layers to form a top-emission OLED which emits light through the top electrode. Herein, the sequence of the individual functional layers may be as follows wherein contact interfaces between the individual layers are shown as "/": non-transparent anode layer (bottom electrode)/hole injection layer/hole transport layer/electron blocking layer/emission layer/hole blocking layer/electron transport layer/electron injection layer/transparent cathode layer (top electrode). Each layer may in itself be constituted by several sub-layers.

An OLED may be composed of individual functional layers to form a bottom-emission OLED which emits light through the bottom electrode. Herein, the sequence of the individual functional layers may be as follows wherein contact interfaces between the individual layers are shown as "/": transparent anode layer (bottom electrode)/hole injection layer/hole transport layer/electron blocking layer/emission layer/hole blocking layer/electron transport layer/electron injection layer/non-transparent cathode layer (top electrode). Each layer may in itself be constituted by several sub-layers.

Top-emission OLED devices were prepared to demonstrate the technical benefit utilizing the compounds of formula 1 in an organic electronic device.

Fabrication of Top Emission Devices

For all top emission devices, inventive example 1-8 and comparative example 1, a glass substrate was cut to a size of 50 mm×50 mm×0.7 mm, ultrasonically cleaned with isopropyl alcohol for 5 minutes and then with pure water for 5 minutes, and cleaned again with UV ozone for 30 minutes, to prepare a first electrode. 100 nm Ag were deposited at a pressure of $10^{-5}$ to $10^{-7}$ mbar to form the anode. Then, 92 vol.-% Biphenyl-4-yl(9,9-diphenyl-9H-fluoren-2-yl)-[4-(9-phenyl-9H-carbazol-3-yl)phenyl]-amine (CAS 1242056-42-3) with 8 vol.-% 4,4',4"-((1E,1'E,1"E)-cyclopropane-1,2,3-triylidenetris(cyanomethan-ylylidene))tris(2,3,5,6-tetrafluorobenzonitrile) was vacuum deposited on the Ag electrode, to form a HIL having a thickness of 10 nm. Then, Biphenyl-4-yl(9,9-diphenyl-9H-fluoren-2-yl)-[4-(9-phenyl-9H-carbazol-3-yl)phenyl]-amine (CAS 1242056-42-3) was vacuum deposited on the HIL, to form a HTL having a thickness of 118 nm. Then, N,N-bis(4-(dibenzo[b,d]furan-4-yl)phenyl)-[1,1': 4',1"-terphenyl]-4-amine (CAS 1198399-61-9) was vacuum deposited on the HTL, to form an electron blocking layer (EBL) having a thickness of 5 nm.

For top emission devices, 97 vol.-% H09 (Sun Fine Chemicals) as EML host and 3 vol.-% BD200 (Sun Fine Chemicals) as fluorescent blue dopant were deposited on the EBL, to form a blue-emitting EML with a thickness of 20 nm. Then, the hole blocking layer is formed with a thickness of 5 nm by depositing 2,4-diphenyl-6-(4',5', 6'-triphenyl-[1, 1': 2',1": 3",1'":3"',1""-quinquephenyl]-3""-yl)-1,3,5-triazine on the emission layer. Then, the electron transporting layer is formed on the hole blocking layer according to Examples LL to MM and comparative example NN with a the thickness of 31 nm. The electron transport layer comprises 50 wt.-% of compound of formula 1 (or of the comparative compound) and 50 wt.-% of 8-Hydroxyquinolinolato-lithium (LiQ).

Then, the electron injection layer is formed on the electron transporting layer by deposing Yb with a thickness of 2 nm. Ag is evaporated at a rate of 0.01 to 1 Å/s at $10^{-7}$ mbar to form a cathode with a thickness of 11 nm. A cap layer of Biphenyl-4-yl(9,9-diphenyl-9H-fluoren-2-yl)-[4-(9-phenyl-9H-carbazol-3-yl)phenyl]-amine is formed on the cathode with a thickness of 75 nm.

The OLED stack is protected from ambient conditions by encapsulation of the device with a glass slide. Thereby, a cavity is formed, which includes a getter material for further protection.

To assess the performance of the inventive examples compared to the existing art, the light output of the top emission OLEDs is measured under ambient conditions (20° C.). Current voltage measurements are performed using a Keithley 2400 sourcemeter, and recorded in V. At 10 mA/cm² for top emission devices, a spectrometer CAS140 CT from Instrument Systems, which has been calibrated by Deutsche Akkreditierungsstelle (DAkkS), is used for measurement of CIE coordinates and brightness in Candela. The current efficiency Ceff is determined at 10 mA/cm² in cd/A.

In top emission devices, the emission is forward directed, non-Lambertian and also highly dependent on the microcavity. Therefore, the external quantum efficiency (EQE) and power efficiency in lm/W will be higher compared to bottom emission devices.

Compounds Used

| IUPAC name | Formula | Reference |
|---|---|---|
| Biphenyl-4-yl(9,9-diphenyl-9H-fluoren-2-yl)-[4-(9-phenyl-9H-carbazol-3-yl)phenyl]-amine (CAS 1242056-42-3) | | US2016322581 |

| IUPAC name | Formula | Reference |
|---|---|---|
| 4,4',4''-((1E,1'E,1''E)-cyclopropane-1,2,3-triylidenetris(cyano-methanylylidene))tris(2,3,5,6-tetrafluorobenzonitrile) | | US2008265216 |
| N,N-bis(4-(dibenzo[b,d]furan-4-yl)phenyl)-[1,1':4',1''-terphenyl]-4-amine (CAS 1198399-61-9) | | JP2014096418 |
| H09 | Fluorescent-blue host material- | Commercially available from Sun Fine Chemicals, Inc., S. Korea |
| BD200 | Fluorescent-blue emitter material | Commercially available from Sun Fine Chemicals Inc., S. Korea |
| 2,4-diphenyl-6-(4',5',6'-triphenyl-[1,1':2',1'':3'',1''':3''',1'''''-quinquephenyl]-3''''-yl)-1,3,5-triazine | | — |

| IUPAC name | Formula | Reference |
|---|---|---|
| 8-Hydroxyquinolinolato-lithium (850918-68-2) Alkali organic complex 1 = AOC-1 | | WO2013079217 |

Melting Point

The melting point (Tm) is determined as peak temperatures from the DSC curves of the above TGA-DSC measurement or from separate DSC measurements (Mettler Toledo DSC822e, heating of samples from room temperature to completeness of melting with heating rate 10 K/min under a stream of pure nitrogen. Sample amounts of 4 to 6 mg are placed in a 40 µL Mettler Toledo aluminum pan with lid, a <1 mm hole is pierced into the lid).

Glass Transition Temperature

The glass transition temperature (Tg) is measured under nitrogen and using a heating rate of 10 K per min in a Mettler Toledo DSC 822e differential scanning calorimeter as described in DIN EN ISO 11357, published in March 2010.

Rate Onset Temperature

The rate onset temperature ($T_{RO}$) for transfer into the gas phase is determined by loading 100 mg compound into a VTE source. As VTE source a point source for organic materials is used as supplied by Kurt J. Lesker Company (www.lesker.com) or CreaPhys GmbH (http://www.creaphys.com). The VTE (vacuum thermal evaporation) source temperature is determined through a thermocouple in direct contact with the compound in the VTE source.

The VTE source is heated at a constant rate of 15 K/min at a pressure of $10^{-7}$ to $10^{-8}$ mbar in the vacuum chamber and the temperature inside the source measured with a thermocouple. Evaporation of the compound is detected with a QCM detector which detects deposition of the compound on the quartz crystal of the detector. The deposition rate on the quartz crystal is measured in Å ngstrom per second. To determine the rate onset temperature, the deposition rate on a logarithmic scale is plotted against the VTE source temperature. The rate onset is the temperature at which noticeable deposition on the QCM detector occurs (defined as a rate of 0.02 Å/s. The VTE source is heated and cooled three time and only results from the second and third run are used to determine the rate onset temperature. The rate onset temperature is an indirect measure of the volatility of a compound. The higher the rate onset temperature the lower is the volatility of a compound.

Technical Effect of the Invention

In summary, organic electronic devices comprising compounds with formula 1 inherent to their molecular structure have higher current efficiency. The glass transition temperature and rate onset temperature are within the range acceptable for mass production of organic semiconductor layers.

TABLE 1

Table 1: Structural formula, glass transition temperature, melting temperature, rate onset temperature of comparative compound.

| Name | | Formula | Tg [° C.] | Tm [° C.] | $T_{RO}$ [° C.] |
|---|---|---|---|---|---|
| Comparative Compound 1 | Comparative-1 | | 159 | 302 | 268 |

TABLE 2

Structural formulae, glass transition temperature, melting temperature, rate onset temperature of inventive compounds.

| Name | | Formula | Tg [°C] | Tm [°C] | $T_{RO}$ [°C] |
|---|---|---|---|---|---|
| Inventive Compound 1 | G1 | | 116 | 227 | 230 |
| Inventive compound 2 | G2 | | 126 | 252 | 237 |
| Inventive Compound 3 | G4 | | 165 | 352 | 308 |

TABLE 2-continued

Structural formulae, glass transition temperature, melting temperature, rate onset temperature of inventive compounds.

| Name | | Formula | Tg [° C.] | Tm [° C.] | T$_{RO}$ [° C.] |
|---|---|---|---|---|---|
| Inventive Compound 4 | G5 | | — | 272 | 271 |
| Inventive Compound 5 | G6 | | — | 251 | — |
| Inventive Compound 6 | G29 | | 125 | 271 | 248 |

TABLE 2-continued

Structural formulae, glass transition temperature, melting temperature, rate onset temperature of inventive compounds.

| Name | | Formula | Tg [° C.] | Tm [° C.] | T$_{RO}$ [° C.] |
|---|---|---|---|---|---|
| Inventive Compound 7 | G30 | | 129 | 280 | 264 |
| Inventive Compound 8 | G8 | | 109 | 229 | 217 |

In Table 1 are shown glass transition temperatures, melting temperatures, rate onset temperatures of comparative compounds.

In Table 2 are shown glass transition temperatures, melting temperatures, rate onset temperatures of compounds of formula 1.

TABLE 3

Performance data of top emission OLED devices comprising an electron transport layer which comprises the compounds of formula 1 and comparative compounds and an alkali organic complex. The inventive examples show increased cd/A efficiencies

| | Comparative compounds and compounds of formula 1 | vol.-% compound of formula 1 | Alkali organic complex (AOC) | vol.-% alkali organic complex | Thickness ETL/nm | CIE 1931 y | Operating voltage at 10 mA/cm$^2$ (V) | cd/A efficiency at 10 mA/cm$^2$ (cd/A) |
|---|---|---|---|---|---|---|---|---|
| Comparative example 1 | Comparative-1 | 50 | AOC-1 | 50 | 31 | 0.044 | 3.54 | 7.35 |
| Inventive example 1 | G1 | 50 | AOC-1 | 50 | 31 | 0.047 | 3.52 | 8.19 |
| Inventive example 2 | G2 | 50 | AOC-1 | 50 | 31 | 0.045 | 3.46 | 7.93 |

TABLE 3-continued

Performance data of top emission OLED devices comprising an electron transport layer which comprises the compounds of formula 1 and comparative compounds and an alkali organic complex. The inventive examples show increased cd/A efficiencies

| | Comparative compounds and compounds of formula 1 | vol.-% compound of formula 1 | Alkali organic complex (AOC) | vol.-% alkali organic complex | Thickness ETL/nm | CIE 1931 y | Operating voltage at 10 mA/cm² (V) | cd/A efficiency at 10 mA/cm² (cd/A) |
|---|---|---|---|---|---|---|---|---|
| Inventive example 3 | G4 | 50 | AOC-1 | 50 | 31 | 0.048 | 3.41 | 8.00 |
| Inventive example 4 | G5 | 50 | AOC-1 | 50 | 31 | 0.044 | 3.50 | 8.02 |
| Inventive example 5 | G6 | 50 | AOC-1 | 50 | 31 | 0.046 | 3.43 | 7.95 |
| Inventive example 6 | G29 | 50 | AOC-1 | 50 | 31 | 0.046 | 3.45 | 7.91 |
| Inventive example 7 | G30 | 50 | AOC-1 | 50 | 31 | 0.048 | 3.42 | 7.87 |
| Inventive example 8 | G8 | 50 | AOC-1 | 50 | 31 | 0.045 | 3.60 | 7.63 |

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound, for use as a layer material for an organic electronic device, according to formula I:

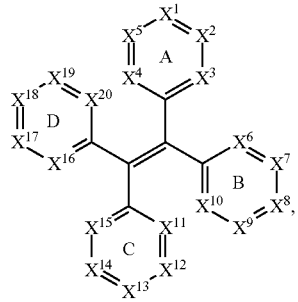

(I)

wherein
$X^1$ to $X^{20}$ are independently select from N, C—H, C—$R^1$, C—Z, and/or at least two of $X^1$ to $X^5$, $X^6$ to $X^{10}$, $X^{11}$ to $X^{15}$, $X^{16}$ to $X^{20}$, which are connected to each other by a chemical bond, are bridged to form an anellated aromatic ring or anellated heteroaromatic ring; and
wherein at least one $X^1$ to $X^{20}$ is C—Z; or at least one $X^1$ to $X^{20}$ is C—Z and at least one $X^1$ to $X^{20}$ is C—$R^1$;
$R^1$ is selected from —$NR^2R^3$ or —$BR^2R^3$;
$R^2$ and $R^3$ am independently selected $C_{6-24}$ aryl or $C_{2-20}$ heteroaryl;
Z is a substituent of formula II:

$$-\!\!\!-\!\!(Ar^1)\!\!-\!\!(Ar^2)_m;$$
(II)

wherein
$Ar^1$ is a substituted or unsubstituted triazine ring,
wherein the substituents of the substituted triazine ring are independently selected from linear $C_{1-20}$ alkyl, branched $C_{3-20}$ alkyl or $C_{3-20}$ cyclic alkyl, linear $C_{1-12}$ fluorinated alkyl, linear $C_{1-12}$ fluorinated alkoxy, branched $C_{3-12}$ fluorinated alkyl, branched $C_{3-12}$ fluorinated alkoxy, $C_{3-12}$ cyclic fluorinated alkyl, $C_{3-12}$ cyclic fluorinated alkoxy, OR, SR, (P=O)$R_2$ or formula I with the exception that $X^1$ to $X^{20}$ are not C—Z;
$Ar^2$ are independently selected from:
formula I, with the exception that $X^1$ to $X^{20}$ are not C—Z, substituted or unsubstituted $C_{6-60}$ aryl, and substituted or unsubstituted $C_2$-$C_{60}$ heteroaryl;
wherein the substituents of the $C_{6-60}$aryl and $C_2$-$C_{60}$n heteroaryl are independently selected from $C_1$-$C_{20}$ linear alkyl, $C_3$-$C_{20}$branched alkyl, $C_3$-$C_{20}$ cyclic alkyl; $C_1$-$C_{20}$ linear alkoxy, $C_3$-$C_{20}$ branched alkoxy; linear fluorinated $C_1$-$C_{12}$ alkyl, or linear fluorinated $C_1$-$C_{12}$ alkoxy; $C_3$-$C_{12}$ branched cyclic fluorinated alkyl, $C_3$-$C_{12}$ cyclic fluorinated alkyl, $C_3$-$C_{12}$ cyclic fluorinated alkoxy; nitrile; OR, SR, (C=O)R, (C=O)$NR_2$, $SiR_3$, (S=O)R, (S=O)$_2$R, (P=O)$R_2$;
R is $C_1$-$C_2$linear alkyl, $C_1$-$C_{20}$ alkoxy, $C_1$-$C_{20}$ thioalkyl, $C_3$-$C_{20}$ branched alkyl, $C_3$-$C_{20}$cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$aryl and $C_3$-$C_{20}$heteroaryl;
m is selected from 1, 2 or 3.

2. The compound according to claim 1, wherein the compound according to formula I:
comprises at least 5 to 20 aromatic rings.

3. The compound according to claim 1, wherein the $Ar^1$ group is a triazine ring.

4. The compound according to claim 1, wherein in for formula I:
$X^1$ to $X^2$ are independently selected from C—H, C—$R^1$, C—Z,
wherein at least one $X^1$ to $X^{20}$ is selected from C—Z:
$R^1$ is selected from —$NR^2R^3$ or —$BR^2R^3$;
$R^2$ and $R^3$ are independently selected $C_{6-16}$ aryl or $C_{2-12}$ heteroaryl;
is a substituent of formula II:

$$-\!\!\!-\!\!(Ar^1)\!\!-\!\!(Ar^2)_m;$$
(II)

wherein
Ar$^1$ is a triazine ring;
Ar$^2$ are independently selected from substituted or unsubstituted C$_{12-60}$ aryl or substituted or unsubstituted C$_{10}$-C$_{59}$ heteroaryl:
  wherein the substituents are independently selected from nitrile, di-alkyl phosphine oxide, di-aryl phosphine oxide, C$_2$-C$_{16}$ heteroaryl, fluorinated C$_1$-C$_6$ alkyl or fluorinated C$_1$-C$_6$ alkoxy,
    wherein the substituents are selected from C$_1$-C$_{20}$ linear alkyl C$_3$-C$_{20}$ branched alkyl, C$_3$-C$_{20}$ cyclic alkyl, linear fluorinated C$_1$-C$_{12}$ alkyl, linear C$_3$-C$_{20}$ alkoxy, branched C$_1$-C$_{12}$ fluorinated alkyl, C$_3$-C$_{12}$ cyclic fluorinated alkyl, branched C$_1$-C$_{12}$ fluorinated alkoxy, C$_3$-C$_{12}$ cyclic fluorinated alkoxy, nitrile, OR, SR, (C=O)R, (C=O)NR$_2$, SiR$_3$, (S=O)R, (S=O)$_2$R, (P=O)R$_2$;
R is C$_1$-C$_{20}$ linear alkyl, C$_1$-C$_{20}$ alkoxy, C$_1$-C$_{20}$ thioalkyl, C$_3$-C$_{20}$ branched alkyl, C$_3$-C$_{20}$ cyclic alkyl, C$_3$-C$_{20}$ branched alkoxy, C$_3$-C$_{20}$ cyclic alkoxy, C$_3$-C$_{20}$ branched thioalkyl, C$_3$-C$_{20}$ cyclic thioalkyl, C$_6$-C$_{20}$ aryl and C$_3$-C$_{20}$ heteroaryl;
m is selected from 1, 2 or 3.

5. The compound according to claim 1, wherein in formula I:
X$^1$ to X$^{20}$ are independently selected from C—H, C—Z;
  wherein at least one X$^1$ to X$^{20}$ is selected from C—Z;
R$^1$ is selected from —NR$^2$R$^3$ or —BR$^2$R$^3$;
R$^2$ and R$^3$ are independently selected C$_{6-16}$ aryl or C$_{2-12}$ heteroaryl;
Z is a substituent of formula II:

$$-\!\!+\!\!Ar^1\!\!+\!\!+\!\!Ar^2)_m;$$  (II)

wherein
Ar$^1$ is a triazine ring;
Ar$^2$ are independently selected from substituted or unsubstituted C$_{12}$-C$_{60}$ aryl or substituted or unsubstituted C$_{10}$-C$_{59}$ heteroaryl;
  wherein the substituents are independently selected from nitrite, di-alkyl phosphine oxide, di-aryl phosphine oxide, C$_{12}$-C$_{16}$ heteroaryl, fluorinated C$_1$-C$_6$ alkyl or fluorinated C$_1$-C$_6$ alkoxy, OR, SR, (C=O)R, (C=O)NR$_2$, SiR$_3$, (S=O)R, (S=O)$_2$R, (P=O)R$_2$;
R is independently selected from a linear C$_1$-C$_{20}$ alkyl, linear C$_1$-C$_{20}$ alkoxy, linear C$_1$-C$_{20}$ thioalkyl, a branched C$_3$-C$_{20}$ alkyl, branched C$_3$-C$_{20}$ alkoxy, branched C$_3$-C$_{20}$ thioalkyl, C$_{6-20}$ aryl and C$_3$-C$_{20}$ heteroaryl;
m is selected from 1 or 2.

6. The compound according to claim 1, wherein Z has the formula III:

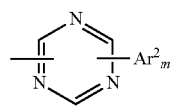  (III)

wherein
Ar$^2$ is independently selected from substituted or unsubstituted C$_{6-60}$ aryl or C$_2$-C$_{60}$ heteroaryl wherein
  the substituents are independently selected from nitrile, C$_1$-C$_{20}$ di-alkyl phosphine oxide, C$_{6-20}$ di-aryl phosphine oxide, C$_2$-C$_{36}$ heteroaryl, fluorinated C$_1$-C$_6$ alkyl or fluorinated C$_1$-C$_6$ alkoxy, OR, SR, (C=O)R, (C=O)NR$_2$, SiR$_3$, (S=O)R, (S=O)$_2$R, (P=O)R$_2$;
R is independently selected from a linear C$_1$-C$_{20}$ alkyl, linear C$_1$-C$_{20}$ alkoxy, linear C$_1$-C$_{20}$ thioalkyl, a branched C$_3$-C$_{20}$ alkyl, branched C$_3$-C$_{20}$ alkoxy, branched C$_3$-C$_{20}$ thioalkyl, C$_{6-20}$ aryl and C$_3$-C$_{20}$ heteroaryl;
m is selected from 1 or 2.

7. The compound according to claim 1, wherein
Ar$^2$ is selected from formula F1 to F16;

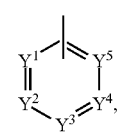  (F1)

wherein
Y$^1$ to Y$^5$ are independently selected from N, OR, SR, (C=O)R, (C=O)NR$_2$, SiR$_3$, (S=O)R, (S=O)$_2$R, (P=O)R$_2$, C—H, C—R, and/or at least two of Y$^1$ to Y$^5$, which are connected to each other by a chemical bond, are bridged to form an anellated aromatic ring or anellated heteroaromatic ring,
  wherein R is independently selected from a linear C$_1$-C$_{20}$ alkyl, linear C$_1$-C$_{20}$ alkoxy, linear C$_1$-C$_{20}$ thioalkyl, a branched C$_3$-C$_{20}$ alkyl, branched C$_3$-C$_{20}$ alkoxy, branched C$_3$-C$_{20}$ thioalkyl, C$_{6-20}$ aryl and C$_3$-C$_{20}$ heteroaryl;

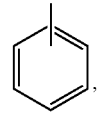  (F2)

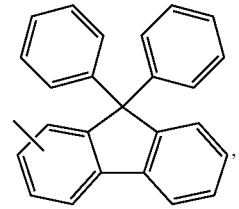  (F3)

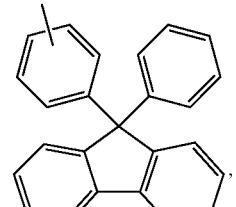  (F4)

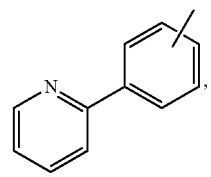  (F5)

(F6) 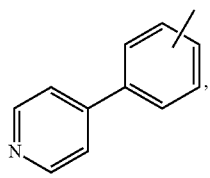

(F7) 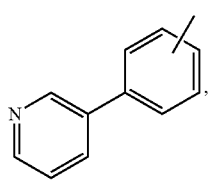

(F8) 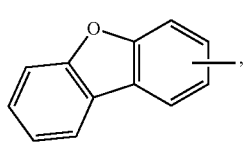

(F9) 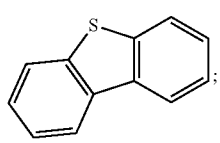

(F10) 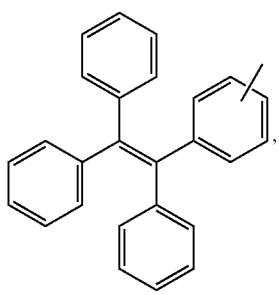

(F11) 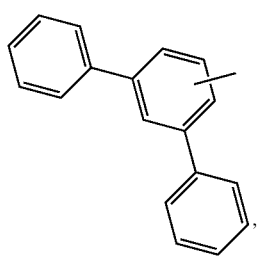

(F12) 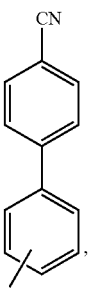

(F13) 

(F14) 

(F15) 

(F16) 

8. The compound according to claim 1, wherein $Ar^2$ comprises at least one ring selected from the group consisting of pyridine, pyrimidine, and or triazine.

9. The compound according to claim 1, wherein $Ar^2$ comprises at least one substituted or unsubstituted 1,1,2,2-Tetraphenylethylene group, which is:
   bonded via a single bond to a pyridine, a pyrimidine, a triazine ring, or
   a phenyl group, wherein the phenyl group is bonded via a single bond to pyridine, pyrimidine, or triazine ring.

10. The compound according to claim 1, wherein the compound of Formula I is selected from G1 to G30:

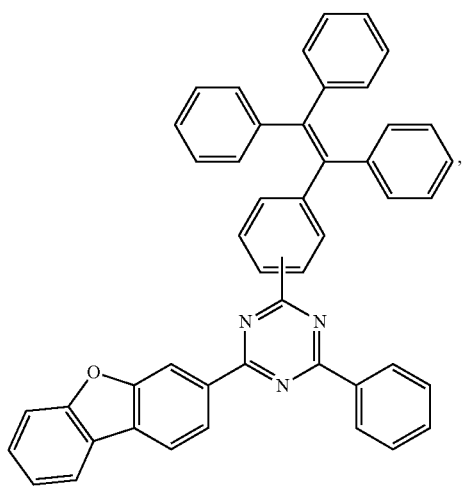
(G1)
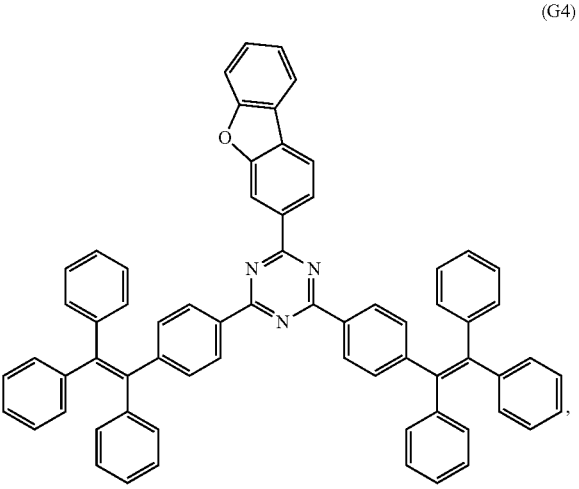
(G4)
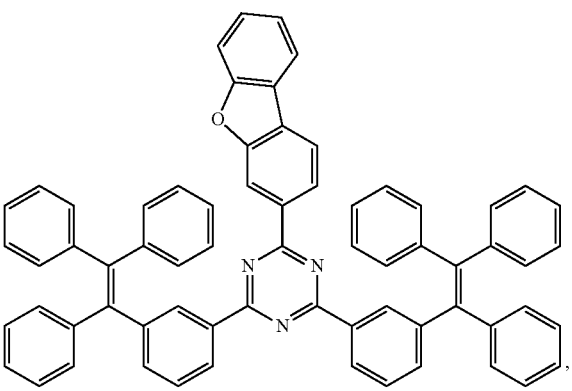
(G2)
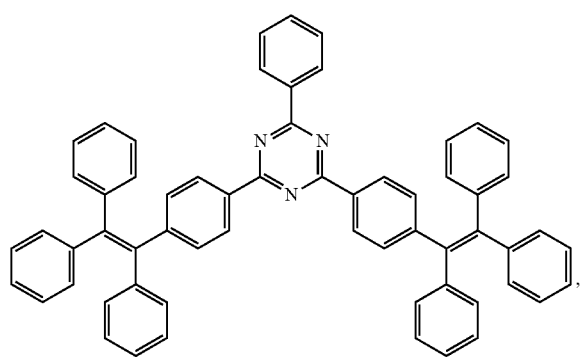
(G3)
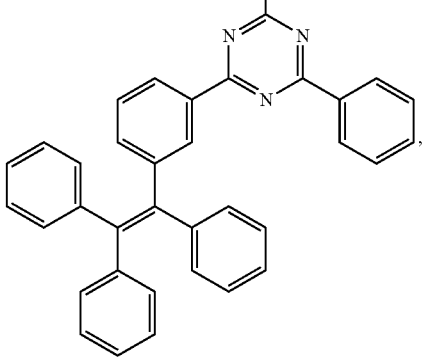
(G5)
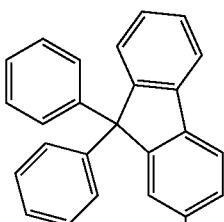
(G6)

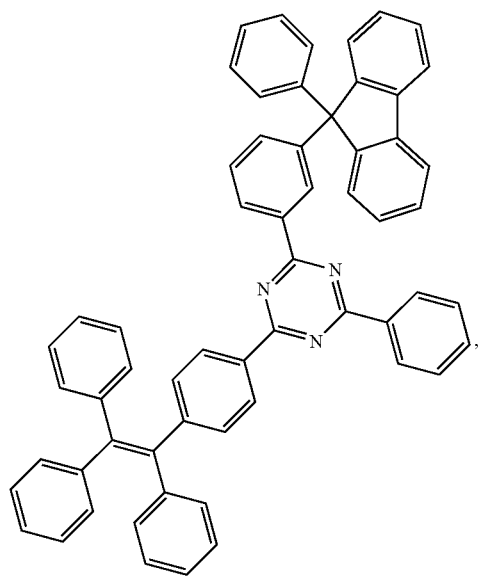
(G7)
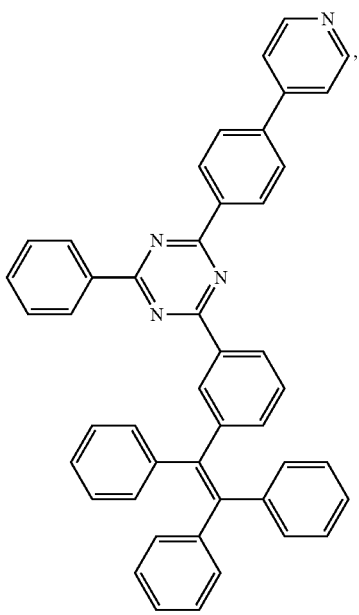
(G9)
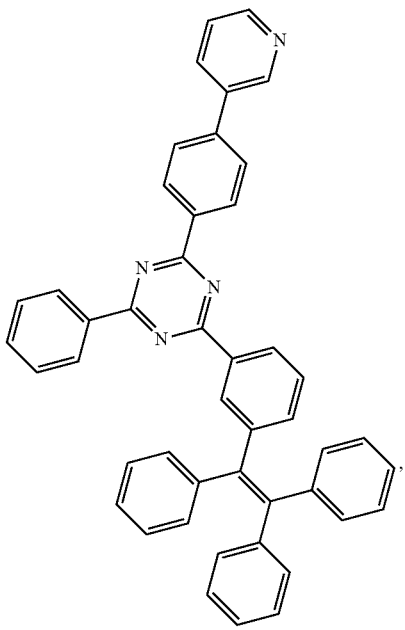
(G10)

(G11)
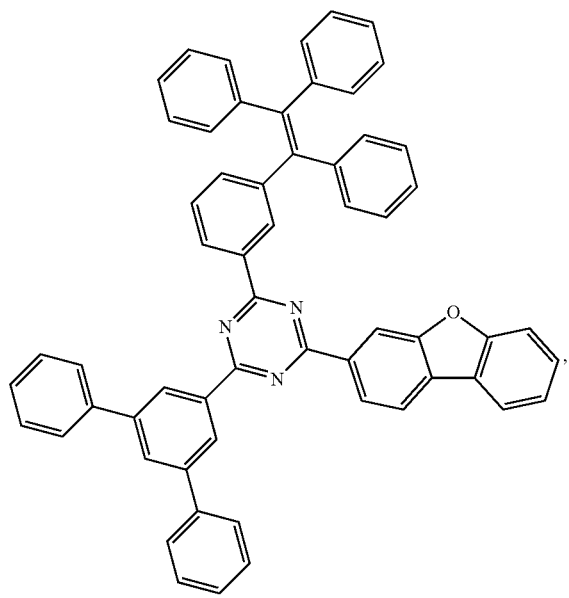
(G12)
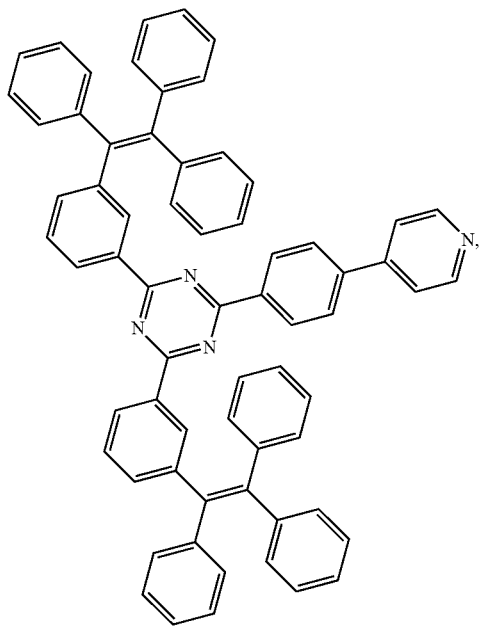
(G13)
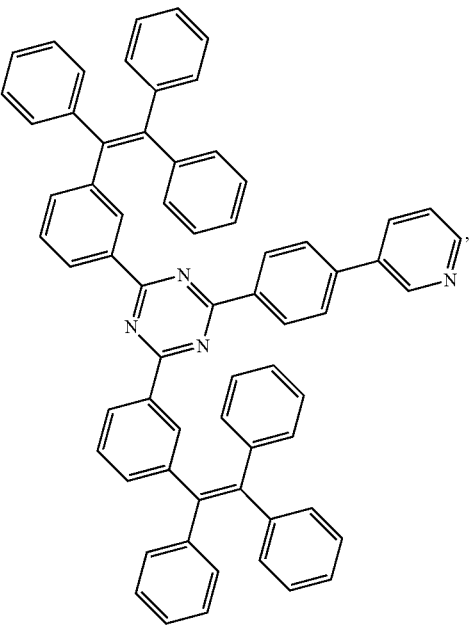
(G14)
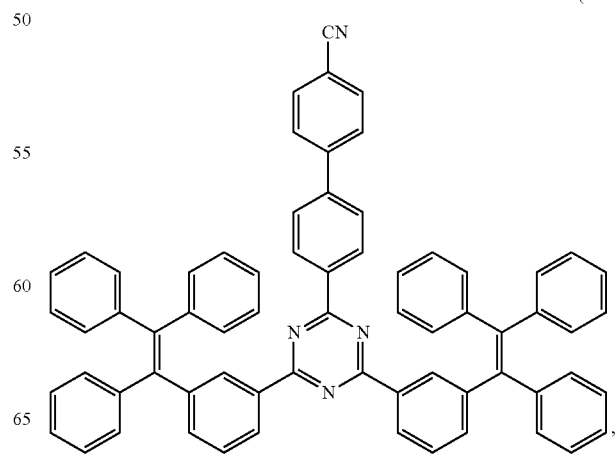

(G15)
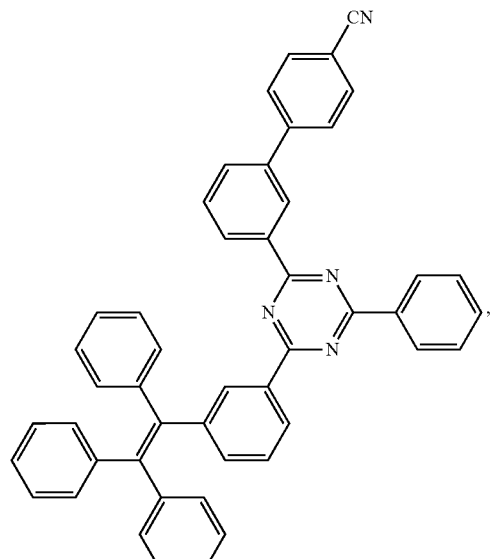
(G16)
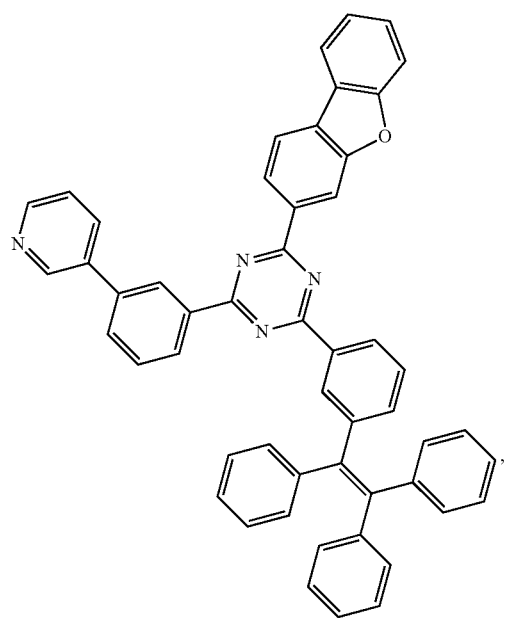
(G17)
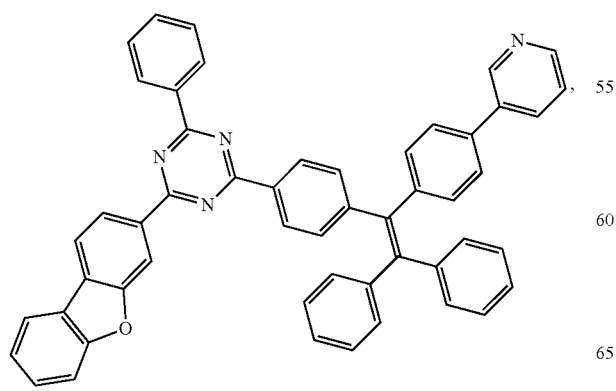
(G18)
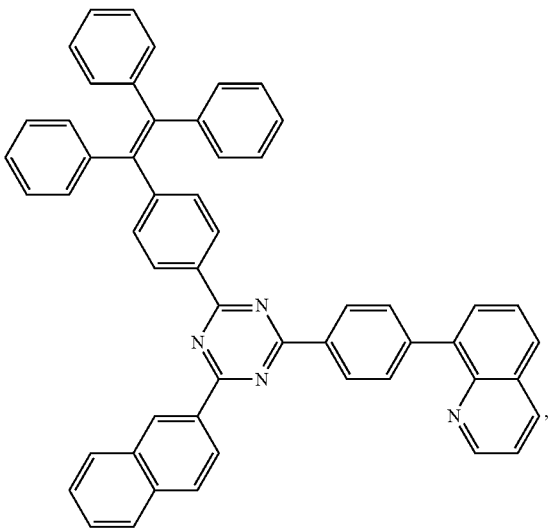
(G19)
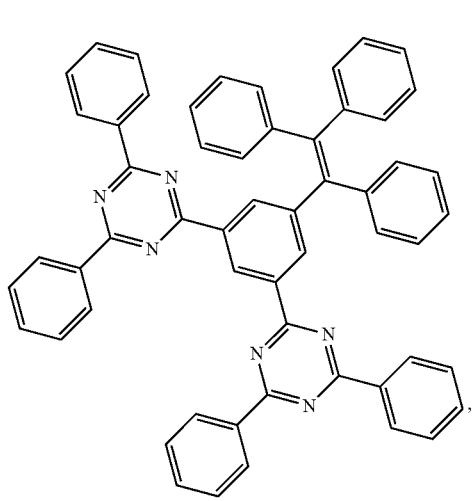

101
-continued
(G20)
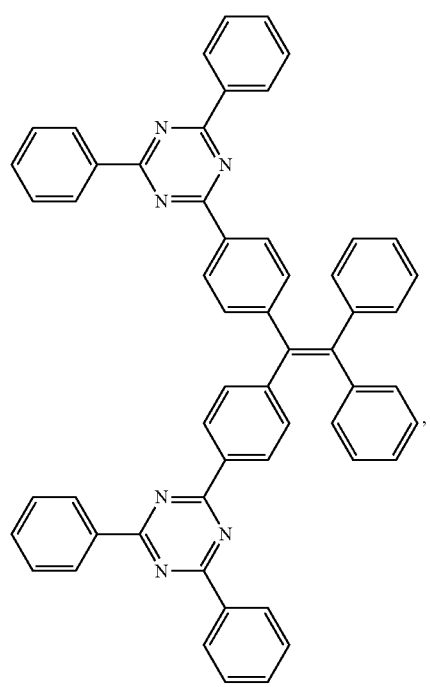
(G21)
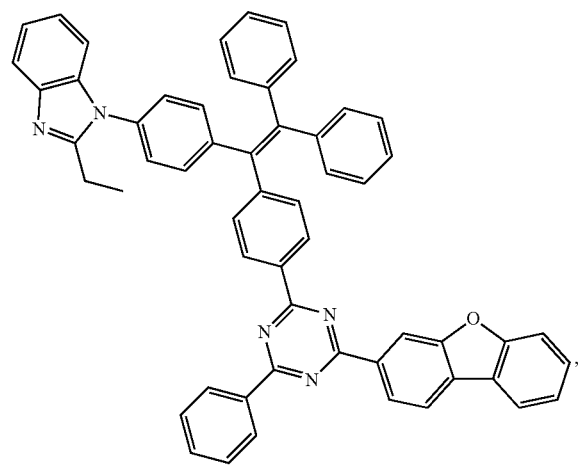
102
-continued
(G22)
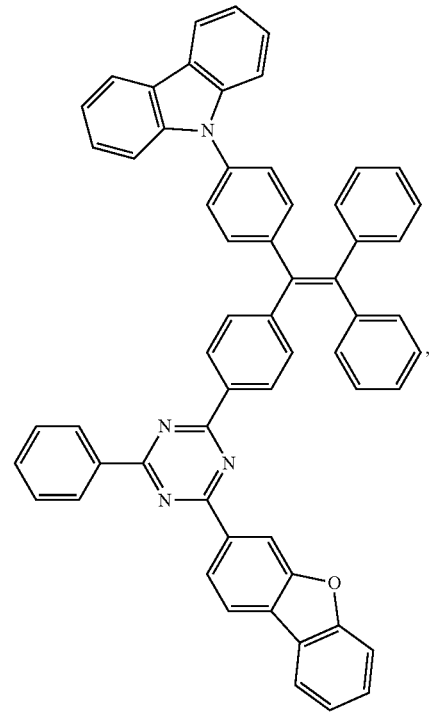
(G23)

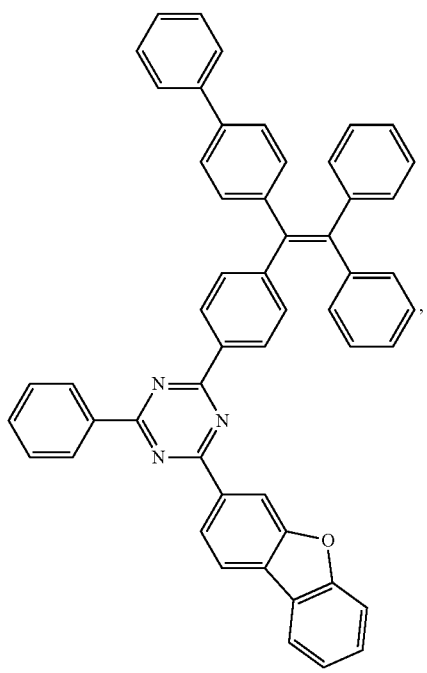
(G24)
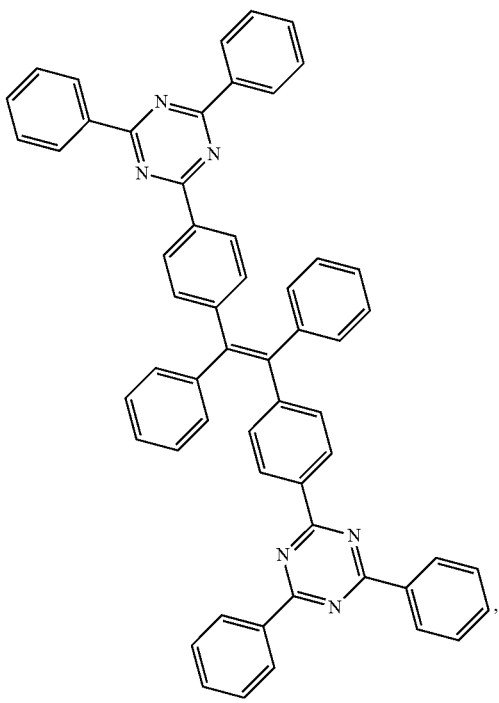
(G26)
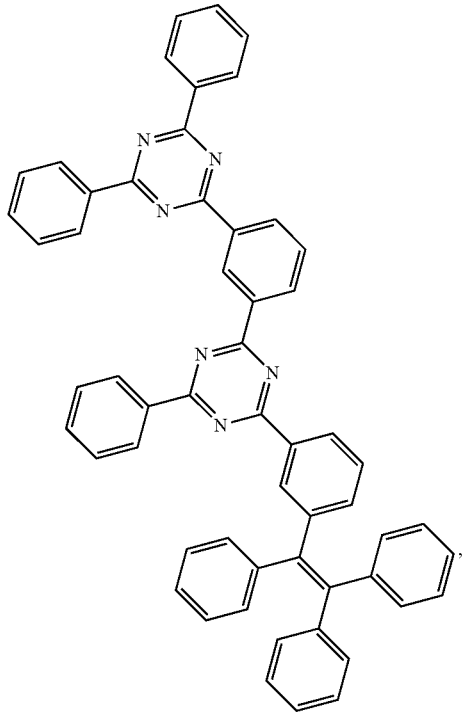
(G25)
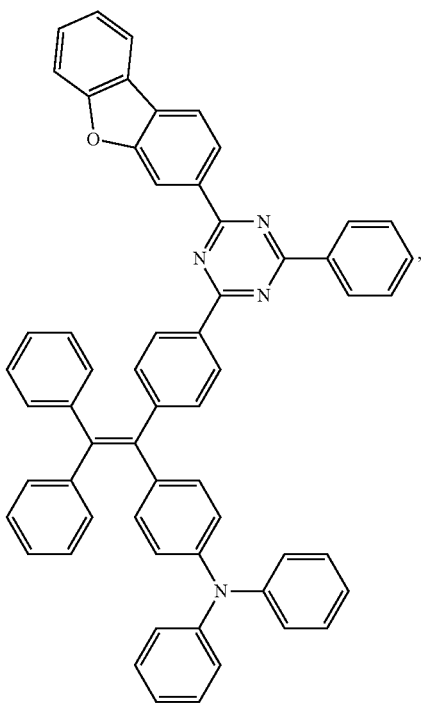
(G27)

-continued (G28)
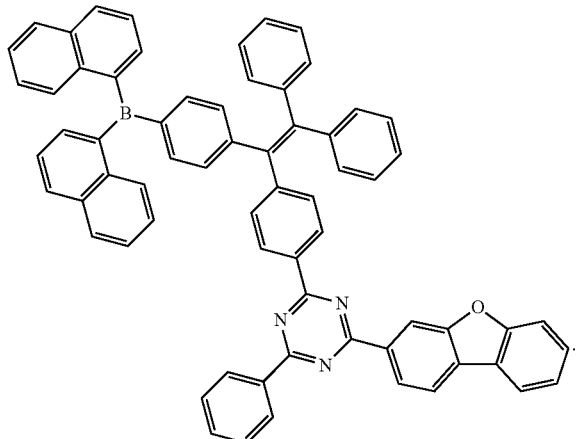

(G29)
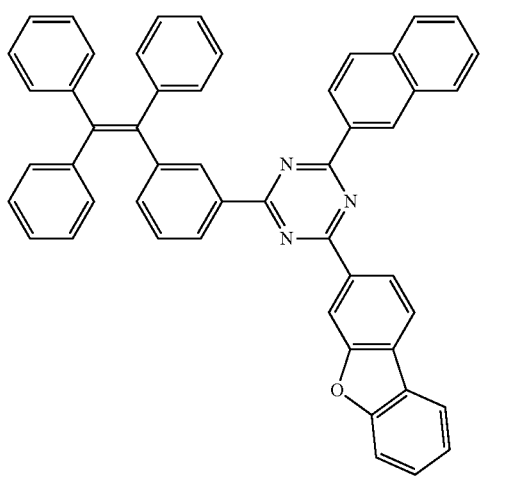 [SMILES: c1ccc(C(=C(c2ccccc2)c2cccc(-c3nc(-c4ccc5ccccc5c4)nc(-c4ccc5c(c4)oc4ccccc45)n3)c2)c2ccccc2)cc1]

(G30)
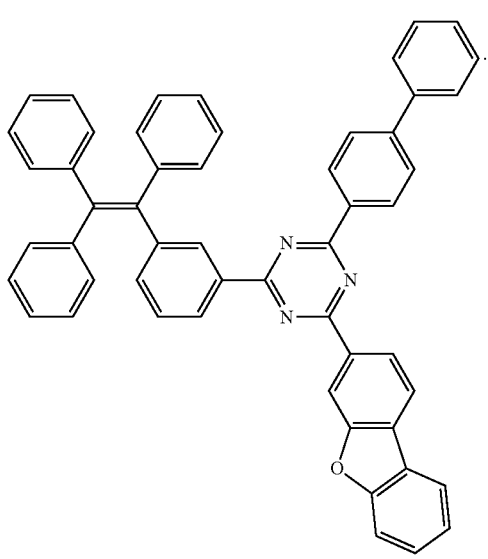

11. An organic electronic device comprising an organic semiconductor layer, wherein at least one organic semiconductor layer comprises a compound of formula I to claim 1.

12. The organic electronic device according to claim 11, wherein the organic semiconductor layer is essentially non-emissive or non-emitting.

13. The organic electronic device according to claim 11, wherein the organic semiconductor layer is an electron transport layer, a hole injection layer, a hole transport layer, an emission layer, an electron blocking layer, a hole blocking layer or an electron injection layer.

14. The organic electronic device according to claim 11, wherein the organic semiconductor layer is arranged between a photoactive layer and a cathode layer.

15. The organic electronic device according to claim 11, wherein the at least one, organic semiconductor layer further comprises at least one alkali halide or alkali organic complex.

16. The organic electronic device according to claim 11, wherein the electronic device comprises at least one organic semiconductor layer, at least one anode layer, at least one cathode layer and at least one emission layer.

17. The organic electronic device according to claim 11, wherein the electronic device is a light emitting device, thin film transistor, a battery, a display device or a photovoltaic cell.

18. The compound according to claim 1, wherein the compound according to formula I comprises at least one of the aromatic rings A, B, C and D, wherein at least one thereof is different substituted.

19. The compound according to claim 1, wherein the compound according to formula I is non-superimposable on its mirror image.

20. The compound according to claim 1, wherein the compound according to formula I comprises at least one hetero atom selected from the group consisting of N, O, S, $(P=O)R_2$, and —CN.

21. The compound according to claim 1, wherein the compound according to formula I comprises at least two triazine rings.

22. The compound according to claim 1, wherein the compound according to formula I comprises one non-hetero tetraarylethylene group (TAE) only.

23. The compound according to claim 1, wherein the compound according formula I comprises one hetero tetraarylethylene group (TAE) only.

24. The compound according to claim 1, wherein the $Ar^2$ group comprises 1 to 10 non-hetero aromatic 6 membered rings.

25. The compound according to claim 1, wherein the AC group comprises at least one $C_6$ to $C_{18}$ arylene.

26. The compound according to claim 1, wherein the $Ar^2$ group Comprises at least one $C_6$ or $C_{12}$ arylene that is anellated to at least one aromatic ring A, B, C and D of formula I.

27. The compound according to claim 1, wherein $Ar^2$ comprises at least one substituted or unsubstituted benzothiazole group.

28. The compound according to claim 1, wherein $Ar^2$ comprises at least one nitril, at least one phosphine oxide substituent, or a combination thereof.

29. The compound according to claim 1, wherein $Ar^2$ is free of a group selected from pyridine, pyrimidine, triazine, or a substituted or unsubstituted benzothiazole group.

* * * * *